US009186685B2

(12) United States Patent
Marziali et al.

(10) Patent No.: US 9,186,685 B2
(45) Date of Patent: Nov. 17, 2015

(54) MULTIPLE ARM APPARATUS AND METHODS FOR SEPARATION OF PARTICLES

(71) Applicant: The University of British Columbia, Vancouver (CA)

(72) Inventors: Andrea Marziali, North Vancouver (CA); Joel Pel, Vancouver (CA)

(73) Assignee: The University of British Columbia, Vancouver (CA)

( * ) Notice: Subject to any disclaimer, the term of this patent is extended or adjusted under 35 U.S.C. 154(b) by 461 days.

(21) Appl. No.: 13/739,337

(22) Filed: Jan. 11, 2013

(65) Prior Publication Data

US 2013/0180856 A1 Jul. 18, 2013

Related U.S. Application Data

(60) Provisional application No. 61/598,236, filed on Feb. 13, 2012, provisional application No. 61/586,727, filed on Jan. 13, 2012.

(51) Int. Cl.
*B03C 7/02* (2006.01)
*B03C 5/02* (2006.01)

(52) U.S. Cl.
CPC . *B03C 7/02* (2013.01); *B03C 5/026* (2013.01); *B03C 2201/26* (2013.01)

(58) Field of Classification Search
None
See application file for complete search history.

(56) References Cited

U.S. PATENT DOCUMENTS

| | | |
|---|---|---|
| 4,148,703 A | 4/1979 | Trop et al. |
| 4,390,403 A | 6/1983 | Batchelder |
| 4,390,404 A | 6/1983 | Esho et al. |
| 4,732,656 A | 3/1988 | Hurd |
| 4,911,817 A | 3/1990 | Kindlmann |
| 4,971,671 A | 11/1990 | Slater et al. |
| 5,084,157 A | 1/1992 | Clark et al. |
| 5,185,071 A | 2/1993 | Serwer et al. |
| 5,286,434 A | 2/1994 | Slater et al. |
| 5,384,022 A | 1/1995 | Rajasekaran |
| 5,453,162 A | 9/1995 | Sabanayagam et al. |

(Continued)

FOREIGN PATENT DOCUMENTS

| | | |
|---|---|---|
| CA | 2552262 A1 | 8/2005 |
| CA | 2523089 A1 | 4/2006 |

(Continued)

OTHER PUBLICATIONS

Anonymous, "Nucleic Acid Purification + Technical Presentation," Boreal Genomics, http://www.borealgenomics.com/technology/purification/, Jan. 24, 2010.

(Continued)

*Primary Examiner* — J Christopher Ball
(74) *Attorney, Agent, or Firm* — Brown Rudnick LLP

(57) ABSTRACT

The invention provides apparatus for separation of particles and methods for using the apparatus. In an embodiment, the apparatus includes three arms extending radially from a central reservoir, each arm being associated with a separation electrode. At least one on the arms includes a separation medium. Using a sequence of driving and mobility-changing voltages, target particles can be separated from closely related particles within a sample. For example, single point mutations can be resolved from a sample containing predominantly wild type nucleic acids.

16 Claims, 28 Drawing Sheets

(56) References Cited

U.S. PATENT DOCUMENTS

| | | | |
|---|---|---|---|
| 5,609,743 | A | 3/1997 | Sasagawa et al. |
| 5,641,628 | A | 6/1997 | Bianchi |
| 5,938,904 | A | 8/1999 | Bader et al. |
| 6,036,831 | A | 3/2000 | Bishop |
| 6,110,670 | A | 8/2000 | Van Broeckhoven et al. |
| 6,146,511 | A | 11/2000 | Slater et al. |
| 6,193,866 | B1 | 2/2001 | Bader et al. |
| 6,258,540 | B1 | 7/2001 | Lo et al. |
| 6,693,620 | B1 | 2/2004 | Herb et al. |
| 6,824,664 | B1 | 11/2004 | Austin et al. |
| 6,827,830 | B1 | 12/2004 | Slater et al. |
| 6,893,546 | B2 | 5/2005 | Jullien et al. |
| 6,927,028 | B2 | 8/2005 | Dennis et al. |
| 7,175,747 | B2 | 2/2007 | Bayerl et al. |
| 7,198,702 | B1 | 4/2007 | Washizu et al. |
| 7,371,533 | B2 | 5/2008 | Slater et al. |
| 7,427,343 | B2 | 9/2008 | Han et al. |
| 7,442,506 | B2 | 10/2008 | Dhallan |
| 7,452,668 | B2 | 11/2008 | Boles et al. |
| 7,838,647 | B2 | 11/2010 | Hahn et al. |
| 7,888,017 | B2 | 2/2011 | Quake et al. |
| 8,008,018 | B2 | 8/2011 | Quake et al. |
| 8,182,666 | B2 | 5/2012 | Marziali et al. |
| 8,195,415 | B2 | 6/2012 | Fan et al. |
| 2001/0045359 | A1 | 11/2001 | Cheng et al. |
| 2002/0036139 | A1 | 3/2002 | Becker et al. |
| 2002/0081280 | A1 | 6/2002 | Curiel et al. |
| 2002/0119448 | A1 | 8/2002 | Sorge et al. |
| 2002/0179445 | A1 | 12/2002 | Alajoki et al. |
| 2003/0027178 | A1 | 2/2003 | Vasmatzis et al. |
| 2003/0215855 | A1 | 11/2003 | Dubrow et al. |
| 2005/0164241 | A1 | 7/2005 | Hahn et al. |
| 2005/0164402 | A1 | 7/2005 | Belisle et al. |
| 2005/0247563 | A1 | 11/2005 | Shuber et al. |
| 2005/0247564 | A1 | 11/2005 | Volkel et al. |
| 2007/0215472 | A1 | 9/2007 | Slater et al. |
| 2007/0218494 | A1 | 9/2007 | Slater et al. |
| 2008/0108063 | A1 | 5/2008 | Lucero et al. |
| 2008/0314751 | A1 | 12/2008 | Bukshpan et al. |
| 2009/0120795 | A1 | 5/2009 | Marziali et al. |
| 2009/0139867 | A1 | 6/2009 | Marziali et al. |
| 2009/0152116 | A1 | 6/2009 | Boles et al. |
| 2010/0285537 | A1 | 11/2010 | Zimmermann |
| 2011/0048950 | A1 | 3/2011 | Marziali et al. |
| 2011/0245482 | A1 | 10/2011 | Hahn et al. |
| 2011/0272282 | A1 | 11/2011 | Marziali et al. |
| 2012/0048735 | A1 | 3/2012 | Marziali et al. |
| 2012/0160682 | A1 | 6/2012 | Marziali et al. |
| 2012/0199481 | A1 | 8/2012 | Marziali et al. |

FOREIGN PATENT DOCUMENTS

| | | |
|---|---|---|
| CA | 2496294 A1 | 8/2006 |
| CA | 2641326 A1 | 8/2006 |
| CA | 2713313 A1 | 8/2009 |
| CA | 2742460 A1 | 5/2010 |
| EP | 0356187 A2 | 2/1990 |
| EP | 1720636 A1 | 11/2006 |
| EP | 1859249 | 11/2007 |
| EP | 2238434 | 10/2010 |
| EP | 2458004 A1 | 5/2012 |
| GB | 2249395 A | 5/1992 |
| JP | 7-167837 A | 7/1995 |
| JP | 2000-505545 A | 5/2000 |
| JP | 2001-165906 A | 6/2001 |
| JP | 2002-502020 A | 1/2002 |
| JP | 2003-062401 A | 3/2003 |
| JP | 2003-066004 A | 3/2003 |
| JP | 2003-513240 A | 4/2003 |
| JP | 2003-215099 A | 7/2003 |
| JP | 2003-247980 A | 9/2003 |
| WO | 9514923 A1 | 6/1995 |
| WO | 9727933 A1 | 8/1997 |
| WO | 9938874 A2 | 8/1999 |
| WO | 9945374 A2 | 9/1999 |
| WO | 0131325 A1 | 5/2001 |
| WO | 0242500 A2 | 5/2002 |
| WO | 03019172 A2 | 3/2003 |
| WO | 2006063625 A1 | 6/2006 |
| WO | 2007092473 A2 | 8/2007 |
| WO | 2010/104798 A1 | 9/2010 |
| WO | 2010121381 A1 | 10/2010 |
| WO | 2013002616 A2 | 1/2013 |

OTHER PUBLICATIONS

Asbury, et al., "Trapping of DNA by dielectrophoresis", Electrophoresis, 2002, 23:2658-2666.

Asbury, et al., "Trapping of DNA in Nonuniform Oscillating Electric Fields", Biophysical Journal, 1998, 74:1024-1030.

Astumian, et al., "Fluctuation Driven Ratchets: Molecular Motors", Physical Review Letters, 1994, 72(11):1766-1769.

Bier, Martin, et al., "Biasing Brownian Motion in Different Directions in a 3-State Fluctuating Potential and an Application for the Separation of Small Particles", Physical Review Letters, 1996, 76(22):4277-4280.

Carle, G.F., et al., "Electrophoretic Separations of Large DNA Molecules by Periodic Inversion of the Electric Field", Science, 1986, 232(4726):65-68.

Chacron, M.J., et al., "Particle trapping and self-focusing in temporarily asymmetric ratchets with strong field gradients", Physical Review E, 1997, 56(3):3446-3450.

Chakrabarti, Subrata, et al., "Highly Selective Isolation of Unknown Mutations in Diverse DNA Fragments: Toward New Multiplex Screening in Cancer", American Association for Cancer Reserch, 2000, 60:3732-3737.

Chan, K.C. Allen, et al., "Size Distributions of Maternal and Fetal DNA in Maternal Plasma", Molecular Diagnostics and Genetics, Clinical Chemistry, 2004, 50(1):88-92.

Chu, Gilbert, "Bag model for DNA migration during pulsed-field electrophoresis", Proc. Natl. Acad. Sci., 1991, 88:11071-11075.

European Search Report corresponding to EP11004417, Mar. 29, 2012, 4 pages.

Frumin, L.L., et al., "Anomalous size dependence of the non-linear mobility of DNA", In PhysChemComm, 2000, 11 (3):61-63.

Frumin, L.L., et al., "Nonlinear focusing of DNA macromolecules", Physical Review E—Statistical, Nonlinear and Soft Matter Physics, 2001, 64:021902-1-5.

Griess, Gary A., et al., "Cyclic capillary electrophoresis", Electrophoresis, 2002, 23:2610-2617.

International Preliminary Report on Patentability corresponding to PCT/CA2005/000124, Aug. 7, 2006, 8 pages.

International Preliminary Report on Patentability corresponding to PCT/CA2006/000172, Aug. 7, 2007, 8 pages.

International Preliminary Report on Patentability corresponding to PCT/CA2009/000111, Aug. 3, 2010, 9 pages.

International Search Report dated Feb. 23, 2010 corresponding to PCT/CA2009/001648, 6 pages.

International Search Report for PCT/CA2006/000172, International Searching Authority, Jun. 2, 2006, 4 pages.

Jorgez, Carolina J., et al., "Quantity versus quality: Optimal methods for cell-free DNA isolation from plasma of pregnant women", American College of Medical Genetics, 2006, 8(10):615-619.

Kitzman, Jacob O., et al., "Noninvasive Whole-Genome Sequencing of a Human Fetus", Sci Transl Med 4, 137ra76 (2012); DOI: 10.1126/scitranslmed.3004323, 9 pages.

Kopecka, K., et al., "Capillary electrophoresis sequencing of small ssDNA molecules versus the Ogston regime: Fitting data and interpreting parameters", Electrophoresis, 2004, 25(14):2177-2185.

LaLande, Marc, et al., "Pulsed-field electrophoresis: Application of a computer model to the separation of large DNA molecules", Proc. Natl. Acad. Sci. USA, 1987, 84:8011-8015.

Lun, Fiona M. F., et al., "Microfluidics Digital PCR Reveals a Higher than Expected Fraction of Fetal DNA in Maternal Plasma", Molecular Diagnostics and Genetics, Clinical Chemistry, 2008, 54(10):1664-1672.

Magnasco, Marcelo, O., "Forced Thermal Ratchets", Physical Review Letters, 1993, 71(10):1477-1481.

(56) References Cited

OTHER PUBLICATIONS

Makridakis, Nick M., "PCR-free method detects high frequency of genomic instability in prostate cancer", Nucleic Acids Research, 2009, 37(22):7441-7446.

Nollau, Peter, et al., "Methods for detection of point mutations: performance and quality assessment", Department of Clinical Chemistry, 1997, 43(7):1114-1128.

Office Action mailed Aug. 19, 2011 for U.S. Appl. No. 11/815,760.

Office Action mailed Dec. 27, 2010 for U.S. Appl. No. 11/815,760.

Pel, J., "A novel electrophoretic mechanism and separation parameter for selective nucleic acid concentration based on synchronous coefficient of drag alteration (SCODA)", (Ph.D. Thesis), Vancouver: University of British Columbia, 2009.

Rousseau, J., et al., "Gel electrophoretic mobility of single-stranded DNA: The two reptation field-dependent factors", Electrophoresis, 2000, 21(8):1464-1470.

Sikora, Aleksandra, et al., "Detection of Increased Amounts of Cell-Free DNA with Short PCR Amplicons", Clinical Chemistry, 2010, 56(1):136-138.

Slater, G.W., et al., "Recent developments in DNA electrophoretic separations", Electrophoresis, 1998, 19 (10):1525-1541.

Slater, G.W., et al., "The theory of DNA separation by capillary electrophoresis", Current Opinion in Biotechnology, 2003, 14:58-64.

Slater, G.W., et al., "Theory of DNA electrophoresis: A look at some current challenges", Electrophoresis, 2000, 21:3873-3887.

So. A., et al., "Efficient genomic DNA extraction from low target concentration bacterial cultures using SCODA DNA extraction technology", Cold Spring Harb Protoc, 2010, 1150-1153; 1185-1198.

Supplementary European Search Report corresponding to EP09706657, May 12, 2011, 2 pages.

Supplementary Partial European Search Report corresponding to EP05706448, May 14, 2012, 3 pages.

Tessier, F. et al. "Strategies for the separation of polyelectrolytes based on non-linear dynamics and entropic ratchets in a simple microfluidic device", Applied Physics A—Materials Science & Processing, 2002, 75:285-291.

Thompson, J.D., et al., "Winnowing DNA for Rare Sequences: Highly Specific Sequence and Methylation Based Enrichment," PLOS One, vol. 7, No. 2, Feb. 15, 2012.

Turmel, C., et al., "Molecular detrapping and band narrowing with high frequency modulation of pulsed field electrophoresis", Nucleic Acids Research, 1990, 18(3):569-575.

Viovy, J.L., "Electrophoresis of DNA and other polyelectrolytes: Physical mechanisms", Review of Modern Physics, 2000, 72(3):813-872.

Wright, Caroline, "Cell-free fetal nucleic acids for non-invasive prenatal diagnosis", Report of the UK export working group, Jan. 2009, 64 pages.

Yobas, L., et al., "Nucleic Acid Extraction, Amplification, and Detection on Si-Based Microfluidic Platforms," IEEE Journal of Solid-State Circuits, vol. 42, No. 8, Aug. 2007, 12 pages.

Baba, Yoshinobu, "Capillary Affinity Gel Electrophoresis", Molecular Biotechnology, 1996, (9):1-11.

International Search Report for PCT/CA2012/050576, Feb. 28, 2013 3 pages.

Hot pulse (at 70degC)

start    Arm A end

5m Injection

25m Defocus

90m Defocus

150m Defocus
Bands are stabilized

MULTIPLE ARM APPARATUS AND METHODS FOR SEPARATION OF PARTICLES

RELATED APPLICATIONS

This Application claims priority to U.S. Provisional Application No. 61/586,727 filed Jan. 13, 2012 and U.S. Provisional Application No. 61/598,236 filed Feb. 13, 2012, both of which are incorporated by reference in their entirety.

FIELD OF THE INVENTION

Embodiments of the present invention relate to the induced movement of particles through media such as gels and other matrices. Some embodiments provide methods and apparatus for selectively purifying, separating, concentrating and/or detecting particles.

BACKGROUND

One mechanism for purifying, separating, or concentrating molecules of interest is called Synchronous Coefficient Of Drag Alteration (or "SCODA") based purification. SCODA is an approach that may be applied for purifying, separating, or concentrating particles. SCODA may be applied, for example, to DNA, RNA and other molecules including proteins and polypeptides.

SCODA-based transport is used to produce net motion of a molecule of interest by synchronizing a time-varying driving force, which would otherwise impart zero net motion, with a time-varying drag (or mobility) altering field. If application of the driving force and periodic mobility alteration are appropriately coordinated, the result is net motion despite zero time-averaged driving force.

SCODA is described in the following publications:

U.S. Patent Publication No. 2009/0139867 entitled "Scodaphoresis and methods and apparatus for moving and concentrating particles";

PCT Publication No. WO 2006/081691 entitled "Apparatus and methods for concentrating and separating particles such as molecules";

PCT Publication No. WO 2009/094772 entitled "Methods and apparatus for particle introduction and recovery";

PCT Publication No. WO 2010/051649 entitled "Systems and methods for enhanced SCODA";

PCT Publication No. WO 2010/121381 entitled "System and methods for detection of particles";

U.S. patent application Ser. No. 13/153,185 filed 3 Jun. 2011 entitled "Systems and methods for enhanced SCODA";

U.S. patent application Ser. No. 13/218,124 filed 25 Aug. 2011 entitled "Systems and methods for enrichment and detection of particles";

Marziali, A.; Pel, J.; Bizotto, D.; Whitehead, L. A., "Novel electrophoresis mechanism based on synchronous alternating drag perturbation", Electrophoresis 2005, 26, 82-89;

Broemeling, D.; Pel, J.; Gunn, D.; Mai, L.; Thompson, J.; Poon, H.; Marziali, A., "An Instrument for Automated Purification of Nucleic Acids from Contaminated Forensic Samples", JALA 2008, 13, 40-48;

Pel, J.; Broemeling, D.; Mai, L.; Poon, H.; Tropini, G.; Warren, R.; Holt, R.; Marziali, A., "Nonlinear electrophoretic response yields a unique parameter for separation of biomolecules", PNAS 2008, vol. 106, no. 35, 14796-14801; and So, A.; Pel, J.; Rajan, S.; Marziali, A., "Efficient genomic DNA extraction from low target concentration bacterial cultures using SCODA DNA extraction technology", Cold Spring Harb. Protoc. 2010, 1150-1153, each of which is hereby incorporated herein by reference in its entirety for all purposes.

SUMMARY

The invention provides a particle separation apparatus and methods for its use. The apparatus is relatively simple in construction, but can be used to extract populations of target particles from samples having a preponderance of similar, but different, particles. For example, using the invention, it is straightforward to extract DNA having single point mutations from a sample containing a preponderance of wild-type DNA. It is also straightforward to extract DNA having epigenetic variations, e.g., differential methylation. Accordingly, the apparatus lends itself to the isolation of genetic and epigenetic differences in a heterogeneous sample, and is useful for tasks such as genotyping cancers or identifying fetal genetic material in a maternal sample.

In an embodiment, the apparatus includes at least three electrodes circumferentially surrounding a central reservoir with a separation medium between at least one electrode and the central reservoir. Typically, the central reservoir will contain a buffer or an additional separation medium, making it possible to recover the targeted molecules, e.g. for amplification and/or sequencing. In one arrangement, the apparatus includes arms extending outward from the central reservoir, each arm being associated with an electrode.

In an embodiment, the separation medium comprises an affinity agent that has a binding affinity for a targeted particle, such as a DNA sequence having a point mutation. The affinity agent can be a nucleic acid, a small molecule, a protein, or an aptamer. The separation may be performed by applying a time-varying driving field to the separation medium while varying the temperature of the separation medium about the melting temperature of the targeted particle-affinity agent binding pair.

In some embodiments, the apparatus additionally includes a loading reservoir adjacent the separation medium. The loading reservoir allows the targeted particles to be injected into the loading reservoir as part of a mixed sample, whereby the targeted particles are electrophoretically loaded onto the separation medium, separated while traversing the separation medium, and then collected in the central reservoir. The entire separation apparatus, including the loading reservoir can be incorporated into a cassette for ease of use and replacement.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

FIG. 21A shows injection at 10° C., FIG. 21B shows injection at 25° C., FIG. 21C shows injection at 40° C., and FIG. 21D shows injection at 50° C. FIGS. 21Ai, 21Bi, 21Ci and 12Di are schematic representations of the images shown in FIGS. 21A, 21B, 21C and 21D, respectively, wherein stippling is used on a white background to show the approximate location of the fluorescently-labeled DNA in the images.

FIG. 22A shows injection at 0M NaCl, FIG. 22B shows injection at 0.2M NaCl, and FIG. 22C shows injection at 0.3M NaCl. FIGS. 22Ai, 22Bi and 22Ci are schematic representations of FIGS. 22A, 22B and 22C, respectively, wherein stippling is used on a white background to show the approximate location of the fluorescently-labeled DNA in the images.

FIG. 23A shows 60 minutes of injection at 25 V/cm at 25° C. for a 91 base pair double stranded DNA with H2A present in the gel. FIG. 23B shows the same sample as panel (A) after 200 minutes of SCODA focusing at 40 V/cm at 50° C. FIG. 23C shows 10 minutes of injection at 25 V/cm at 25° C. for the same 91 base pair double stranded DNA with no protein present in the gel. FIG. 23D shows the same sample as FIG. 23C after 80 minutes of SCODA focusing at 40 V/cm at 50° C. FIGS. 23Ai, 23Bi, 23Ci and 23Di are schematic representations of FIGS. 23A, 23B, 23C and 23D, respectively, wherein stippling is used on a white background to show the approximate location of the fluorescently-labeled DNA in the images.

FIG. 24A shows the gel after injecting for 10 minutes at 25 V/cm at 25° C. FIG. 24B shows the same gel after 110 minutes of SCODA focusing at 40 V/cm at 50° C. FIGS. 24Ai and 24Bi are schematic representations of FIGS. 24A and 24B, respectively, wherein stippling is used on a white background to show the approximate location of the fluorescently labeled DNA in the images.

FIG. 25A shows injection after 7 minutes of applying a DC-field of 25 V/cm at 25° C., and FIG. 25B shows the same sample after SCODA focusing at 40 V/cm for 10 minutes. FIGS. 25Ai and 25Bi are schematic representations of FIGS. 25A and 25B, respectively, wherein stippling is used on a white background to show the approximate location of the fluorescently-labeled DNA in the images.

DETAILED DESCRIPTION

Figure 1:
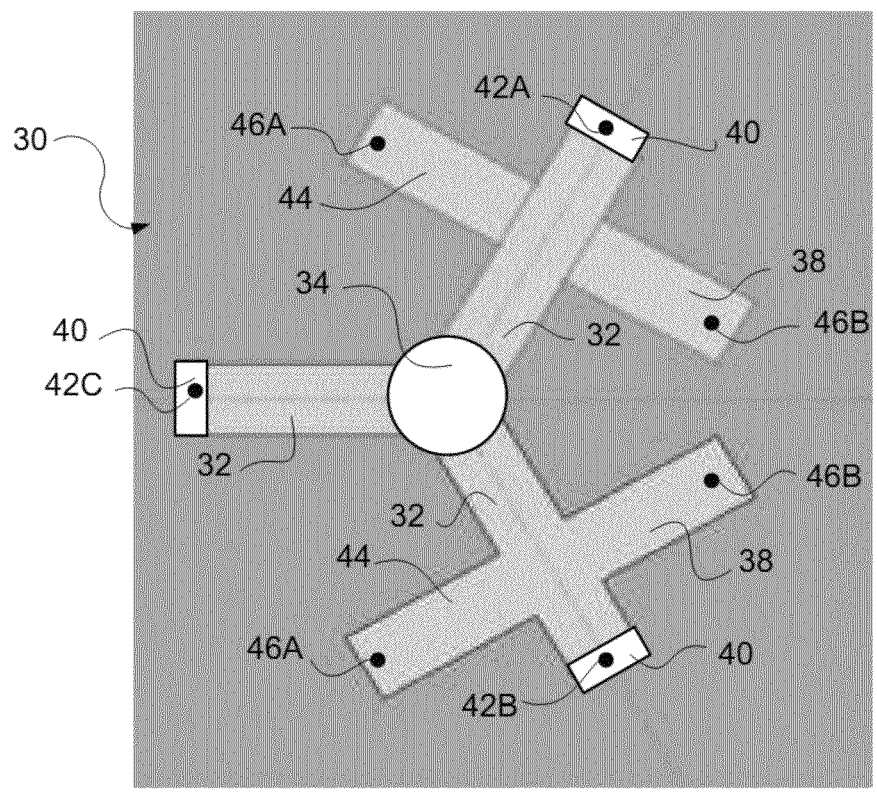
FIG. 1 shows an embodiment of an example apparatus according to one embodiment of the present invention.

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

SCODA based transport is a general technique for moving particles through a medium by applying a time-varying driving field to induce periodic motion of the particles and superimposing on this driving field a time-varying perturbing field that periodically alters the drag (or equivalently the mobility) of the particles in the medium (i.e. a mobility-altering field). Application of the mobility-altering field is coordinated with application of the driving field such that the particles will move further in a desired direction during one part of the SCODA cycle than in other parts of the SCODA cycle. The application of the driving field and the application of the mobility altering field are correlated so that the mobility altering field acts to maximize mobility of the particles at a given location at the same time that the driving field moves the particles located near the given location in a desired direction.

The driving field and the mobility altering field can be selected depending on the characteristics of the particles to be separated. Examples of potentially suitable driving fields include electric fields, magnetic fields, flow rates, density gradients, gravitational or acceleration fields, or the like, for example as described in PCT publication No. WO 2005/072854 which is incorporated by reference herein for all purposes. Examples of potentially suitable mobility altering fields include electric fields, temperature, light or other radiation, magnetic fields, acoustic signals, changing concentration of a species, electroosmotic effects, salt concentrations, pH, cyclical chemical changes, cyclically binding and unbinding particles, hydrostatic pressure, varying physical dimensions of the medium, or the like, as described in WO 2005/072854.

As used herein, the term "cycle" means the application to a separation medium of each possible combination of orientations and/or magnitudes of driving field and mobility altering field one time. Each such combination of orientations and/or magnitudes of driving field and mobility altering field is referred to herein as a "configuration". The term "period" means the time that it takes to complete one cycle.

In an embodiment, the apparatus includes at least three electrodes circumferentially surrounding a central reservoir with a separation medium between at least one electrode and the central reservoir. Circumferentially implies that the electrodes are located around a periphery at a distance from the central reservoir. The electrodes need not be on a circular path, nor do the electrodes have to be individually curved in shape. The electrodes must be electrically separable, so that the electrodes can be individually indexed as described below. The electrodes do not have to fill an amount of the circumferential distance and the electrodes do not have to be of the same shape. Typically, the central reservoir will contain a buffer or an additional separation medium, making it possible to recover the targeted molecules, e.g. for amplification and/or sequencing. In one arrangement, the apparatus includes arms extending outward from the central reservoir, each arm being associated with an electrode.

Embodiments of the present invention can be used to concentrate charged target particles in a collection region while limiting or preventing movement of charged target particles out of the collection region, without the need to place an electrode in the collection region. A separation apparatus with n separation arms, wherein n is at least 3, is provided. All n separation arms are in electrical contact through the collection region. Voltages are applied through the separation arms such that the electric field strength differs between at least one of the separation arms and the remaining arms. The voltage configuration is varied to produce net motion of the charged target particles in a desired direction. Conditions of electric field strength and a variable mobility altering field (which can be the electric field strength in some embodiments) are selected to produce net motion of target particles in a desired direction (i.e. either toward or away from the collection region). Contaminating particles that are not electrically charged, or that have a mobility that does not vary significantly under the application of the mobility altering field, experience little or no net motion under the influence of the electric field. In some embodiments, conditions of electric field strength and mobility altering field are selected so that a contaminating particle that is structurally similar to the target particle (e.g. a methylated form of the target particle or a particle having the same sequence as the target particle with one point mutation) experiences net motion in a direction opposite to the net motion experienced by the target particle. Particles that reach the collection region experience a restoring force upon movement into any one of the separation arms that tends to return such particles to the collection region. Thus, target particles can be collected in the collection region, without the need to provide an electrode in the collection region.

FIG. 1 shows an apparatus 30 for separating particles according to one embodiment. Apparatus 30 has three separation arms 32 disposed around a central reservoir 34. In the illustrated embodiment, separation arms 32 are symmetrically disposed around central reservoir 34. Central reservoir 34 provides the collection region in the illustrated embodiment. Separation arms 32 are spaced apart; that is, the ends of separation arms 32 do not directly contact one another, but are separated by central reservoir 34. Each one of separation arms 32 includes separation medium (shown as 136 in FIG. 4B).

As used herein with reference to separation arms 32, the term "length" refers to a direction along separation arm extending between central reservoir 34 and the distal end of separation arm 32. "Width" refers to a direction perpendicular to and in the same plane as "length".

In some embodiments, central reservoir 34 optionally includes separation medium. Removal and extraction of collected target particles is facilitated in embodiments in which central reservoir 34 is filled with buffer.

A buffer chamber 40 is provided at the distal end of each separation arm 32 (i.e. the end opposite central reservoir 34) so that an electric field can be applied to each separation arm. Each buffer chamber 40 is provided with an electrode, shown schematically as 42A, 42B and 42C, so that an electric field can be applied to each separation arm 32.

Electrically charged target particles in a sample can be injected into a separation arm 32 by applying an electric field that drives the charged target particles into the separation arm. In some embodiments, injection of electrically charged target particles is done perpendicular to the direction that particles travel within separation arm 32, so that contaminating particles are not drawn to the central reservoir 34 during sample loading. Alternatively, target particles can be injected into separation arm 32 in any suitable manner, for example via the distal ends of separation arms 32, or vertically from a reservoir positioned above separation arms 32.

In the illustrated embodiment, at least one separation arm 32 is provided with a loading reservoir 38. Loading buffer chambers 44 are provided on the sides of separation arms 32 opposite loading reservoir 38. Loading electrodes, shown schematically as 46A, are provided in each loading buffer chamber 44. Complementary loading electrodes, shown schematically as 46B, are provided in each loading reservoir 38. In use, a sample is injected into one or more separation arms 32 by loading the sample in the appropriate loading reservoir(s) 38. A suitable potential difference is applied across opposing loading electrodes 46A, 46B to inject electrically charged components of the sample into separation medium 36 within separation arms 32. For example, where the target particles are nucleic acids, which are typically negatively charged, a positive voltage is applied to electrode 46A and a negative voltage is applied to electrode 46B to inject the nucleic acids into separation arm 32.

In some embodiments, a single loading reservoir is used to load the sample into multiple separation arms 32. In such embodiments, a single electrode 46B can be used in conjunction with several electrodes 46A to load the sample.

Electrically charged particles can be loaded in any suitable manner, including from above the separation arms and/or from the distal ends of the separation arms. In the illustrated embodiment, loading buffer chambers 44 are positioned towards the distal ends of separation arms 32 (i.e. the ends of separation arms 32 away from central reservoir 34). Loading buffer chambers 44 are configured to inject electrically charged particles perpendicularly into separation arms 32 so that the paths of travel of the charged particles entering a separation arms 32 extend across the width of the separation arm 32. Injection of electrically charged particles perpendicularly into separation arms 32 as in the illustrated embodiment minimizes the risk that non-target particles will reach central reservoir 34 during the injection process.

After the sample has been injected into separation arms 32, voltages are applied to electrodes 42A, 42B and 42C to produce an electric field and cause movement of particles within separation arms 32 (i.e. to provide a driving field). The direction of the driving field in a given separation arm 32 is varied from time to time. Concurrently with the application of the driving field, but not necessarily simultaneously, a mobility altering field is applied to vary the mobility of particles within separation arms 32. The effect of the mobility altering field is varied from time to time. In some embodiments, the electric field is both the driving field and the mobility altering field.

In some embodiments, including the illustrated embodiment, the electric field that provides the driving field also provides the mobility altering field. For example, for particles that have a mobility that varies with electric field strength, e.g. nucleic acids such as DNA or RNA, the applied electric field can provide both the driving field and the mobility altering field. For example, the following voltage patterns may be applied across electrodes 42A, 42B and 42C:

TABLE 1

Exemplary voltage pattern for embodiment with three separation arms.

| Step | Electrode 42A | Electrode 42B | Electrode 42C |
|---|---|---|---|
| 1 | H | H | L |
| 2 | L | H | H |
| 3 | H | L | H |

Where "H" represents a high voltage applied to the electrode, and "L" represents a low voltage applied to the electrode. At times when the voltage applied to an electrode associated with a particular separation arm 32 is high, the electric field strength in that particular separation arm 32 will be low. In the illustrated embodiment, the current flowing through separation arm 32C in step 1 will be twice the current flowing through either one of separation arms 32A or 32B in embodiments in which all separation arms have the same impedance (i.e. the amount of current flowing through separation arm 32C must equal the sum of the amount of current flowing through separation arms 32A and 32B). Thus, the electric field strength in separation arm 32C in this high electric field strength condition will be twice the electric field strength in either of separation arms 32A or 32B. Each of steps 1, 2 and 3 represents a discrete configuration of the driving field (the electric field) and the mobility altering field (the electric field) for this exemplary embodiment. The application of each of steps 1, 2 and 3 one time represents one cycle.

In some embodiments, the high voltage may be any voltage between 100 V and 1000 V, e.g. 100 V, 125 V, 150 V, 175 V, 200 V, 225 V, 250 V, 275 V, 300 V, 325 V, 350 V, 375 V. 400 V, 425 V, 450 V. 475 V, 500 V, 525 V, 550 V. 575 V, 600 V, 625 V, 650 V, 675 V. 700 V. 725 V. 750 V. 775 V. 800 V. 825 V. 850 V. 875 V, 900 V, 925 V, 950 V. 975 V, or 1000 V and the low voltage may be any voltage lower than the high voltage. The polarity of the voltage is selected depending on the charge of the target particles (positive or negative). The low voltage is 0 V in some embodiments. The effect of applying the voltages summarized in Table 1 on a negatively charged molecule from a sample that has a mobility that varies with electric field strength, for example a nucleic acid such as DNA or RNA, is illustrated schematically in FIG. 2 and described below with reference to the movement of an exemplary polynucleotide molecule. In step 1, separation arms 32A and 32B are regions of low electric field strength. Arm 32C is a region of high electric field strength, as indicated by diagonal shading. Negatively charged particles, such as polynucleotides, in separation arms 32A and 32B will move in a direction away from central reservoir 34 by a distance $\mu_L E_L t$, where $\mu_L$ is the mobility of the particle at the low electric field strength, $E_L$ is the low electric field strength, and t is the time for which the low electric field is applied. This movement is indicated schematically by arrows 50A, 50B. This motion will coincide with the time interval during the period of the cycle in which the electric field strength is low, and in which the mobility of the polynucleotides through separation medium 36 is lower (due to the relatively low electric field strength in separation arms 32A, 32B). Thus, the distance traveled by the polynucleotides located in separation arms 32A and 32B away from central reservoir 34 will be relatively small.

In step 2, separation arms 32B and 32C are regions of low field strength, as indicated by an absence of shading, while separation arm 32A is a region of high field strength, as indicated by diagonal shading. Negatively charged particles, such as polynucleotides, in separation arm 32B will again move in a direction away from central reservoir 34, as indicated by arrow 52B. This motion will coincide with the time interval during the period of the cycle in which the electric field strength is relatively low and in which the mobility of the polynucleotides through separation medium 36 is lower (due to the low electric field strength in separation arm 32B). Thus, the distance traveled by polynucleotides in separation arm 32B ($\mu_L E_L t$) away from central reservoir 34 will be relatively small. Negatively charged particles, such as polynucleotides, in separation arm 32A will move in a direction toward central reservoir 34, as indicated by arrow 54A. This motion will coincide with the time interval during the period of the cycle in which electric field strength is high and in which the mobility of the polynucleotides through separation medium 36 is higher (due to the high electric field strength in separation arm 32A). Thus, the distance traveled by the polynucleotides in separation arm 32A toward central reservoir 34 will be relatively large, and can be described as $\mu_H E_H t$, where $\mu_H$ is the mobility of the polynucleotide particle at the high electric field strength condition, $E_H$ is the high electric field strength, and t is the time for which the high electric field strength is applied.

In step 3, separation arms 32A and 32C are regions of low field strength, while separation arm 32B is a region of high field strength. Negatively charged 30 particles, such as polynucleotides, in separation arm 32A will move in a direction away from central reservoir 34, as indicated by arrow 52A. This motion will coincide with the time interval during the period of the cycle in which the electric field strength in separation arm 32 is low and in which the mobility of the polynucleotides through separation medium 36 is lower (due to the low electric field strength in separation arm 32A). Thus, the distance traveled by polynucleotides in separation arm 32A ($\mu_L E_L t$) in a direction away from central reservoir 34 will be relatively small. Negatively charged particles, such as polynucleotides, in separation arm 32B will move in a direction toward central reservoir 34, as indicated schematically by arrow 54B. This motion will coincide with the time interval during the period of the cycle in which the electric field strength is high and in which the mobility of the polynucleotides through separation medium 36 is higher (due to the high electric field strength in separation arm 32B). Thus, the distance traveled by the polynucleotides in separation arm 32B ($\mu_H E_H t$) toward central reservoir 34 will be relatively large.

In this example, negatively charged particles that do not have a mobility that varies with electric field strength, or that does not vary significantly with electric field strength (i.e. for which $\mu_L$ is equal or similar to $\mu_H$) will tend to experience zero net motion towards or away from central reservoir 34, because the times and electric field strengths have been selected such that the magnitude of the steps taken away from central reservoir 34 by such particles as represented, for example, by arrows 50A and 52A will tend to be equal or nearly equal to the magnitude of the steps taken towards central reservoir 34 by such particles, as represented, for example, by arrow 54A. That is, because the electric field strength at times of low electric field strength is ½ the electric field strength at times of high electric field strength, and because the particle experiences the low electric field strength for twice the length of time as the high electric field strength, the net motion of the particle will tend to be zero or close to zero.

Steps 1, 2 and 3 can be repeated to effect net motion of target particles that have a mobility that varies with electric field strength within separation arms 32. In some embodiments, operating conditions including the electric field strength and the length of time the electric field is applied are selected so that the motion of target particles toward central reservoir 34 during times of high electric field strength (illustrated as arrows 54A, 54B) is greater than twice as large as the total motion away from central reservoir 34 during times of low electric field strength during one cycle (illustrated as arrows 50A, 50B and 52A, 52B). That is, the average distance traveled by the target particles during all times of low electric field strength in one cycle is less than the average distance traveled by the target particles during times of high electric field strength in one cycle. In this manner, target particles can be concentrated in central reservoir 34 if the polarity of the applied voltage is selected appropriately. In the described exemplary embodiment, particles that have a mobility that varies with electric field strength (e.g. polynucleotides) can be separated from particles that have a mobility that does not vary with electric field strength, or which varies to a lesser extent with electric field strength (e.g. proteins).

Figure 2:
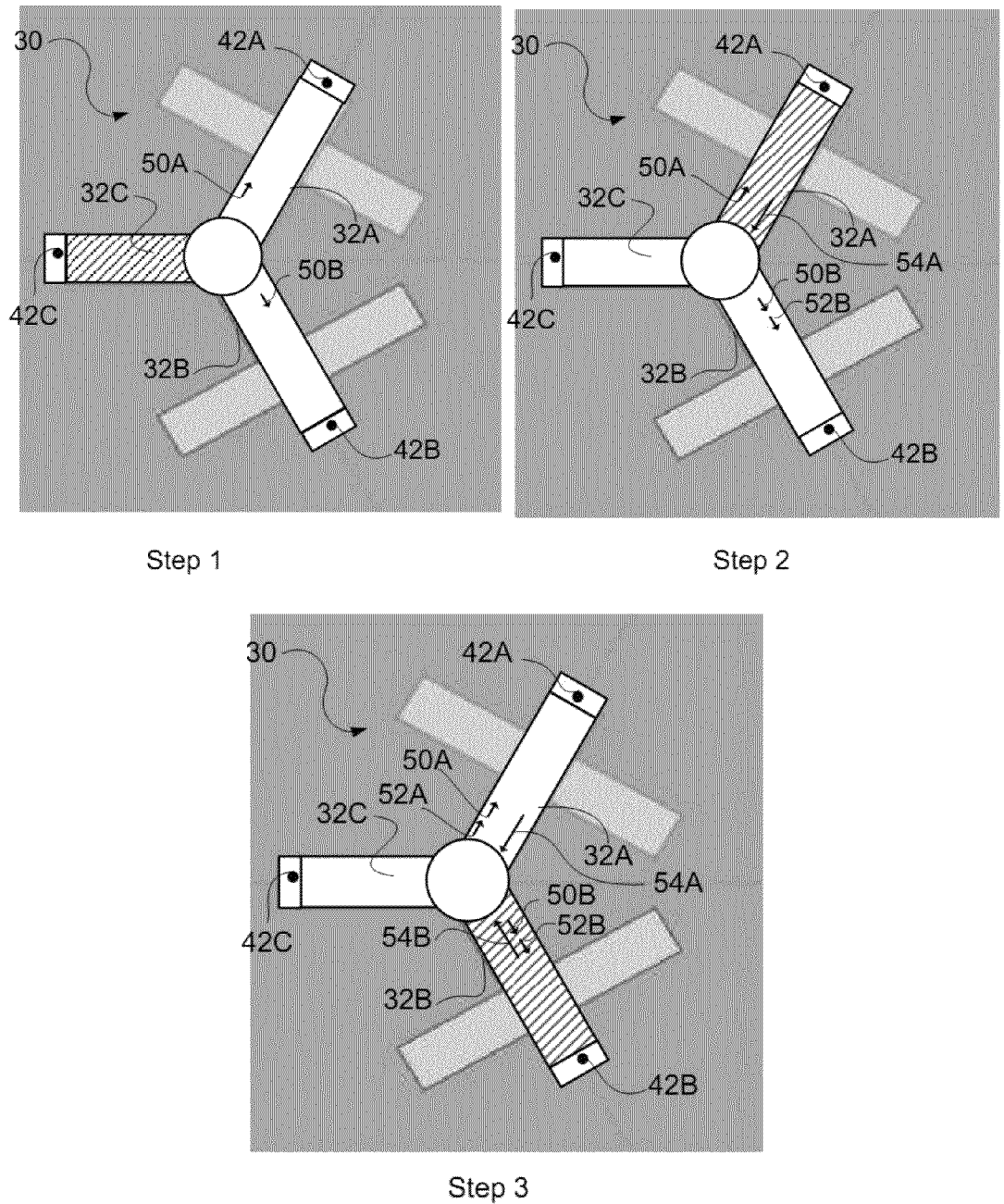
FIG. 2 shows the movement of a hypothetical particle under applied electric fields in an exemplary embodiment.

It is not necessary that the electric field pattern be rotated as described above with respect to steps 1, 2 and 3 as illustrated in FIG. 2. For example, the electric field pattern could be applied using random or occasionally varying combinations of the configuration of steps 1, 2 and 3. As long as the electric field pattern is such that the electric field in each separation arm containing target particles to be separated spends approximately ⅓ of the time in the high electric field strength configuration and approximately ⅔ of the time in a low electric field strength configuration, the net motion of the target particles will be towards central reservoir 34. Similarly, in an embodiment having n separation arms as described below, net motion of target particles towards central reservoir 34 can be effected in each one of the separation arms if the electric field pattern in that separation arm spends, on average, approximately 1/n of the time in the high electric field strength configuration and approximately (n−1)/n of the time in the low electric field strength configuration.

Apparatus 30 could be provided with any desired number n of separation arms 32, where n is greater than or equal to 3. For example, in some embodiments, apparatus 30 has 4, 5, 6, 7, 8, 9, 10, 11 or 12 separation arms 32. At least three separation arms are required so that the electric field strength can be varied as described above.

In embodiments where there are three or more separation arms and central reservoir 34 contains buffer, particles that enter central reservoir 34 will experience a net restoring force towards the separation arm that they came from (because the mobility of the particles will not vary within the buffer contained in central reservoir 34) and will tend to collect at the interface between the separation arm and central reservoir 34. The number of separation arms to be used in a particular embodiment would be determined by one skilled in the art depending on the nature of the particles to be separated using apparatus 30. The voltage patterns applied to such an apparatus would be similar. For example, Table 2 illustrates an exemplary voltage pattern that could be applied to an apparatus having six separation arms 32. In the exemplary embodiment, one separation arm is at a high electric field strength and the remaining (n−1) separation arms are at a low electric field strength in each cycle, similar to the embodiment described above.

TABLE 2

Exemplary voltage pattern for embodiment with six separation arms, each having one electrode, identified below as A, B, C, D, E or F.

| Step | Electrode | | | | | |
|---|---|---|---|---|---|---|
| | A | B | C | D | E | F |
| 1 | H | H | L | H | H | H |
| 2 | H | H | H | L | H | H |
| 3 | H | H | H | H | L | H |
| 4 | H | H | H | H | H | L |
| 5 | L | H | H | H | H | H |
| 6 | H | L | H | H | H | H |

Providing a larger number of separation arms 32 can increase the significance of the electric field dependence of the net motion of particles within separation arms 32. That is, the magnitude of the difference between the electric field strength at the high electric field strength condition versus at the low electric field strength condition will be greater in embodiments having a larger number of separation arms 32. Particles that have a mobility in medium 36 that is highly dependent on electric field strength will tend to move a relatively larger amount in the direction of arrows 54A, 54B under conditions of higher field strength. Also, a greater number of steps in the direction of arrows 50A, 50B and 52A, 52B will be taken. Specifically, particles will take n−1 steps in the direction away from central reservoir 34, where n is the number of separation arms 32, for each step taken toward central reservoir 34.

In contrast, providing a smaller number of separation arms 32, e.g. three separation arms as shown in the illustrated embodiment, will decrease the significance of the electric field dependence of a particle's mobility on the net movement of that particle within separation arms 32. In some embodiments, for example those that exploit a binding interaction between the target particle and the medium assist in or effect separation, and/or those embodiments in which a field other than electric field strength (e.g. temperature, light, pH or salt concentration) is used as the mobility altering field, decreasing the significance of the electric field dependence of a particle's mobility on the net movement of that particle as aforesaid enhances separation of such target particles from other similar particles that share a similar electric field dependence of mobility (e.g. oligonucleotides of a similar length).

While the exemplary embodiments have been described above with reference to one separation arm having a high electric field strength while the remaining (n−1) separation arms have a low electric field strength, alternative embodiments could provide a high electric field strength in more than one separation arm at a time. For example, in the exemplary embodiment having six separation arms, two separation arms could be provided with a high electric field strength and four separation arms provided with a low electric field strength and the electric field pattern could be rotated.

Separation arms 32 need not be symmetrically disposed as illustrated. Separation arms 32 need not be generally rectangular in shape as illustrated. Separation arms 32 need not extend in straight lines as illustrated. A symmetrical arrangement of separation arms can help to provide a uniform electric field strength in each of the separation arms. Configurations of apparatus 30, including separation arms 32 and central reservoir 34, that interfere appreciably with the uniform flow of electric current through each separation arm 32 should be avoided if maximum efficiency is desired.

Separation arms 32A, 32B and 32C need not all have the same shape as one another as illustrated. For example, the widths, lengths and/or shape of separation arms 32 could be varied relative to one another, provided that the overall volume and geometry is such that the electric fields are matched in each separation arm 32. Where the separation arms will be loaded with particles to be separated, the configuration of the separation arms should be selected so that the driving and mobility altering fields will be consistent across all configurations of a cycle. For example, in embodiments in which the electric field is both the driving field and the mobility altering field, the geometry of each separation arm and the applied voltage should be selected so that the field strength is consistent across any given cross section of the width of each separation arm loaded with sample for each configuration of the electric field. In embodiments in which the electric field is the driving field and Joule heating is used to generate heat so that temperature is used in whole or in part as the mobility altering field, the geometry of each separation arm and the applied voltage should be selected so that the temperature and electric field strength are consistent across any given cross-section of the width of each separation arm loaded with sample for each configuration of the electric field, and so that equilibrium points are avoided. If a particular separation arm will not be loaded with particles to be separated, that particular separation arm can have any desired geometry. In some such embodiments, the impedance of that particular separation arm is approximately the same as the impedance of the other separation arms to avoid creation of a bias.

Figure 3A:
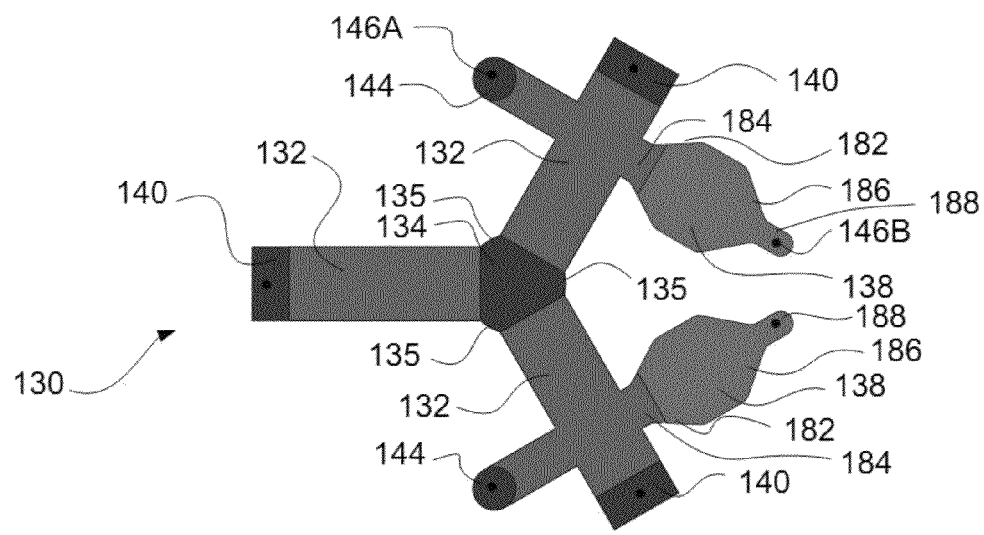
FIG. 3A is a top view showing schematically the configuration of a separation medium according to another embodiment.
Figure 3B:
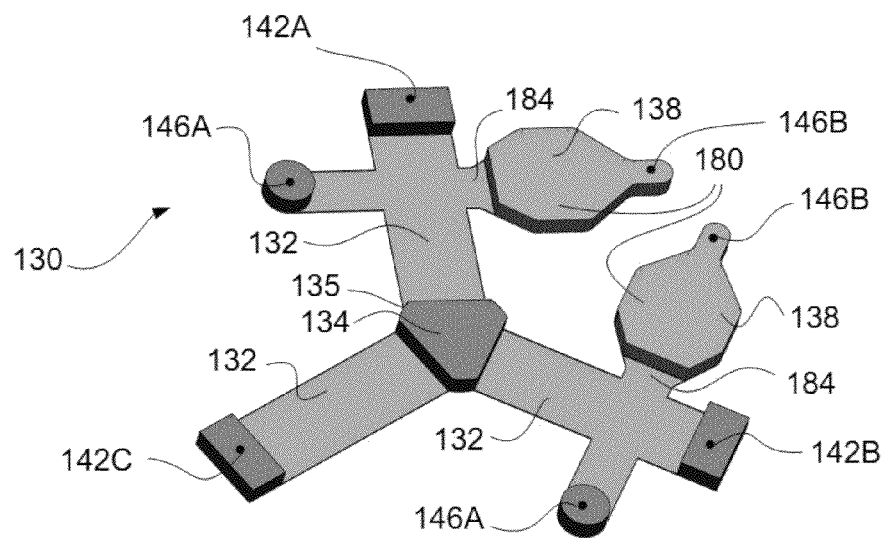
FIG. 3B is a perspective view of the separation medium of FIG. 3A.
Figure 3C:
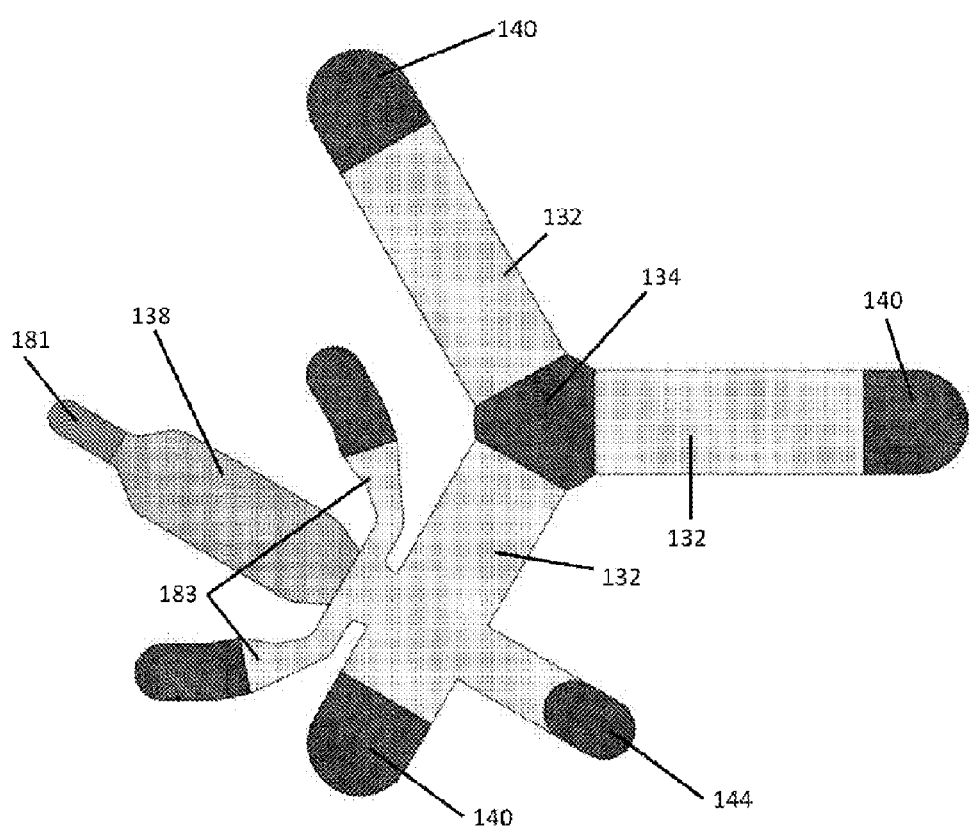
FIG. 3C is a top view of an alternate embodiment of FIG. 3A having streamlines that help constrain the sample during injection.
Figure 4A:
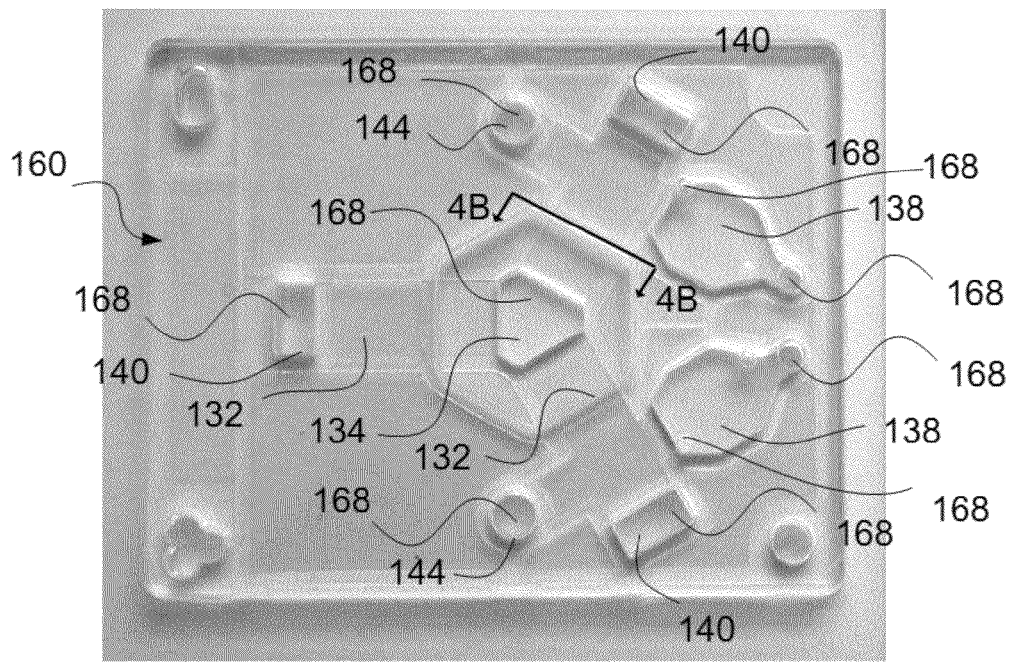
FIG. 4A is a top view of a photograph of a gel cassette for use with the apparatus of FIGS. 3A and 3B.
Figure 4B:
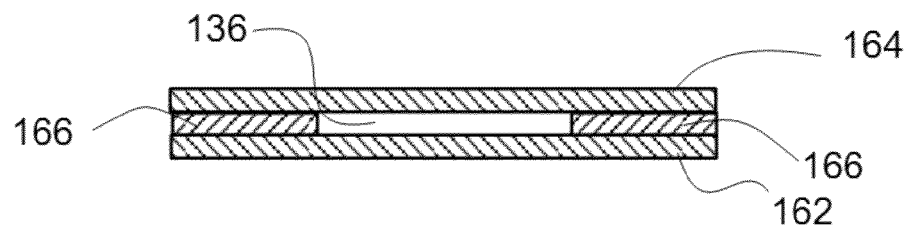
FIG. 4B is a schematic cross-sectional drawing of the cassette of FIG. 4A.
Figure 5A:
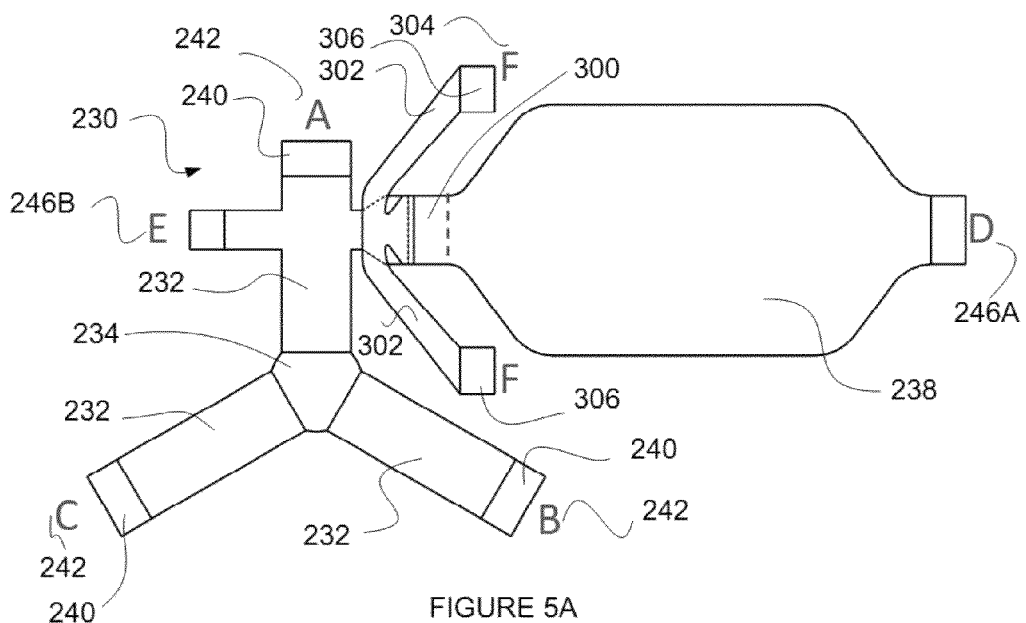
FIGS. 5A, 5B, 5C and 5D illustrate a further embodiment of an example apparatus for separating particles with a sample loading interface including a filter gel and a sample loading interface wherein two Peltier elements are provided to independently control the temperature of regions of the sample loading interface and separation arm.
Figure 5B:
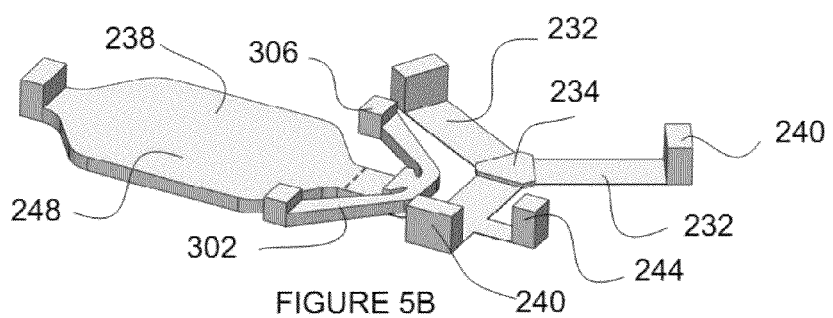
Figure 5C:
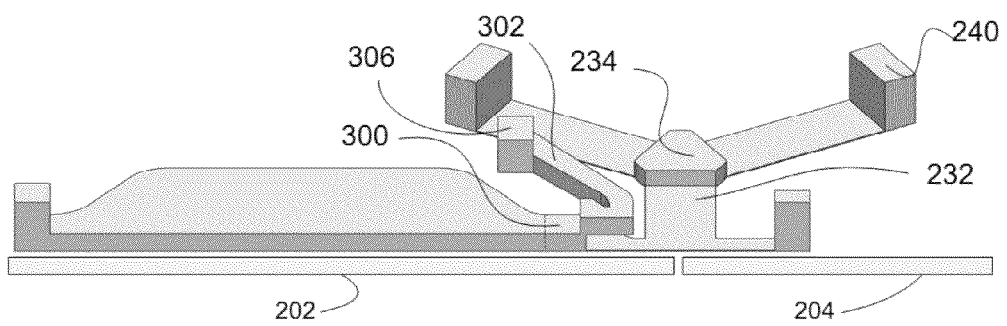
Figure 5D:
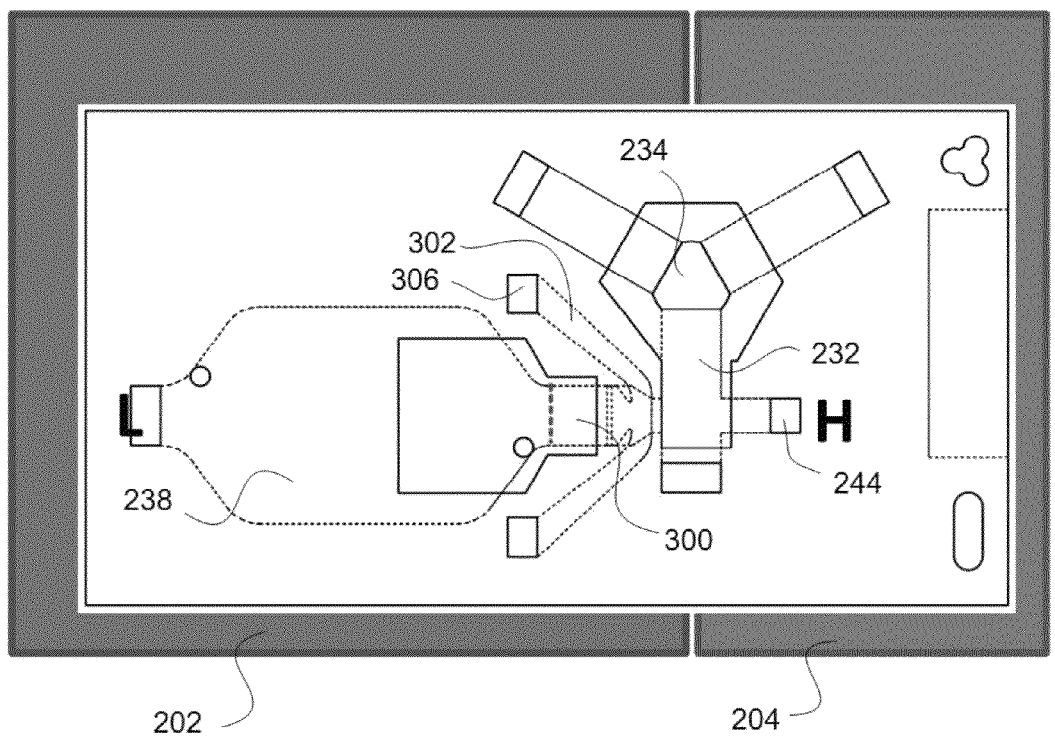

FIGS. 3A-3C illustrate a second exemplary embodiment of an apparatus 130 for separating particles. Portions of apparatus 130 that correspond in function to portions of apparatus 30 are indicated with like reference numerals incremented by 100. In the illustrated embodiment, separation arms 132 are disposed between a base plate 162 and a top plate 164 (FIG. 4). Access apertures 168 (FIG. 4A) define portions of central reservoir 134, loading reservoirs 138, and buffer chambers 140 and 144. The depths of central reservoir 134, loading reservoirs 138, and buffer chambers 140 and 144 is thus defined in part by the thickness of top plate 164 (FIG. 4B). In the illustrated embodiment, central reservoir 134, loading reservoirs 138, and buffer chambers 140 and 144 are all deeper than the thickness of separation medium 136 (FIG. 4B).

In the illustrated embodiment, central reservoir 134 is of a generally triangular shape, with rounded or trimmed corners 135. Central reservoir 134 is shaped to minimize any potential distortions to the electric field used to move sample particles in arms 132.

In the illustrated embodiment of FIGS. 3A and 3B, loading reservoir 138 has a relatively wider middle portion 180. However, loading reservoir 138 can be of the same width as separation arms 132, as shown in FIG. 3C. In FIGS. 3A and 3BA, tapered portion 182 narrows from middle portion 180 toward an injection surface 184 on separation arm 132. A second tapered portion 186 narrows from middle portion 180 toward an electrode chamber 188 for receiving a loading electrode, shown schematically as 146B. A separate loading buffer chamber 144 receives loading electrode 146A.

In some embodiments, loading of sample into the separation arms is enhanced. For example, in the embodiment illustrated in FIGS. 3A and 3B, loading reservoir 138 has a greater depth than the thickness of separation medium 136. Providing a loading reservoir 138 with a height greater than the thickness of separation medium 136 allows the sample volume to be increased, without making the surface area required for loading reservoir 138 unduly large. In other embodiments, as depicted in FIG. 3C, sample loading can be enhanced with the inclusion of electrical streamlines 183. Electrical streamlines 183 are in the same plane as the gel of separation arms 132, and help constrain the sample to a narrow physical window during injection. When used, a voltage is applied from the agarose dam 181 and electrical streamlines 183 to the electrode across the separation arm 132. When used to load nucleic acids, for example, the configuration in FIG. 3C reduces loading losses due to nucleic acid spreading upon injection. Such techniques are especially useful when evaluating high value samples, such as forensic crime samples, where any nucleic acid loss can skew the results.

With reference to FIGS. 4A and 4B, in one embodiment a cassette 160 for use with apparatus 130 has a base plate 162 and a top plate 164. Plates 162, 164 may be made of any suitable non-electrically-conductive material, for example plastic, acrylic or glass. In embodiments in which temperature is used as the mobility altering field, at least one of base plate 162 and top plate 164 should be made from a material with good thermal conductivity, for example, glass.

Base plate 162 may be secured to top plate 164 in any suitable manner, for example by being integrally formed therewith, clamped thereto, secured thereto with an acceptable adhesive, or the like. In the illustrated embodiment of FIGS. 4A and 4B, base plate 162 is secured to top plate 164 using a layer of pressure sensitive adhesive 166. Pressure sensitive adhesive 166 maintains the spacing between base plate 162 and top plate 164. Pressure sensitive adhesive is cut to provide the desired configuration of separation medium 136. That is, portions of pressure sensitive adhesive 166 are removed where pressure sensitive adhesive 166 would otherwise interfere with separation arms 132, central reservoir 134, loading reservoir 138, electrode buffer chambers 140, loading buffer chambers 144, or the like. For example, where the separation medium is a gel such as polyacrylamide or agarose, pressure sensitive adhesive 166 can be cut to the desired shape, bonded between base plate 162 and top plate 164, and the gel can be poured in each separation arm 132. Where the separation medium is relatively thin, e.g. 100 μm, capillary action will draw the gel between plates 162, 164, and the gel will take on the shape defined by pressure sensitive adhesive 166. Access apertures 168 are provided in the top plate to provide access to loading reservoirs 138, central reservoir 134, to enable electrodes 140, 142, 146 to be inserted into the corresponding buffer chambers. In embodiments in which the gel is sufficiently thick that capillary action will not prevent the gel from entering loading reservoirs 138, central reservoir 134, electrode buffer chambers 140 or loading buffer chambers 144, suitable gel dams or other structures can be used to prevent the gel from flowing into these regions when being poured.

In the illustrated embodiment, the thickness of separation medium 136 is defined by the thickness of the layer of pressure sensitive adhesive 166. Separation medium 136 may have any desired thickness. In some exemplary embodiments, separation medium 136 is 100 μm thick. The thickness of separation medium 136 could be increased to increase the sample capacity of cassette 160. However, if separation medium 136 is made too thick, separation medium 136 will take longer to heat and cool (i.e. the thermal response time of separation medium 136 will be increased), which may be undesirable in some embodiments that use temperature as the mobility altering field. The thermal relaxation time of a separation arm filled with separation medium approximately 100 μm thick has been found to be on the order of ~200 ms in one exemplary embodiment. If separation medium 136 is made too thin, the capacity of cassette 160 may become undesirably low. The capacity of cassette 160 is determined by the volume of a sample to be loaded, the mass of charged target particle (e.g. DNA) to be loaded, and the concentration of electrically charged species (including salts) in the sample.

In some embodiments, a filter gel can be used upstream of a separation medium to reduce the level of contaminants present in a sample before target particles are subjected to separation, as well as to increase the capacity of the separation medium. The capacity of an apparatus can depend on all of the volume and salinity of a sample and the amount of charged target and contaminant particles present in a sample. That is, the capacity of an apparatus may be limited by any of the volume of a sample (a sample which is too large in volume may not be loaded), the salinity of a sample (i.e. the presence of too many ions may interfere with electrophoresis if the salinity of the sample is too high), or the amount of target particle in a sample (e.g. the presence of too much nucleic acid in the sample, whether target or contaminating sequence, may interfere with electrophoresis). A filter gel as described below allows for a larger volume of sample to be loaded, allows for the removal of excess ions in the sample during loading, and/or allows for the removal of particles similar in nature to the target particle but which do not interact as strongly with the immobilized affinity agent in the filter gel (e.g. for the removal of nucleic acids that have a sequence that is not similar to a target nucleic acid). In use, a filter gel can be positioned upstream of the separation apparatus, so that particles can be first loaded into the separation gel, and then loaded onto the separation apparatus.

A filter gel is a separation medium (for example agarose or polyacrylamide gel) that has an affinity agent immobilized therein. The affinity agent is selected to have a binding affinity for target particles of interest (e.g. oligonucleotides having a particular sequence). A sample is injected into the filter gel by application of an electric field under conditions such that the target particles of interest bind to the immobilized affinity agent (or alternatively the sample could be mixed with the filter gel when the filter gel is poured). Under the influence of the electric field, contaminating particles that do not bind to the affinity agent pass through the filter gel. In some embodiments, the contaminating particles can be removed via an exhaust gel downstream of the filter gel during sample loading, so that contaminating particles do not enter the separation medium.

After contaminating particles have passed through the filter, conditions are changed so that the target particles do not bind the affinity agent (e.g. the temperature is raised), and an electric field is applied to inject the target particles from the filter gel into the separation medium. A filter gel can be used together with any apparatus for conducting electrophoresis to reduce the level of contaminants present and/or to increase the capacity of the apparatus. For example, a filter gel could be provided upstream of a conventional electrophoresis gel used to separate oligonucleotides based on size.

FIGS. 5A, 5B, 5C and 5D illustrate a third exemplary embodiment of an apparatus 230 for separating particles. Portions of apparatus 230 that correspond in function to portions of apparatus 30 are identified by like reference numerals incremented by 200. In the illustrated embodiment, loading reservoir 238 is thicker than the separation medium in separation arms 232. A filter gel 300 is provided at the end of loading reservoir 238 adjacent separation arm 232 (the edge of the filter gel 300 is indicated by a dashed line). Filter gel 300 includes a plurality of immobilized affinity agents that bind to target particles in sample 248. In some embodiments, the plurality of immobilized affinity agents are all the same affinity agent. During injection of sample 248 into separation arm 232, target particles can be bound to the immobilized affinity agents in filter gel 300 while contaminating particles are washed through filter gel 300. After sample 248 has been loaded, target particles can then be eluted for injection into separation arm 232 in any suitable manner In some embodiments, target particles are bound to the immobilized affinity agents in filter gel 300 at a relatively low temperature, and the target particles are eluted by increasing the temperature to a level where the target particles do not bind significantly to the immobilized affinity agents. In some embodiments, separation arm 232 includes the same affinity agent as filter gel 300. In some embodiments, separation arm 232 includes a different affinity agent than filter gel 300. In some embodiments, the affinity agent in filter gel 300 has a stronger binding affinity for both the target particle and non-target particles than the affinity agent in separation arms 232. In some embodiments, separation arm 232 does not include an affinity agent, while filter gel 300 does include an affinity agent.

In some embodiments, temperature regulators such as heating and/or cooling units are provided adjacent to the medium to facilitate temperature control. In some embodiments, one or more Peltier elements are provided to adjust the temperature of the separation medium. In some such embodiments, the Peltier elements are positioned adjacent to the base plate (e.g. base plate 162) and the base plate is made from a thermally conductive material, e.g. glass. In some embodiments, a controller is provided to regulate the operation of the Peltier elements and/or the electrodes. Peltier elements can be used to heat and/or cool the separation medium, depending on the desired application.

In some embodiments, including the illustrated embodiment of FIGS. 5A, 5B, 5C and 5D, two Peltier elements 202, 204 (shown only in FIGS. 5C and 5D) are provided adjacent separation arm 232 and filter gel 300, beneath the base plate of the gel cassette (not shown). Peltier elements 202, 204 are independently operable; that is, the temperature of each of Peltier elements 202 and 204 can be separately controlled. In some embodiments, a controller is provided to control the operation of Peltier elements 202, 204 and/or electrodes 242, 304 and/or 246A/246B (the electrodes are schematically labeled as the letters A, B and C (electrodes 242), F (304), D (246A) and E (246B) in FIG. 5A). In some embodiments, including the illustrated embodiment, Peltier elements 202, 204 abut one another within (in the illustrated embodiment, at approximately the midpoint of) the width of separation arm 232. To inject sample 248 into separation arm 232, an electric field is applied across loading electrodes 246A and 246B (or, as described below, electrodes 246A and 304) Initially, the temperature of Peltier element 202, which is adjacent filter gel 300, is maintained at a low temperature at which the target particle binds strongly to the immobilized affinity agent (e.g. a temperature below the melting temperature of the target particle-affinity agent duplex). Contaminating particles do not bind to the immobilized affinity agent, or bind the immobilized affinity agent to a lesser extent than the target particles. Consequently, contaminating particles can be washed through the filter gel 300, while the target particles are stacked at approximately the interface between loading reservoir 238 and filter gel 300. This step can be described as "filter injection".

After sample 248 has been loaded on filter gel 300, the temperature of Peltier element 202 can be increased to a level at which the target particles bind poorly or not at all to the immobilized affinity agent (e.g. a temperature above the melting temperature of the target particle-affinity agent duplex). Continued application of an electric field across loading electrodes 246A and 246B will cause the target particles to be injected into separation arm 232. This step can be described as "hot injection" of the target particles.

In some embodiments, including the illustrated embodiment, separation arm 232 also includes an immobilized affinity agent that binds to the target particles. Target particles can be stacked in the separation medium prior to the application of electric fields to separate the particles by providing a temperature gradient in the path of travel of particles entering the separation medium. For example, a temperature profile can be created across the width of the separation arm, such that target particles entering the separation medium from the filter gel are at a high temperature at which the target particles bind poorly or not at all to the immobilized affinity agent, while a point within the path of travel of the target particles entering the separation arm downstream of the filter gel is at a relatively low temperature at which the target particles are likely to remain bound to the immobilized affinity agent. Target particles will tend to bind to the immobilized affinity agent at the point where the temperature drops, thereby stacking the target particles within the separation medium.

For example, in the illustrated embodiment, a second Peltier element 204 is provided adjacent separation arm 232 and in the path of travel of particles being injected into separation arm 232. Peltier elements 202 and 204 are positioned so that the interface between the two elements is at a convenient location relative to the width of separation arm 232. In some embodiments, the interface between Peltier elements 202 and 204 is located at approximately the midpoint of the width of separation arm 232. Peltier elements 202 and 204 can be spaced apart. In some embodiments, Peltier elements 202 and 204 are positioned close together, so that target particles can be stacked in a narrow band as described below.

Stacking of target particles within separation arm 232 may be done by filter injection of the target particles in filter gel 300 as described above, followed by hot injection of the target particles into separation arm 232 by increasing the temperature of Peltier element 202. During the hot injection step, the temperature of Peltier element 204 is maintained at a low temperature at which the target particles bind effectively to the immobilized affinity agent in separation arm 232 (e.g. at a temperature below the melting temperature of the target particle-affinity agent duplex). After the target particles have been stacked in separation arm 232, the temperature of Peltier element 202 can be reduced and the temperature of Peltier element 204 can be increased so that the temperature of both elements 202 and 204 is approximately the same, and is at a level at which the electric fields are to be applied to electrodes 242 (represented by the letters A, B and C in FIG. 5A).

In some embodiments, loading reservoir 238 includes exhaust arms 302, as in the illustrated embodiment of FIGS. 5A, 5B, 5C and 5D. The exhaust arms are provided to receive contaminants flowing through the filter gel during sample loading. Exhaust arms allow contaminants to be removed from the sample and from the filter gel without allowing the contaminants to enter the separation medium. By applying an electric field across both the filter gel and the exhaust arms, contaminants that do not bind to the immobilized affinity agent within the filter gel can be removed, without contaminating the separation medium.

In some embodiments, exhaust arms 302 are filled with the same gel as filter 300. In some embodiments, the gel filling exhaust arms 302 includes an immobilized affinity agent therein. Exhaust arms 302 are coupled to a loading electrode 304 (represented schematically as the letter F in FIG. 5A) which sits in a loading electrode buffer chamber 306. In the illustrated embodiment, two exhaust arms 302 extend outwardly from filter gel 300. Exhaust arms 302 can be provided with any desired configuration. In some embodiments, exhaust arms 302 can conveniently extend out of the plane of the separation medium to remove contaminant particles.

In the illustrated embodiment, exhaust arms 302 contact filter gel 300 at a point vertically above the surface of loading reservoir 238. In this way, an electric field can be applied between electrodes 246A and 304 to remove contaminants during stacking of target particles in filter gel 300. Such contaminants do not enter separation arm 232, as the contaminants pass through exhaust arms 302 to buffer chamber 306.

Figure 6:
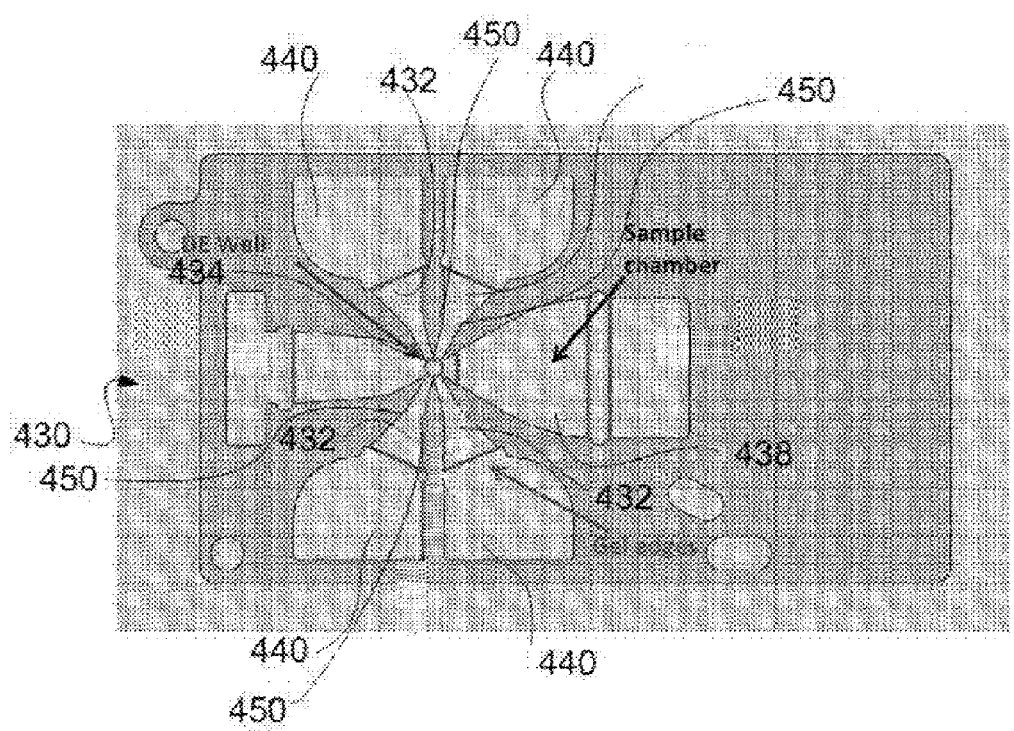
FIG. 6 is a top view of a further embodiment of an example apparatus for separating particles having four tapered separation arms.

FIG. 6 shows a further embodiment of an example apparatus 430 for separating particles. Portions of apparatus 430 that correspond in function to portions of apparatus 30 are indicated by like reference numerals incremented by 400. Apparatus 430 has four separation arms 432. The separation arms 432 of apparatus 430 are tapered, that is, the width of separation arms 432 at a point proximate central reservoir 434 is narrower than the width of separation arms 432 at a point distal from central reservoir 434. By varying the width of separation arms 432 along their length, the magnitude of current density at any given point along the length of separation arms 432 can be varied. That is, due to conservation of electric charge, the amount of charge passing through a cross-section taken at any point along the length of separation arm 432 must be the same as the amount of charge passing through a cross-section taken at any other point along the length of separation arm 432. Thus, the amount of current passing through a cross-section at which separation arm 432 is relatively narrower will be larger than the amount of current passing through a cross-section at which separation arm 432 is relatively wider. The temperature within the separation medium can be varied based on the amount of current passing through a cross-section at a particular point within the separation arm 432.

In some embodiments, including the illustrated embodiment, the tapered separation arms 432 have a point at which the angle of taper outwardly from a center line running along the length of the separation arms increases slightly, indicated at 450. The presence of a point or region 450 at which the angle of taper changes can help to enhance the effects of changes in temperature and electric field strength, resulting in a sharper separation of particles.

The creation of varying electric field strengths or temperatures within the tapered separation arms 432 allows for the creation of equilibrium points for particles with certain characteristics within separation arms 432. For example, for particles that have a mobility that varies with both electric field strength and temperature, by selection of appropriate conditions, at a certain point along the length of separation arms 432, the net motion of a target particle in one cycle can change from net negative (i.e. away from central reservoir 434) to net positive (i.e. toward central reservoir 434). The target particle will tend to remain at that equilibrium point within separation arm 432. After other particles have been moved out of separation arms 432, the operating conditions can be adjusted so that the target particle experiences net positive motion towards central reservoir 434. Target particles can then be removed from central reservoir 434 and subjected to further analysis.

For example, the illustrated embodiment of FIG. 6 can be used to separate oligonucleotides such as DNA based on size. The oligonucleotides can be loaded on the separation arms 432 using sample chamber 438 by injecting oligonucleotides through central reservoir 434 by the application of an electric field. The mobility of DNA through the separation medium varies with both temperature and electric field strength. The temperature dependence and electric field strength dependence of the mobility of larger DNA particles are both greater than the temperature dependence and electric field strength dependence of the mobility of shorter DNA particles. These differences can be used to separate DNA based on length.

Electric fields can be applied to cause net movement of the DNA in a selected direction based on the change in mobility of the DNA with changes in electric field strength. For example, the DNA can be caused to move inwardly by the application of a high positive voltage to three electrodes positioned at the distal ends of the separation arms and a low voltage to the fourth electrode positioned at the distal end of the separation arm) in the manner described above. Such electric fields can be termed focusing fields (because DNA tends to be focused in to central reservoir 434). The DNA can alternatively be caused to move outwardly by the application of a high positive voltage to one electrode and a low voltage to the remaining three electrodes at the distal end of the separation arms. Such electric fields can be termed defocusing fields (because the DNA tends to move outwardly, away from central reservoir 434).

Application of the electric fields also causes a change in temperature of the separation medium. Because the separation arms have a tapered shape, a larger amount of current will pass through a cross section of the separation arm taken nearer to the central reservoir 434 than farther away from the central reservoir 434. Consequently, the amplitude and phase of the thermal oscillations established by the application of the electric fields change along the length of the separation arms. Because DNA mobility also depends on both temperature and electric field strength, the net movement of the DNA along the length of the separation arm will depend on the relative dominance of changes in mobility in response to temperature oscillations within the separation medium versus changes in mobility in response to changes in electric field strength. When applying defocusing fields, if conditions are chosen so that the phase of the thermal oscillations is out of phase with the defocusing electric fields towards the distal portion of the separation arms (e.g. due to a high thermal lag time for the gel to be heated due to Joule heating), some molecules will reach an equilibrium position, at which net movement toward the distal end of the separation arm caused by changes in mobility due to the changes in electric field strength will be equal to net movement toward central reservoir 434 caused by changes in mobility due to changes in temperature within the separation medium. That is, the net movement due to changes in mobility caused by changes in electric field strength will be in one direction (distally away from central reservoir 434) while net movement due to changes in mobility caused by changes in temperature can be in the opposite direction (i.e. toward central reservoir 434). Conditions can be selected so that the equilibrium position for DNA having a particular size of interest is inside the separation arms, while DNA having other sizes is washed out of the distal ends of the separation arms.

In alternative embodiments, a temperature gradient can be established using heating or cooling units positioned adjacent to any shaped separation arm (e.g. a rectangularly-shaped separation arm) to create equilibrium points in a similar manner.

Mobility of a Target Particle in an Affinity Matrix

In some embodiments, temperature is used as the mobility altering field. In some such embodiments, the mobility of a particle within the separation medium is made dependent on temperature by using an immobilized affinity agent within the separation medium to provide an affinity matrix. In some such embodiments, the separation medium is an affinity matrix and temperature is used to perturb the binding interaction between one or more target particles and the affinity matrix.

In some embodiments in which temperature is used as the mobility altering field, the temperature is varied by directly heating and/or cooling desired regions of the separation medium, for example using heating or cooling units or Peltier elements disposed adjacent the separation medium or in any other suitable manner For example, heaters or thermoelectric chillers could be used to periodically heat and cool regions of the medium, radiative heating could be used to periodically heat regions of the medium, light or radiation could be applied to periodically heat regions of the medium, Joule heating using the application of an electric field to the medium could be used, or the like. In some embodiments, a controller is provided to regulate the operation of heating and/or cooling units.

In some embodiments, heating of the separation medium by Joule heating due to the passage of electric current through the separation medium is used to vary the temperature. In some embodiments, the electric field that is used to provide the driving field is also used to provide the mobility varying temperature field. In such embodiments, regions of higher electric field strength will develop a higher temperature than regions of lower electric field strength. The heat (Q) developed in the separation medium by Joule heating will depend on both the electrical resistance (R) of the separation medium and the current (I) according to Joule's first law:

$$Q = I^2 R t \quad [1]$$

where t is the time that the current is applied.

The interactions between a target and immobilized probes in an affinity matrix can be described by first order reaction kinetics:

$$[T] + [P] \rightleftharpoons [T \ldots P] \quad [2]$$

Here [T] is the target, [P] the immobilized probe, [T ... P] the probe-target duplex, $k_f$ is the forward (hybridization) reaction rate, and $k_r$ the reverse (dissociation) reaction rate. Since the mobility of the target is zero while it is bound to the matrix, the effective mobility of the target will be reduced by the relative amount of target that is immobilized on the matrix:

$$\mu_{\textit{effective}} = \mu_0 \frac{[T]}{[T] + [T \ldots P]} \quad [3]$$

where $\mu_0$ is the mobility of the unbound target. Using reasonable estimates for the forward reaction rate and an immobilized probe concentration that is significantly higher than the concentration of the unbound target, it can be assumed that the time constant for hybridization should be significantly less than one second. If the period of the mobility-altering field is maintained at longer than one second, it can be assumed for the purposes of analysis that the binding kinetics are fast and equation [2] can be rewritten in terms of reaction rates:

$$k_f [T][P] = k_r [T \ldots P] \quad [4]$$

$$[T] = \frac{k_r}{k_f} \frac{[T \ldots P]}{[P]} \quad [5]$$

Inserting [5] into equation [3] and simplifying yields:

$$\mu_{\textit{effective}} = \mu_0 \frac{1}{1 + \frac{k_f}{k_r}[P]} \quad [6]$$

From [6] it can be seen that the mobility can be altered by modifying either or both of the forward and reverse reaction rates to modify the ratio of those reaction rates. Modification of the forward or reverse reaction rates can be achieved in a number of different ways, for example by one or more of adjusting the temperature, salinity, pH, concentration of denaturants, concentration of catalysts, by physically pulling duplexes apart with an external electric field, or the like. In one exemplary embodiment described in greater detail below, the mechanism for modifying the mobility of target molecules moving through an affinity matrix is control of the matrix temperature.

To facilitate analysis, it is helpful to make some simplifying assumptions. First it is assumed that there are a large number of immobilized affinity agents (or "probes") relative to target molecules. So long as this is true, even if a large fraction of the target molecules become bound to the probes the concentration of probes that are not bound to molecules of interest, [P], will not change much so [P] can be taken to be approximately constant. Also, it is assumed that the forward reaction rate $k_f$ changes much less with temperature than the reverse reaction rate. This assumption allows the analysis to be simplified by treating $k_f$ as being constant. This is not strictly true, as the forward reaction rate does depend on temperature. However, in embodiments operating at a temperature range near the duplex melting temperature the reverse reaction rate typically has an exponential dependence on temperature and the forward reaction rate typically has a weaker temperature dependence, varying by about 30% over a range of 30° C. around the melting temperature. It is additionally assumed that the target particle is free of any significant secondary structure. Although this final assumption would not always be correct, it simplifies this initial analysis. Secondary structure in the immobilized affinity agent or in the target particle can result in a temperature dependent forward reaction rate.

For analysis, the temperature dependence of the reverse reaction rate may be assumed to follow an Arrhenius model for unbinding kinetics. This assumption is justified by recent work in nanopore force spectroscopy.

$$k_r = A e^{\frac{\Delta G}{k_b T}} \quad [7]$$

Here A is an empirically derived constant, $\Delta G$ is the affinity agent-target particle binding energy, $k_b$ is the Boltzmann constant, and T the temperature. Inserting this into [6], rewriting the free energy $\Delta G$ as $\Delta H - T\Delta S$, and collecting constant terms allows the mobility to be rewritten as:

$$\mu_{\textit{effective}} = \mu_0 \frac{1}{1 + \beta e^{\frac{-\Delta H + T\Delta S}{k_b T}}} \quad [8]$$

Figure 7:
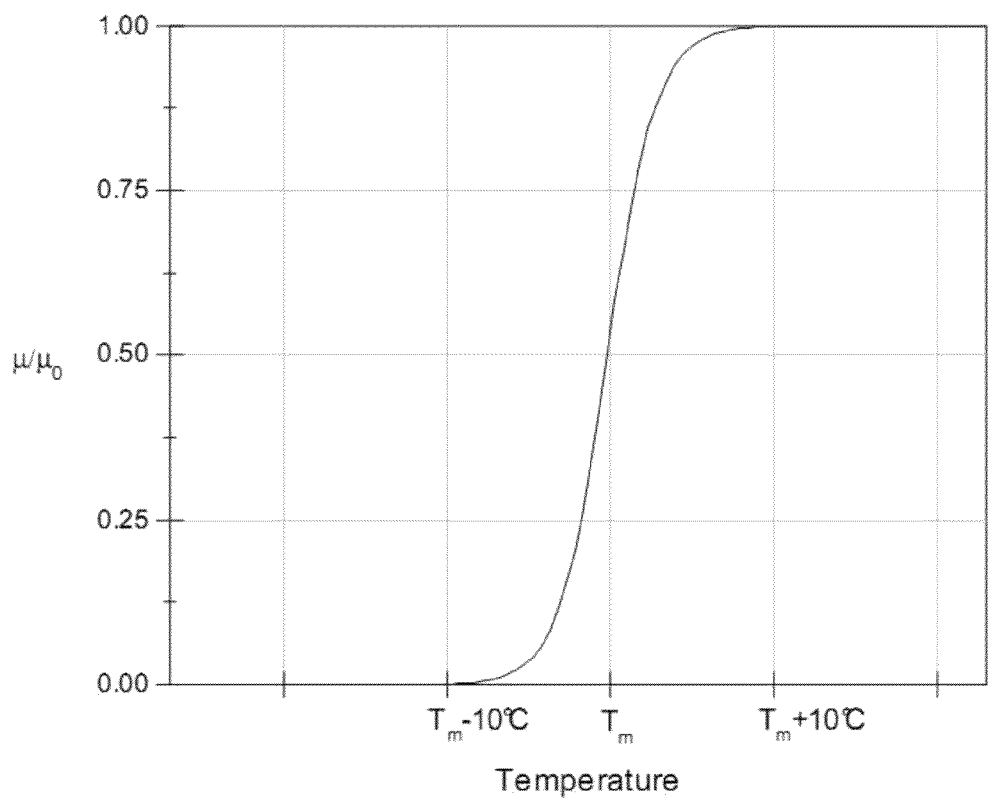
FIG. 7 is a graph illustrating the change in mobility of a particle in an affinity matrix according to one embodiment with temperature.

Equation [8] describes a sigmoidal mobility-temperature dependence, as illustrated in FIG. 7. At low temperature the mobility is nearly zero. This is the regime where thermal excitations are insufficient to unbind particles from the affinity agent. At high temperatures, where the thermal energy is greater than the binding energy, target particles move at the unbound mobility. Between these two extremes there exists a temperature range within which a small change in temperature can result in a large change in mobility.

In one exemplary embodiment, the target particle is a single stranded polynucleotide having a given sequence (the "perfect match" or "target" sequence) and a non-target particle is a single stranded polynucleotide having a sequence the same as the given sequence except for one base that is different (the "mismatch" or "background" sequence). The affinity agent is an immobilized oligonucleotide probe with a sequence complementary to the target particle, but with a one base mismatch to the mismatch particle.

Figure 8:
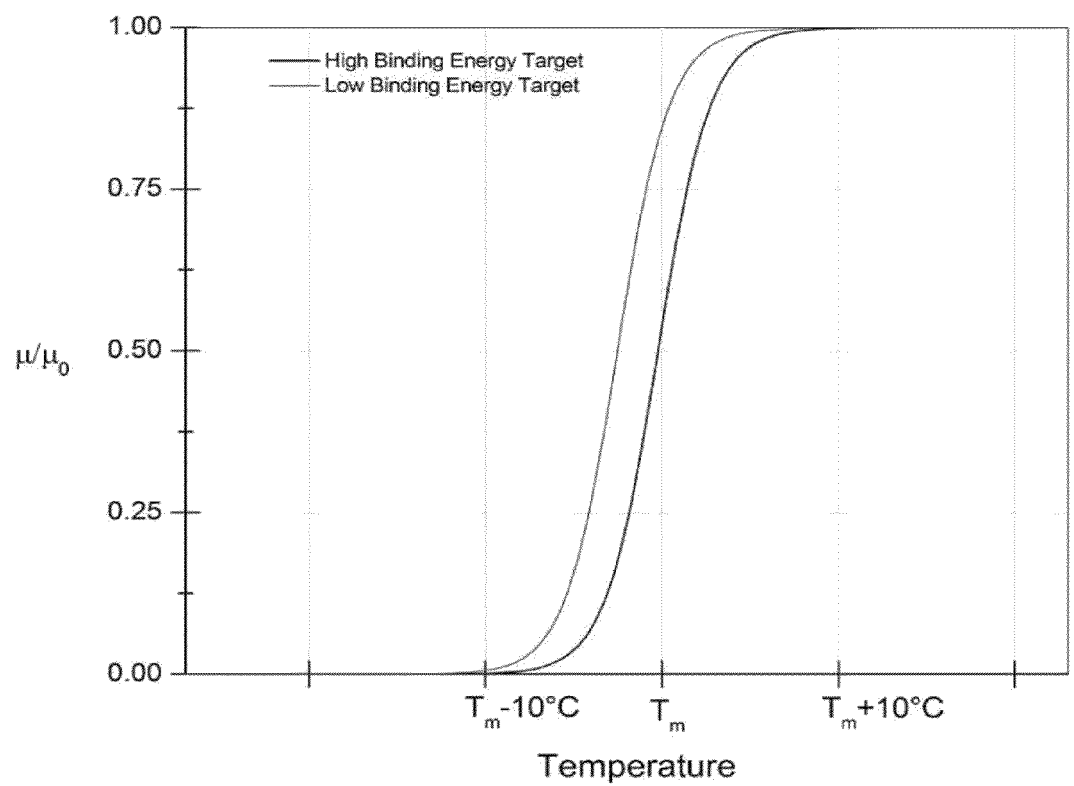
FIG. 8 is a graph illustrating the difference in mobility in an affinity matrix between a target particle with a high binding energy for an immobilized affinity agent (curve on the right) and a target particle with a relatively lower binding energy for the immobilized affinity agent (curve on the left).

The perfect match and the mismatch will have different binding energies to the immobilized probe. Thus, the mobility versus temperature curve will be shifted to a lower temperature for the mismatch sequence as compared with the perfect match sequence, as illustrated in FIG. 8.

Considering the mobility of the particles in this embodiment, the net velocity of the target molecule can be described by the following equation:

$$V_T = \frac{E_L * t_L}{t}(\mu_{H,T} - \mu_{L,T}) \quad [9]$$

where $E_L$ is the magnitude of the low electric field during the cycle, $t_L$ is the time spent in the low electric field during one cycle, t is the period of the entire cycle, $\mu_{H,T}$ is the perfect match (target) mobility at the high field temperature, and $\mu_{L,T}$ is the perfect match (target) mobility at the low field temperature. A similar equation applies to the net velocity of the mismatch (background) particle.

In order to maximize the difference between the velocity of the perfect match (target) (½) and the mismatch (background) particles (VB) in this embodiment, the following can be derived:

$$\Delta V = V_T - V_B = \frac{E_L * t_L}{t}(\mu_L - \mu_H) \quad [10]$$

where:

$$\Delta \mu_L = \mu_{L,B} - \mu_{L,T}$$

and:

$$\Delta \mu_H = \mu_{H,B} - \mu_{H,T}$$

Figure 9:
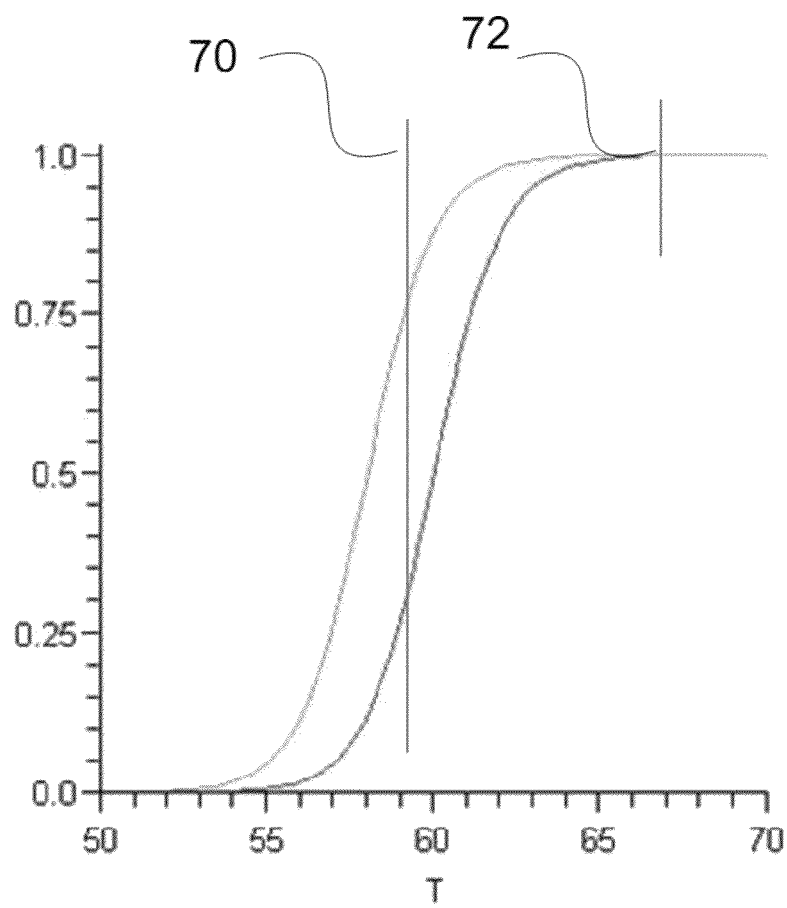
FIG. 9 is a graph illustrating the difference in mobility in an affinity matrix between a target particle with a high binding energy for an immobilized affinity agent and a target particle with a relatively lower binding energy for the immobilized affinity agent, wherein the temperature where the difference in mobility between the two particles is greatest and the temperature where both particles move at approximately their unbound mobility are identified.

Thus, to maximize the difference in net velocity through the separation medium in this embodiment, the difference in mobility between the perfect match and mismatch sequences at the low temperature should be maximized, and/or the difference in mobility between the perfect match and mismatch sequences at the high temperature should be minimized. In some embodiments, the difference in mobility between the perfect match and mismatch sequences at the low temperature is maximized, e.g. as shown at 70 in FIG. 9, and the difference in mobility between the perfect match and mismatch sequences at the high temperature is minimized, e.g. as shown at 72 in FIG. 9.

In some embodiments, separation of two particles is enhanced by superimposing a washing field over the electric fields used to collect particles. Considering that the mobility of a particle within an affinity matrix can be written as the product of the free mobility of the particle (i.e. with no affinity agents present in the separation medium) and the probability that the particle will be unbound from the immobilized affinity agents (and therefore mobile), i.e.

$$\mu_{H,T} = \mu_{f,T} * p_{H,T} \quad [11]$$

the net velocity of particles having the target sequence can be rewritten as:

$$V_T = \frac{\mu_{f,T} * E_L}{t}(t_L * p_{H,T} - p_{L,T}(t_L + t_w)) \quad [12]$$

where $\mu_{f,T}$ is the free target molecule mobility (i.e. with no affinity agents immobilized in the separation medium), $E_L$ is the magnitude of the low electric field in the cycle, t is the period (including the time during which a washing field is applied, $t_w$), $P_{H,T}$ is the probability of the target molecule being unbound at the high electric field temperature, $P_{L,T}$ is the probability of the target molecule being unbound at the low electric field temperature, and $t_L$, is the time during which the low electric field is applied. A similar equation holds true for the net velocity of particles having the background sequence. This equation assumes that the unbound mobility of the target and background sequences is the same (e.g. the target and background sequences are the same length) and that the mobility under the high electric field strength is the unbound mobility, i.e. that $P_{H,T}$ is 1.

The probability that a particle will be bound to the immobilized affinity agent depends on the temperature of the separation medium and the binding affinity of the particle for the affinity agent. At the melting temperature, the probability that a particle will be bound to the immobilized affinity agent is 0.50. As the temperature increases, the probability that the particle will be bound decreases (i.e. the probability that the particle will be unbound increases). As the temperature decreases, the probability that the particle will be bound increases (i.e. the probability that the particle will be unbound decreases).

In some embodiments, the separation of one particle from other similar particles is enhanced by applying a wash field superimposed over the electric fields used to separate particles. In some embodiments, the wash field is an electric field. In some embodiments, the wash field is provided by applying the electric field in one configuration of the cycle for a longer period of time (a washing time) than the electric field is applied in the other n−1 configurations of the cycle. The temperature and duration for which the wash field is applied can be adjusted to effect separation of particles based on the differences in affinity of the particles for an immobilized affinity agent. The washing field essentially causes a departure from the condition that the net motion for particles whose mobilities do not vary under the influence of the mobility altering field is zero.

Using an exemplary embodiment having three separation arms, Table 3 summarizes an exemplary voltage pattern that could be used to separate particles with a washing field using the exemplary embodiment illustrated in FIG. 1. In the exemplary embodiment described below, the mobility altering field is provided by Joule heating caused by the electric field that provides the driving field. In this embodiment, the temperature of the separation medium is maintained at a desired base temperature, e.g. in the range of 40° C. to 60° C., for example using a Peltier element as described above, and the heat produced by the electric field is sufficient to produce the desired increase in temperature. Because of Joule heating due to the passage of current through the separation medium, the temperature within the separation medium will generally be higher than the base temperature set by a temperature controller (e.g. the temperature in the separation medium will generally be higher than the temperature of the Peltier element).

TABLE 3

Exemplary voltage pattern for embodiment with three separation arms providing a washing field.

| Step | Electrode 42A | Electrode 42B | Electrode 42C | Duration |
|------|---------------|---------------|---------------|----------|
| 1 | H | L | H | 1 second |
| 2 | L | H | H | 1 second |
| 3 | H | H | L | 1 second |
| 4 | H | H | L | 0.5 second |

In the exemplary embodiment summarized in Table 3, step 4 provides the washing electric field to the separation arms.

Figure 10:
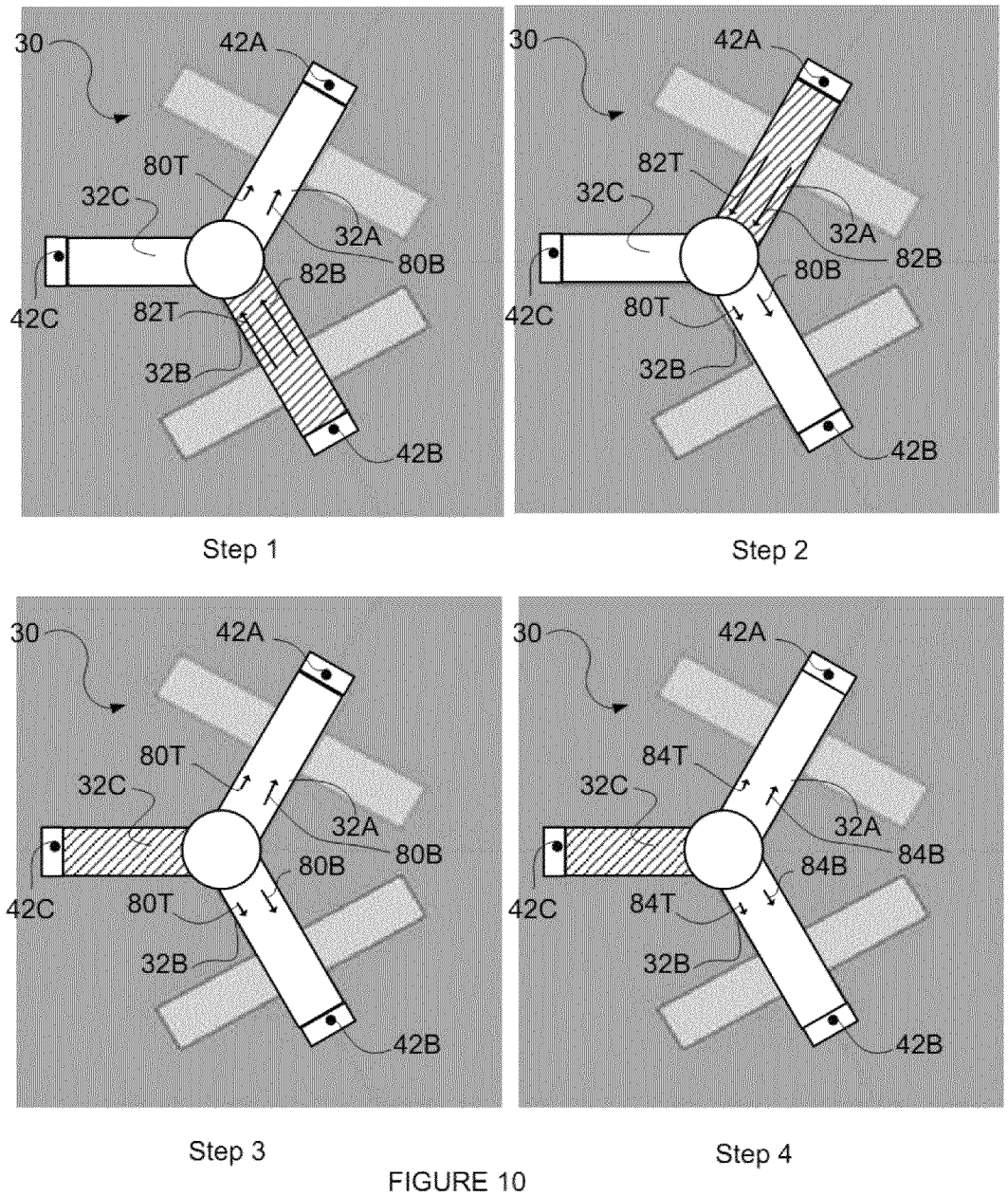
FIG. 10 shows the movement of a hypothetical particle under applied electric fields in an exemplary embodiment using a wash field.

With reference to FIG. 10, the movement of an exemplary pair of oligonucleotide molecules, a target molecule having a perfect sequence match to an oligonucleotide probe immobilized within the separation medium, and a background molecule having a single base mismatch to an oligonucleotide probe immobilized within the separation medium, under the applied electric fields is described. For purposes of the exemplary description below, a mixture of target and background molecules is loaded on each of separation arms 32A and 32B and injected into the separation medium. No sample is loaded on separation arm 32C, which is a washing arm as explained below.

In step 1, separation arms 32A and 32C are regions of low electric field strength (the voltages applied at electrodes 42A and 42C are high). Arm 32B is a region of high electric field strength, as indicated by diagonal shading. Due to conservation of current, the amount of heat being generated by Joule heating in the separation medium in arm 32B will be 4I greater than the amount of heat being generated by Joule heating in separation arms 32A and 32C, where I is the current flowing through each of separation arms 32A and 32C. Thus, arm 32B will also be at a higher temperature than arms 32A and 32C. Both the target and background molecules in separation arm 32A will move in a direction away from central well 34. Because the probability that the background molecules will be bound to the immobilized affinity agent is less than the probability that the target molecules will be bound to the immobilized affinity agent, on average the background molecules in separation arm 32A will move farther during this step than the target molecules in separation arm 32A. The magnitude and direction of this movement are indicated schematically by arrows 80T and 80B in FIG. 10.

In arm 32B, the temperature is higher than in arm 32A. Both the target molecule and the background molecule have a mobility within the medium that approaches the unbound mobility, i.e. the probability that either the target molecule or the background molecule will bind to the immobilized affinity agent is low. Both the target molecule and the background molecule will move approximately the same distance toward central reservoir 34, as indicated schematically by arrows 82T, 82B. Because arm 32B is a region of high electric field strength, the distance travelled by both the target molecule and the background molecule will be greater than it would be at low field strength.

In step 2, separation arms 32B and 32C are regions of low field strength, while separation arm 32A is a region of high field strength, as indicated by diagonal shading. Due to conservation of current, the amount of heat being generated by Joule heating in the separation medium in arm 32A will be 4I greater than the amount of heat being generated by Joule heating in separation arms 32B and 32C, where I is the current flowing through each of separation arms 32A and 32C. Thus, separation arm 32A will also be at a higher temperature than arms 32B and 32C. Both the target and background molecules in separation arm 32B will move in a direction away from central well 34. Because the probability that the background molecules will be bound to the immobilized affinity agent is less than the probability that the target molecules will be bound to the immobilized affinity agent, on average the background molecules in separation arm 32B will move farther during this step than the target molecules in separation arm 32B. The magnitude and direction of this movement are indicated schematically by arrows 80T and 80B in FIG. 10.

In arm 32A, the temperature is higher than in arm 32B. Both the target molecule and the background molecule have a mobility within the medium that approaches the unbound mobility, i.e. the probability that either the target molecule or the background molecule will bind to the immobilized affinity agent is low. Both the target molecule and the background molecule will move approximately the same distance toward central reservoir 34, as indicated by arrows 82T, 82B. Because arm 32A is a region of high electric field strength, the distance travelled by both the target molecule and the background molecule will be greater than it would be at low field strength.

In step 3, separation arms 32A and 32B are regions of low field strength, while separation arm 32C is a region of high field strength, as indicated by diagonal shading. Due to conservation of current, the amount of heat being generated by Joule heating in the separation medium in arm 32C will be 4I greater than the amount of heat being generated by Joule heating in separation arms 32A and 32B, where I is the current flowing through each of separation arms 32A and 32B. Thus, arm 32C will be at a higher temperature than arms 32A and 32B. Both the target and background molecules in separation arms 32A and 32B will move in a direction away from central well 34. Because the probability that the background molecules will be bound to the immobilized affinity agent is less than the probability that the target molecules will be bound to the immobilized affinity agent, on average the background molecules in separation arms 32A and 32B will move farther during this step than the target molecules in separation arms 32A and 32B. The magnitude and direction of this movement are indicated schematically by arrows 80T and 80B in FIG. 10.

In step 4, conditions remain the same as in step 3 for a further period of time (a washing time). Typically, the washing field applied at step 4 will be applied for a shorter period of time than the other configurations of the cycle. In this example, the electric field configuration of step 4 is applied for 0.5 seconds, whereas the electric fields of steps 1, 2 and 3 are applied for 1 second. Both the target and background molecules in separation arms 32A, 32B take a further step away from central reservoir 34, as illustrated by arrows 84T, 84B in FIG. 10. Because the time for which the washing field is applied is only ½ as long as the time for which the low electric field is applied in step 3, the distance traveled by both the target and background molecules in step 4 is on average only ½ as far as the distance traveled in step 3.

In some embodiments in which a wash field is to be applied, sample is loaded on only n−1 of the n separation arms. That is, no sample is loaded on one of the separation arms. For example, in an embodiment having three separation arms, sample is loaded on only two of the separation arms. The arm in which no sample is loaded can be referred to as a "washing arm". In the exemplary embodiment described above, application of the wash field moves negatively charged particles in two (i.e. n−1 where n is 3) of the separation arms away from the central reservoir (as described with reference to separation arms 32A and 32B above). Any negatively charged particles present in separation arm 32C will move towards the central reservoir under the influence of the wash field. Thus, negatively charged particles, including the background molecules, could experience net motion towards central reservoir 34 under the application of a wash field. Loading sample on separation arm 32C could lead to contamination of the target molecules recovered in central reservoir 34 with background molecules. In the illustrated embodiment, separation arm 32C is a wash arm. No sample is loaded on arm 32C. This avoids a risk that the washing field will cause negatively charged particles to move from arm 32C to central reservoir 34.

Figure 11A:
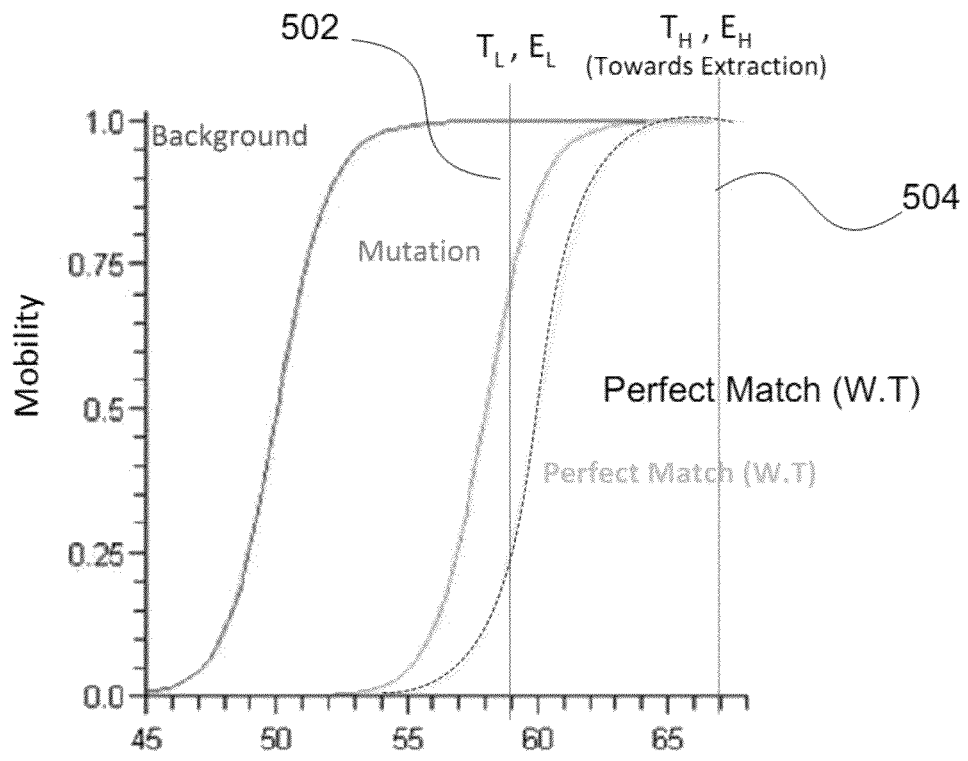
FIG. 11A shows the selected temperatures for separating a perfect match oligonucleotide sequence from a single base mismatch and background sequence to concentrate the perfect match sequence in one exemplary embodiment.
Figure 11B:
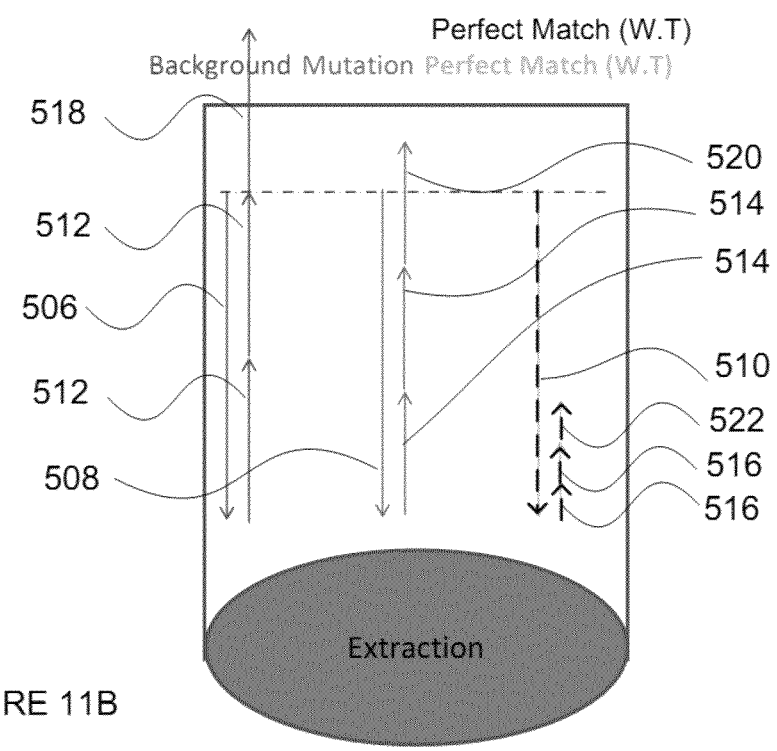
FIG. 11B illustrates schematically the movement of the perfect match, mismatch and background sequences under applied electric fields in one arm of an exemplary apparatus.

With reference to FIGS. 11A and 11B, movement of three exemplary particles in an embodiment having three separation arms under the application of electric fields with a washing field is shown. In this exemplary embodiment, the washing field is applied at the same temperature as the low electric field strength condition. The particles are single stranded DNA. The affinity agent is an immobilized oligonucleotide probe. One of the particles has a sequence that is complementary to (i.e. a perfect match for) the immobilized oligonucleotide probe (identified as W.T or "wild type"). One of the particles, identified as "mutation" has a sequence that is complementary to the immobilized oligonucleotide probe except for a one-base mismatch. Other single stranded DNA particles have sequences that are dissimilar to the complement of the immobilized oligonucleotide probe, and are identified as "background".

FIG. 11A shows the relative mobility of the background, mutation and perfect match DNA particles in an affinity matrix having the oligonucleotide probe immobilized therein. The mobility curve for the background and mutation DNA particles is shifted to cooler temperatures as compared with the perfect match DNA particles. Voltages are applied, for example as summarized in Table 3. The temperature of the separation medium is maintained at a temperature such that the temperature at the low electric field strength ($E_L$) is maintained at a level, $T_L$, at which the difference in mobility between the perfect match and mutation DNA particles is relatively high, as indicated by line 502 in FIG. 11A. At $T_L$, the mobility of the background DNA particles is higher than either the mutation or perfect match DNA particles. The base temperature of the apparatus may be maintained in any suitable manner, for example by using a Peltier element as described above.

The temperatures are selected so that the temperature of the separation medium at the high electric field strength ($E_H$) is maintained at a level, $T_H$, at which the perfect match and mutation DNA particles move with approximately the same mobility through the affinity matrix, indicated by line 504 in FIG. 11A. In some embodiments, the mobility of both the mutation and perfect match DNA particles at $T_H$ approximates the free mobility of both particles (i.e. the mobility of the particles through a medium that does not contain any immobilized affinity agents). At $T_H$, the background DNA particles also move with a mobility similar to the mutation and perfect match DNA particles. One way to produce the required temperatures is through Joule heating. In some embodiments, the applied voltages are selected to produce a level of Joule heating sufficient to raise the temperature of the separation medium to $T_L$ or $T_H$ while the base temperature of the apparatus is maintained at a constant level. For example, a Peltier element may be set to a specific temperature to maintain the base temperature of the apparatus.

FIG. 11B shows schematically the movement of the background, mutation and perfect match sequences under the conditions illustrated in FIG. 11A in one separation arm. The wash field is applied at $T_L$. in the illustrated embodiment. Under the high electric field strength condition (here, step 1), all of the background, mutation and perfect match DNA particles move toward the central extraction well with approximately the same mobility (illustrated by arrows 506, 508 and 510). Because the electric field strength is high, the distance travelled by each of the background, mutation and perfect match DNA particles is relatively large.

Under the low electric field strength condition (here, steps 2 and 3), the background DNA particle moves away from the central extraction well at a high mobility, indicated by arrows 512. The mutation DNA particle moves away from the central extraction well at a mobility higher than the perfect match DNA particle, indicated by arrows 514. The perfect match DNA particle moves away from the central extraction well at a relatively low mobility, as indicated by arrows 516.

Upon the application of a wash field at low electric field strength (here, step 4), the background DNA particle moves away from the central extraction well at a high mobility, indicated by arrow 518. The mutation DNA particle moves away from the central reservoir (extraction well) at a mobility higher than the perfect match DNA particle, indicated by arrow 520. The perfect match DNA particle moves away from the central extraction well at a relatively low mobility, as indicated by arrow 522.

After the application of one complete cycle plus the wash field, the background and mutation DNA particles experience, on average, net motion away from the central extraction well. The perfect match DNA particle experiences, on average, net motion towards the central extraction well. In this embodiment, the average distance traveled by the perfect match DNA particle during times of low electric field strength is less than the average distance traveled by the perfect match DNA particle during times of high electric field strength. The average distance traveled by the background and mutation DNA particles during times of low electric field strength is greater than the average distance traveled by the background and mutation DNA particles during times of high electric field strength.

Figure 12A:
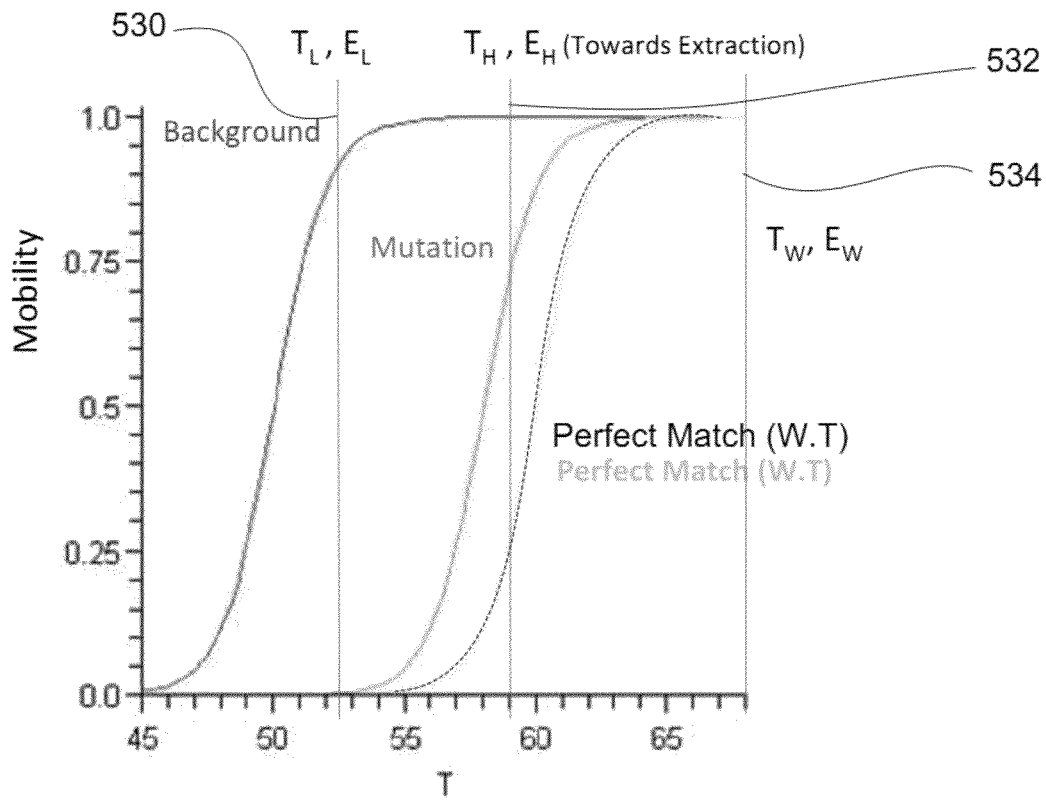
FIG. 12A shows the selected temperatures for separating a perfect match oligonucleotide sequence from a single base mismatch and background sequence to concentrate the single base mismatch sequence in one exemplary embodiment.
Figure 12B:
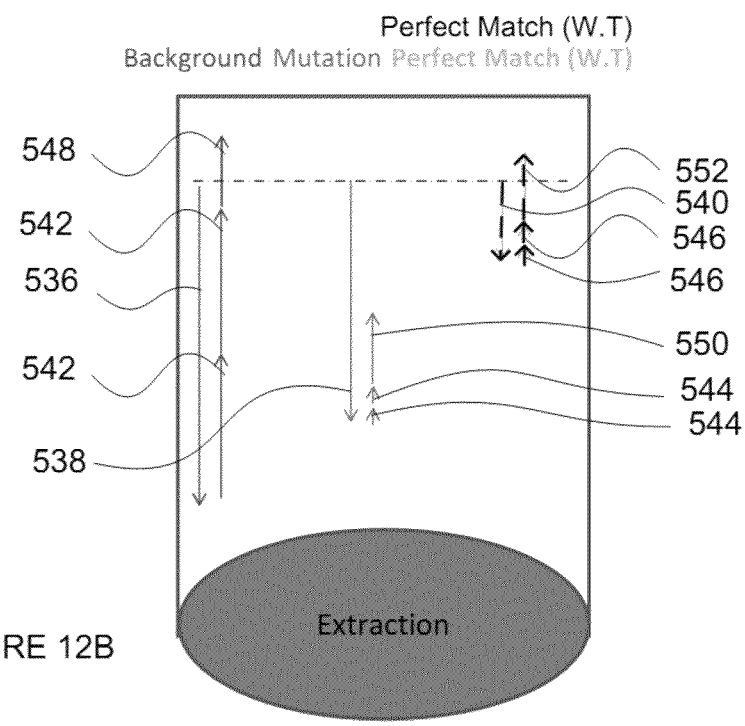
FIG. 12B illustrates schematically the movement of the perfect match, mismatch and background sequences under applied electric fields in one arm of an exemplary apparatus.

With reference to FIGS. 12A and 12B, an exemplary embodiment that can be used to separate and concentrate an oligonucleotide particle containing a point mutation from an oligonucleotide particle having the wild type sequence in the absence of any information as to the specific mutation is described. The exemplary embodiment of FIGS. 12A and 12B utilizes a washing field that is applied at a higher temperature than the electric fields used to concentrate particles, $T_w$. The exemplary DNA particles to be separated in the embodiment of FIGS. 12A and 12B have the same sequence as those in the embodiment of FIGS. 11A and 11B, i.e. background which has a sequence that is not complementary or only partially complementary to the immobilized oligonucleotide probe, mutation which has a sequence that is complementary to the immobilized oligonucleotide probe except for a one base mismatch, and perfect match (W.T), which has a sequence complementary to the immobilized oligonucleotide probe.

The temperature of the separation medium is maintained at a level such that at the low electric field strength condition, $E_L$, the temperature in a given separation arm is at a level, $T_L$, that is sufficiently low that both the mutation and perfect match DNA particles have approximately the same mobility, approximating the fully bound mobility, as indicated at 530 in FIG. 12A. At the high electric field strength condition, $E_H$, the temperature in a given separation arm is raised to $T_H$. $T_H$ is selected so that there is a significant difference in the mobility of the mutation and perfect match DNA particles, as indicated by arrow 532 in FIG. 12A. At $T_H$, the mobility of the background DNA particle is higher than either the mutation or perfect match DNA particles. The temperature of the separation medium during the application of the wash field, $E_W$, is raised to a level at which both the perfect match and mutation have approximately the same mobility through the separation medium, which is a mobility that approximates the free mobility through the separation medium in the illustrated embodiment (i.e. a mobility that approximates the mobility of the DNA particles through the separation medium in the absence of an affinity agent), indicated by arrow 534.

In some embodiments, the three temperatures described above are attained by a combination of heating and/or cooling the medium using an external temperature regulator and by using Joule heating. For example, in the illustrated embodiment, a base temperature of the apparatus may be set by using a temperature regulator, for example a Peltier element. Joule heating due to the flow of current through the medium is used to provide $T_H$. during times of low electric field strength and $T_H$ during times of high electric field strength. The base temperature of the apparatus can then be increased using the temperature regulator, for example by increasing the temperature of the Peltier element, to raise the temperature to $T_W$. Alternatively, the electric field strength could be increased during the washing step and Joule heating used to increase the temperature of the separation medium to $T_W$.

The movement of the DNA particles through the affinity matrix under these conditions in one separation arm is illustrated schematically in FIG. 12B. Under the high electric field strength condition (here, step 1), the background DNA particle moves toward the central extraction well at a relatively high mobility, indicated by arrow 536. The mutation DNA particle moves toward the central extraction well at a moderate mobility, indicated by arrow 538. The perfect match DNA particle moves toward the central extraction well at a mobility less than the mutation DNA particle, indicated by arrow 540.

Under the low electric field strength condition (here, steps 2 and 3), the background DNA particle moves away from the central extraction well with a relatively high mobility, indicated by arrows 542. The mutation and perfect match sequences move away from the central extraction well with a very low mobility, as indicated by arrows 544 and 546.

Under the application of the washing field at Tw (here, step 4), all of the background, mutation and perfect match DNA particles move away from the central extraction well with a relatively high mobility, indicated by arrows 548, 550 and 552, respectively. Thus, the background and perfect match DNA particles experience, on average, net motion away from the central extraction well, while the mutation DNA particles experience, on average, net motion towards the central extraction well. The mutation DNA particles can be separated from both the wild type DNA particles and background DNA particles of similar length and concentrated for further analysis, even in the absence of any information as to the specific point mutation in the mutation DNA particles.

In some embodiments, the mutation DNA particles are collected from the central reservoir (extraction well) and subjected to further analysis, such as sequencing or PCR amplification.

The washing field need not be applied in every electric field cycle, nor at the same time within the electric field cycle. For example, step 4 could be included in every second electric field cycle or in every third electric field cycle or the like, or step 4 could be randomly applied. In embodiments where step 4 does not immediately follow step 3, the time during which the fields of step 4 are applied may need to be adjusted based on the thermal relaxation time of the separation medium. In some embodiments, the electric field cycle is applied for a specific period encompassing several cycles, and then the washing field is applied for a specific period encompassing several wash steps.

The exemplary embodiments described above have been with reference to two oligonucleotides differing in sequence at at least one position. The same principles can be applied to separate any two electrically charged particles having a different binding affinity for an immobilized affinity agent, for example two oligonucleotides that differ in sequence at two or more positions. Oligonucleotides that are methylated can have a different binding affinity for an oligonucleotide probe than the binding affinity of the unmethylated nucleic acid for the same oligonucleotide probe. Oligonucleotides that are differentially modified (i.e. which share the same oligonucleotide sequence but have a methylation pattern that differs from one another) can also have a different binding affinity for an oligonucleotide probe. For example, it has been previously shown that methylation of cytosine residues increases the binding energy of hybridization of a DNA molecule relative to a DNA molecule having an unmethylated sequence. RNA sequences would be expected to display a similar increase in the binding energy of hybridization when methylated as compared with unmethylated sequences. The difference in binding affinity of the methylated versus the unmethylated oligonucleotide sequence will shift the mobility versus temperature curve in the same manner as illustrated in FIGS. 8, 9, 11A, and 12A. Accordingly, the exemplary operating conditions described above can also be used to separate a methylated oligonucleotide molecule from an unmethylated oligonucleotide molecule, or differentially methylated oligonucleotide molecules.

The presence of a chemical modification, such as a methyl group, at a particular point on an oligonucleotide, can be an important biomarker. Hypermethylation or hypomethylation of certain DNA sequences can occur in cancerous or precancerous cells. Bacterial DNA may be differentially methylated as compared to human DNA. Maternal DNA may be differentially methylated as compared with fetal DNA. The methods described above can be used to separate and/or detect the presence of such molecules. Other examples of differentially modified molecules include methylated or acetylated proteins.

Generation of Time Varying Temperature Gradients

Some embodiments that use variations in temperature as the mobility altering field use a periodically varying temperature gradient to produce a convergent velocity field for target particles. A periodically varying temperature gradient may be provided in any suitable manner, for example by the use of heaters or thermoelectric chillers to periodically heat and cool regions of the medium, the use of radiative heating to periodically heat regions of the medium, the application of light or radiation to periodically heat regions of the medium, Joule heating using the application of an electric field to the medium, or the like. In some embodiments, a controller is provided to regulate the operation of heating and/or cooling units.

A time varying temperature gradient can be established so that particles that are spaced a farther distance from a desired focus spot experience greater mobility (e.g. are at a higher temperature and hence travel farther) during times of application of the driving field towards the desired focus spot than during times of application of the driving field away from the desired focus spot. In some embodiments, the temperature gradient is rotated continuously or in steps to produce a convergent velocity field in conjunction with the application of a time-varying driving force. In some embodiments, the temperature gradient may vary in one or two dimensions.

In some embodiments, Joule heating resulting from passage of electric current through the medium is used to provide a temperature gradient. In some embodiments, the electric field used to provide Joule heating to provide a temperature gradient is the same electric field that provides the driving field, that is, the driving field and the mobility altering field are provided by the same field. In some embodiments, the magnitude of the electric field applied is selected or controlled to produce a desired temperature gradient within an affinity matrix. In some embodiments, the spatial distribution and/or non-uniformity of the temperature profile within the affinity matrix is controlled by selecting the electrodes to which the potentials that create the electric field are applied.

Figure 13:
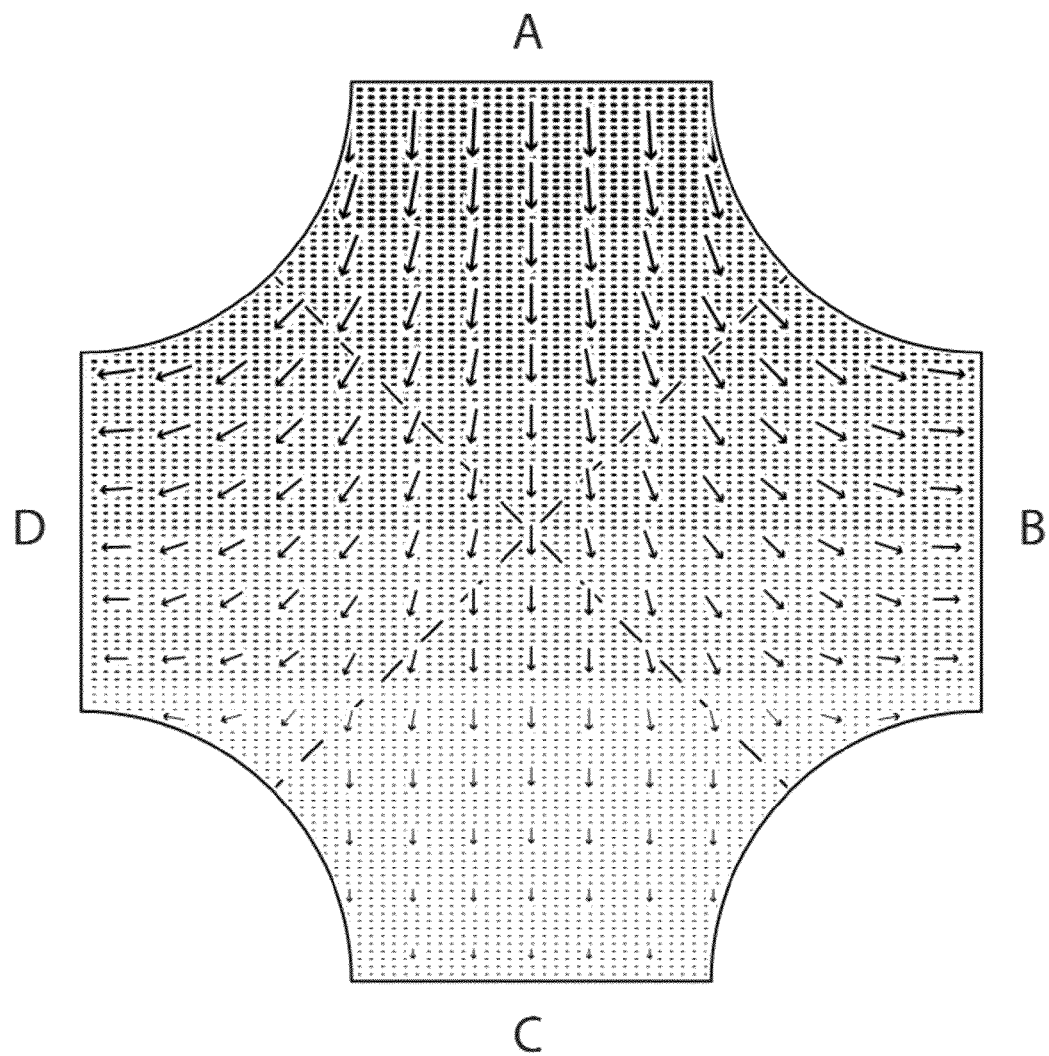
FIG. 13 is a schematic diagram showing an exemplary separation medium and electric field pattern that can be used to concentrate short polynucleotide molecules according to one embodiment. Voltages applied at electrodes A, B, C and D, are −V, 0, 0, and 0 respectively. Arrows represent the velocity of a negatively charged analyte molecule such as DNA. Stippling represents the electric field strength, with denser stippling representing areas of higher electric field strength (top of diagram) and less dense stippling representing areas of lower electric field strength (toward the bottom of the diagram).

In some embodiments, a spatial temperature gradient is generated using an electric field having a quadrupole component to provide Joule heating in a gel medium. The invention is not limited to apparatus having a quadrupole moment or having four electrodes, however. A suitable spatial gradient can be used with any separation arrangement described herein, e.g., having three electrodes, or other arrangements having greater than four electrodes, e.g., five, or six, or seven, or eight electrodes. In some embodiments, a two dimensional gel with four electrodes distributed symmetrically around the gel is provided. This embodiment is exemplified in FIG. 13. As shown in FIG. 13, voltages are applied to the four electrodes such that the electric field in the gel is nonuniform, containing regions of high electric field (and consequently high temperature) and low electric field. The electric field is oriented such that the regions of high electric field tend to push negatively charged molecules towards the center of the gel, while regions of low electric field tend to push such molecules away from the center of the gel. This effect is illustrated in FIG. 13, wherein the voltages applied at electrodes A, B, C and D, are—V, 0, 0, and 0 respectively. Arrows represent the velocity of a negatively charged molecule, for example an oligonucleotide molecule such as DNA. The arrows are longer at the top of the diagram, and become progressively shorter. Density of stippling represents electric field strength, with regions of denser stippling representing regions of higher electric field strength (top of diagram), and regions of less dense stippling representing regions of lower electric field strength (bottom of diagram). The high field regions near electrode A tend to push DNA molecules towards the center of the gel, while the lower field regions near electrodes B, C, and D tend to push DNA molecules away from the center of the gel.

Figure 14:
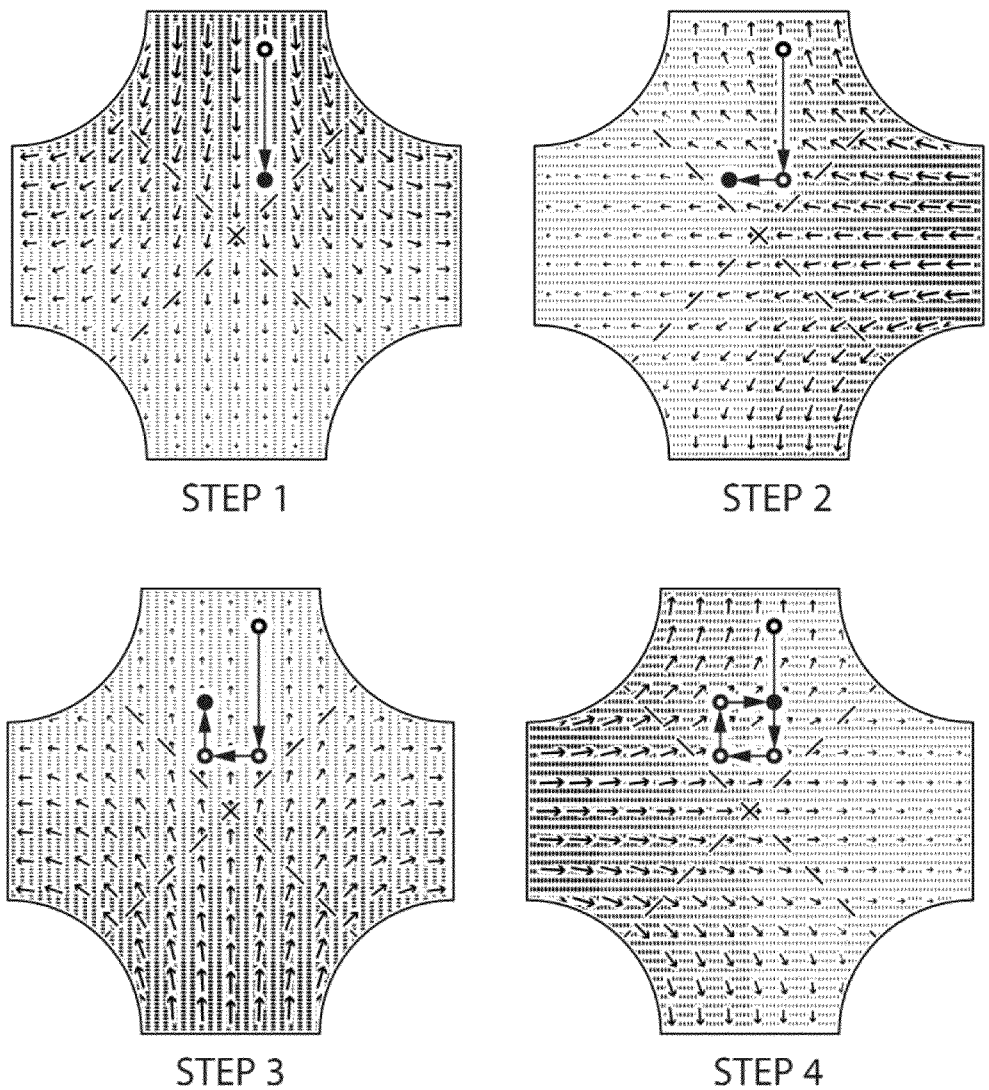
FIG. 14 is a schematic diagram showing the movement of an exemplary particle that has a mobility that varies with temperature in an affinity matrix under the application of rotating superimposed dipole and quadrupole electric fields. Stippling represents the electric field strength, with denser stippling representing areas of higher field strength and less dense stippling representing areas of lower electric field strength. Net movement of the particle after one rotation is towards a focus spot at the center of the separation medium.

In embodiments in which the electric field also provides the temperature gradient, the affinity matrix will become hotter in regions of higher field strength due to Joule heating. Hence, regions of high electric field strength will coincide with regions of higher temperature and thus higher mobility. As illustrated in FIG. 14, particles in the high electric field strength regions will tend to move a greater distance toward a focus spot (which in some embodiments is the center of the affinity matrix), while particles in the lower electric field strength regions have a lower mobility (are at a cooler temperature) and will move only a short distance away from the focus spot. More generally, the driving field and the mobility-altering field are coordinated so that particles experience a higher mobility when the driving field is oriented towards the focus spot than when the driving field is oriented away from the focus spot. Additionally, in the illustrated embodiment, the variation in amplitude of the mobility altering field and the driving field is higher in locations that are relatively farther from the focus spot as compared to locations that are relatively closer to the focus spot, so that particles that are at locations that are relatively farther from the focus spot experience a greater net motion toward the focus spot through the course of one SCODA cycle than particles that are at locations relatively closer to the focus spot.

In some embodiments, the electric field is rotated in a stepwise manner by rotating the voltage pattern around at least three, or preferably four, electrodes spaced symmetrically around the affinity matrix. Each step in the rotation represents one configuration of the SCODA fields. In such embodiments, one SCODA cycle occurs when the voltage pattern has been rotated once around the at least three electrodes. The time averaged electric field may be zero. This rotating field will result in net migration towards the center of the gel for any molecule that is negatively charged and has a mobility within the medium that increases with temperature. In some embodiments, the electric field pattern is varied in a manner other than rotation, e.g. by sequentially shifting the voltage pattern by 180°, 90°, 180°, and 90° (or by 120° in embodiments having only three electrodes), or by randomly switching the direction of the electric field. The mobility of a molecule moving through an affinity matrix depends on temperature, not electric field strength. The applied electric field will tend to increase the temperature of the matrix through Joule heating; the magnitude of the temperature rise at any given point in the matrix will be proportional to the square of the magnitude of the electric field. The application of the electric field is such that when the electric field moves particles at a given location within the matrix in a vector direction towards a focus spot (which is the center of the matrix in some embodiments), the temperature at the given location is increased so that the short polynucleotide molecules at the given location spend less time bound to the immobilized affinity agent than an average amount of time that the short polynucleotide molecules spend bound to the affinity agent during one complete SCODA cycle. When the electric field moves particles at the given location in a vector direction away from the focus spot, the temperature at the given location is decreased so that the relative proportion of time that the short polynucleotide molecules spend bound to the affinity agent is increased relative to the average at the given location. In the exemplary embodiment illustrated in FIG. 14, stepwise rotation of superimposed dipole and quadrupole electric fields produces net movement of a negatively charged particle that has a mobility that varies with temperature in an affinity matrix towards a focus spot.

In the exemplary embodiment of FIG. 14, in step 1, the electric field strength in the region of a particle at a given location within the medium is high and the temperature is relatively high. The particle thus spends a relatively small proportion of time bound to the immobilized affinity agent (i.e. the probability that the particle will bind to the affinity agent is low), and moves a significant distance towards a focus spot (the center of the affinity matrix in this exemplary embodiment) in response to the applied electric field. In step 2, the electric field strength in the region of the particle is moderate and the temperature is moderate. The particle thus spends a moderate proportion of time bound to the immobilized affinity agent (i.e. the probability that the particle will bind to the affinity agent is moderate), and moves a moderate distance in response to the applied electric field. In step 3, the electric field strength in the region of the particle is low and the temperature is low. The particle thus spends a significant proportion of time bound to the immobilized affinity agent (i.e. the probability that the particle will bind to the affinity agent is high), and moves only a short distance away from the focus spot in response to the applied electric field. In step 4, the electric field strength in the region of the particle is moderate and the temperature is moderate. The particle thus spends a moderate proportion of time bound to the immobilized affinity agent (i.e. the probability that the particle will bind to the affinity agent is moderate), and moves a moderate Distance in response to the applied electric field.

In embodiments in which the thermal gradient is provided by Joule heating produced by the electric field that also provides the driving field, the oscillations in the thermal gradient will have the same period as the electric field oscillations. These oscillations can drive SCODA-based concentration (i.e. focusing) in a two dimensional separation medium.

In some embodiments, the electric field and subsequently the Joule heating within a separation medium are controlled by both the voltage applied to the source electrodes, and the shape of the separation medium. Marziali et al. used superimposed rotating dipole and quadrupole fields to drive electrophoretic SCODA concentration. The ratio of the strength of these two fields, the dipole to quadrupole ratio (D/Q), has an impact on the efficiency of SCODA focusing with a maximum at around D/Q=4.5, however the optimum is relatively flat with the SCODA force staying relatively constant for values between 1.75 and 10. One convenient choice of D/Q is 2. With this particular choice, only two distinct potentials need to be applied to the source electrodes. Such fields can be achieved, for example, by connecting one electrode to a common voltage rail, grounding the other three, and rotating this pattern in a stepwise manner through the four possible configurations as shown in Table A. Although analog amplifiers can be used, using a D/Q ratio of 2 allows one to use a constant-voltage power supply and discrete switches to control application of voltages to the electrodes. This simplifies and reduces the required size and complexity of the apparatus.

TABLE A

Voltage pattern for SCODA focusing with D/Q = 2.

| | Electrode A | Electrode B | Electrode C | Electrode D |
|---|---|---|---|---|
| Step 1 | −V | 0 | 0 | 0 |
| Step 2 | 0 | −V | 0 | 0 |
| Step 3 | 0 | 0 | −V | 0 |
| Step 4 | 0 | 0 | 0 | −V |

In some embodiments, a desired operating temperature is maintained by maintaining a base temperature of the separation medium at a given temperature, and allowing Joule heating to produce a time-varying temperature gradient as described above. For example, heating or cooling units can be placed adjacent the separation medium, to maintain a base temperature of the separation medium. In some embodiments, one or more Peltier elements are positioned adjacent to a base plate of a gel cassette containing the separation medium. The Peltier elements are set to maintain a desired base temperature of the separation medium, e.g. 5° C., 10° C., 15° C., 20° C., 25° C., 30° C., 35° C., 40° C., 45° C., 50° C., 55° C., 60° C., 65° C., 70° C., or the like. Heat produced by Joule heating can then be used to produce the desired temperature gradient within the affinity matrix.

In some embodiments, heating and/or cooling units positioned adjacent the separation medium are used to generate the time-varying temperature gradient. In some embodiments, a controller is provided to regulate the temperature of the heating and/or cooling units.

Affinity Matrices

Although the exemplary embodiments have been described above with reference to separation of oligonucleotide molecules, the same principles can be applied to effect separation of other electrically charged particles based on differences in binding affinity for an immobilized affinity agent.

Suitable separation matrices for use in embodiments of the present invention include any matrix suitable for the separation of molecules. In some embodiments, the separation matrix is a gel matrix. In some embodiments, the separation matrix is a polymeric gel, such as agarose, cross-linked polyacrylamide, or linear polyacrylamide. In some embodiments, microfabricated/microfluidic matrices are used.

To produce an affinity matrix, an affinity agent (i.e. an agent which has a binding affinity for one or more short polynucleotide target molecules) is immobilized within the separation matrix. The affinity agent may be any agent that binds to the target molecules. Potentially suitable affinity agents include proteins that bind to nucleic acids (e.g. to double-stranded DNA, single-stranded DNA, or RNA), antibodies, nucleic acids having sequences that are complimentary to the target nucleic acid, DNA or RNA aptamers, or small molecules that can bind to DNA (for example, ethidium bromide or SYBRim green, which can intercalate between stacked base pairs of double-stranded DNA).

In some embodiments, the affinity agent is a protein. Potentially suitable proteins that could be used in embodiments that separate nucleic acids include chromatin binding proteins, histones, zinc finger proteins, helix-turn-helix proteins, leucine zipper proteins, proteins that bind to the minor groove of double stranded DNA, or the like, or the DNA- or RNA-binding domains of such proteins.

In some embodiments used to separate nucleic acids, the affinity agent is a protein that specifically binds to nucleic acids, to a particular nucleic acid molecule, and/or to a nucleic acid molecule having a specific chemical modification. For example, bacterial DNA may have a methylation pattern that is different from human DNA. An affinity agent can be selected to have a different binding affinity for the modified nucleic acid molecule (e.g. methylated DNA) versus the unmodified nucleic acid molecule (e.g. unmethylated DNA or DNA with a different methylation pattern), and the molecule with higher binding affinity for the affinity agent can be preferentially concentrated by the application of electric fields. For example, the chemical modification may result in a difference in binding affinity of the target sequence for its complementary sequence. In some embodiments, a complementary nucleotide sequence can be used to separate a methylated DNA sequence from an unmethylated DNA sequence based on this difference in binding affinity. In other embodiments, antibodies that can specifically bind to bacterial DNA can be used as the affinity agent to preferentially separate, concentrate, purify or detect bacterial DNA in a sample that also includes human DNA (e.g. a sample of bodily fluid). Alternatively, in some embodiments bacterial DNA-binding proteins (such as bacterial chromatin-binding proteins or proteins involved in bacterial DNA or RNA synthesis, or the DNA-binding domains thereof) can be used as the affinity agent to preferentially concentrate bacterial DNA over human DNA.

In other embodiments, antibodies that can specifically bind to bacterial DNA are used as the affinity agent to preferentially separate, concentrate, purify or detect short fragments of bacterial DNA in a sample that also includes human or other (e.g. animal) DNA (e.g. a sample of bodily fluid). Alternatively, in some embodiments bacterial DNA-binding proteins (such as bacterial chromatin-binding proteins or proteins involved in bacterial DNA or RNA synthesis, or the DNA-binding domains thereof) are used as the affinity agent to preferentially concentrate bacterial DNA over human DNA In embodiments in which the affinity agent is a protein, the separation matrix containing the affinity agent should be prepared in such a way that the protein is not denatured. For example, the temperature during preparation, storage and use of the matrix should be kept below a level that would denature the protein (e.g. 100° C.). The concentration of salt and/or the concentration of any denaturing agents in the buffer used to prepare the medium and to conduct separation should be maintained below a level that would denature the affinity agent.

In some embodiments, the separation matrix is a gel and the affinity agent is a protein. The protein is physically contained within the gel matrix. For example, a solution of the protein that is to be used as the affinity agent could be combined with the solution used to make the gel before the gel is cast. The protein becomes bound within the gel matrix when the gel sets, and does not have appreciable mobility under the conditions used to conduct separation. However, the protein is available to interact with the molecules moving through the gel matrix.

In some embodiments, the separation matrix is an agarose gel, the affinity agent is a protein, and the protein is covalently bound to the agarose gel, for example using cyanogen bromide.

In some embodiments, the affinity agent is a protein, and the protein is immobilized within the medium in any suitable manner, for example by being covalently coupled or otherwise strongly bound to a bead or other substrate that is entrained within the medium (for example, a biotinylated protein may bind to a streptavidin-coated bead that is immobilized within the medium).

In some embodiments, the affinity agent is specific for a target polynucleotide sequence. In some embodiments, the affinity agent binds non-specifically to nucleic acids. In some embodiments in which a polynucleotide target molecule to be separated, purified, concentrated and/or detected is double-stranded DNA, the affinity agent is a nonspecific double-stranded DNA binding protein. Exemplary proteins that could be used include chromatin binding proteins, such as histones or modified histones (e.g. acetylated histones), or proteins involved in DNA or RNA synthesis. In some embodiments, the nonspecific DNA binding protein is a histone. In some embodiments, the nonspecific DNA binding protein is histone H2A. In some embodiments, the affinity agent is a molecule other than a protein. For example, small molecule compounds that bind to DNA, e.g. to the major groove or minor groove of double stranded DNA, may be used as the affinity agent.

In some embodiments where the target molecule is single stranded DNA, the affinity agent is a protein that binds specifically to single stranded DNA. In some such embodiments, the affinity agent binds to single stranded DNA in a sequence-independent manner. In some embodiments where the target molecule is RNA, the affinity agent is a protein that binds specifically to RNA. In some such embodiments, the affinity agent binds to RNA in a sequence-independent manner. Examples of proteins which bind to single stranded DNA or RNA in a sequence-independent manner include proteins such as single stranded binding protein (ssBP), or nucleic acid probes having all possible sequence combinations.

In some embodiments, the affinity agent is a nucleic acid. In some embodiments, the affinity agent is a plurality of oligonucleotide probes having random sequences. In some embodiments, the affinity agent is a plurality of short oligonucleotide probes, e.g. 6-mers, 5-mers, or 4-mers, wherein every possible random sequence combination of oligonucleotides is present within the collection of probes. For example, in embodiments in which 5-mer random oligonucleotide probes are used as the affinity agent, there will be 1024 unique oligonucleotide probe sequences immobilized in the matrix. For any given short polynucleotide target molecule, there will be a plurality of sub-sets of oligonucleotide probes that are a perfect complement to the sequence of the target molecule (i.e. one sub-set for each 5 base sequence contained within the target molecule). There will also be a plurality of sub-sets of oligonucleotide probes that have only a one-base mismatch to each 5 base sequence contained within the target molecule, a plurality of sub-sets of oligonucleotide probes that have a two-base mismatch to each 5 base sequence contained within the target molecule, and so on.

In some embodiments, the sequence of the oligonucleotide probes is selected to be complementary to one or more specific sequences of interest. In some embodiments, a plurality of oligonucleotide probes sharing the same sequence complementary to a nucleic acid fragment of interest but having a randomized base at one or more positions known or suspected to be frequently mutated in a particular disorder may be used as affinity agents. Such affinity agents will tend to focus both wild type and mutant target molecules of interest.

In embodiments in which the affinity agent is a nucleic acid, the affinity agent may be immobilized by covalently binding the oligonucleotide probe to the medium, by incorporating acrydite modified oligonucleotide probes directly into a polyacrylamide gel, by covalently binding the oligonucleotide probe to a bead or other construct that is physically entrained within the medium, or the like.

In embodiments where the affinity agent is a small molecule that interacts with DNA, for example an intercalating agent such as ethidium bromide or SYBR green, the small molecule may be bound to the medium via a linker in any suitable manner. In this context, a linker is a moiety that can attach to both the affinity agent and the medium so as to substantially immobilize the affinity agent with respect to the medium. For example, acryloyl chloride may be used to modify ethidium bromide so that it will bind to an acrylamide gel. Avidin/biotin linkers may be used to couple either SYBlem green or ethidium bromide to an acrylamide gel.

In embodiments in which the target molecule is double stranded DNA and in which the affinity agent binds to double stranded DNA, the sample is not denatured prior to being loaded on the affinity matrix or during the application of electric fields. That is, the DNA can be maintained in a double stranded state while the electric fields are applied. In embodiments in which the target polynucleotide fragment is double stranded DNA and in which the affinity agent binds to single stranded DNA, the sample is denatured (for example by boiling) prior to being loaded on the affinity matrix.

If the binding between the affinity agent and the target molecule is too strong, the binding and unbinding interactions required for focusing will not occur (that is, the mobility of the target molecule within the matrix will be reduced to such an extent that net motion will not be practical). Consequently, the affinity agent is selected so that the binding interaction with the target molecule is reversible. In some embodiments, the binding interaction between the target molecule and the affinity agent is primarily through hydrogen-bonding interactions. In some embodiments, the binding interaction between the target molecule and the affinity agent is attenuated through steric effects. In some embodiments, the binding energy between the target molecule and the affinity agent is approximately $k_B T$, where $k_B$ is Boltzmann's constant and T is the absolute temperature.

Suitable temperature ranges for conducting separation of particles according to embodiments of the present invention are typically in the range of about 0° C. to about 100° C. or any value there between, e.g. ranges encompassing 5° C., 10° C., 15° C., 20° C., 25° C., 30° C., 35° C., 40° C., 45° C., 50° C., 55° C., 60° C., 65° C., 70° C., 75° C., 80° C., 85° C., 90° C., or 95° C. The temperature at which separation is conducted should not be so low that the medium or apparatus begin to freeze; thus the minimum temperature at which separation is conducted would typically be higher than about 0° C. The temperature at which separation is conducted should not be so high that the medium or buffer begin to boil; thus the maximum temperature at which separation is conducted would typically be below about 100° C. In some embodiments, separation is conducted at a temperature in the range of about 50° C. to about 60° C.

In addition to the operating temperature, other conditions under which focusing is performed should be selected to ensure that suitable affinity agent target molecule interactions occur. Salt concentration can also affect the binding interaction between the immobilized affinity agent and the target molecule. Salt concentration and operating temperature are maintained in a range chosen to ensure suitable affinity agent-target molecule interactions. The concentration of the immobilized affinity agent may also or alternatively be varied to optimize focusing of molecules that can be achieved by application of electric fields.

Kits for Performing Separation

In some embodiments, a kit is provided. The kit includes a cassette configured to be loaded in an apparatus for applying electric fields to the cassette. The cassette includes a gel containing therein one or more immobilized affinity agents that have a binding affinity for one or more target molecules of interest. The cassette is packaged in a suitable manner to maintain the gel in a condition suitable for use. For example, the cassette may be contained within a sealed water-impermeable package containing a suitable buffer and/or preservation agent to prevent the gel from drying and/or otherwise degrading or becoming contaminated by a microorganism during storage.

In some embodiments, the kit includes suitable buffer(s) that can be used to dilute a sample prior to loading the sample on the gel and/or to conduct separation.

In some embodiments, the kit includes a fluorescently labeled probe that can be used to detect the presence of a particular target molecule in the central reservoir after focusing target particles.

In some embodiments, the kit includes appropriate PCR primers that can be used to subject the target molecule to further analysis, such as PCR detection or sequencing, after the target molecule has been extracted from the gel.

EXAMPLES

Embodiments of the invention are further described with reference to the following examples, which are intended to be illustrative and not restrictive in nature.

Example 1

Sample Loading Using Filter Gel

Figure 15A:
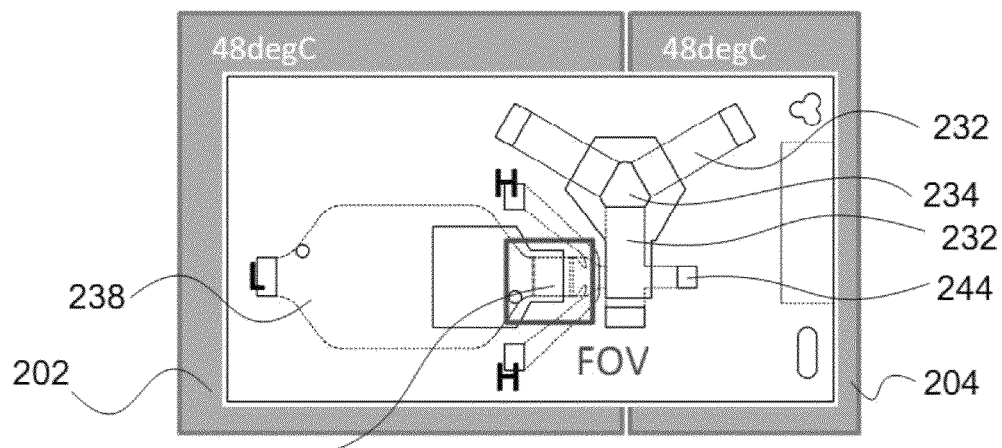
FIG. 15A shows the configuration of an embodiment of an apparatus for separating particles and FIGS. 15B through 15F show images of the injection of a DNA sample into the exemplary apparatus using a filter gel.
Figures 15B, 15C:
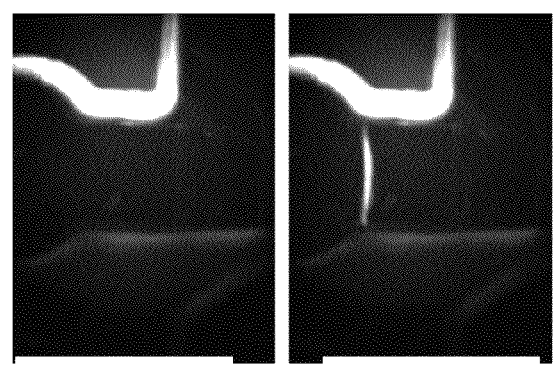

A filter gel having the configuration shown in FIG. 15A was used in this example, in which portions of the apparatus are labeled as described with reference to FIGS. 5A-5D. The filter gel contained an acrydite-modified probe P3 having the sequence 5'-/Acryd/-ACT GA+C TGG TTT TAA TAG+CGA AGG-3' as an immobilized affinity agent, where + precedes a locked nucleic acid base. The melting temperature of probe P3 for the target is 74.5° C., as estimated by commercial software. The apparatus used included two separate Peltier elements. The first Peltier element 204 (temperature indicated as T1 in Table 4) was positioned to allow the temperature of the half of the separation arm farther from the loading reservoir to be separately adjusted. The second Peltier element 202 (temperature indicated as T2 in Table 4) was positioned to keep the loading reservoir and filter gel at a given temperature, and extended approximately half-way into the separation arm used to conduct the separation, abutting the first Peltier element.

The separation medium comprised a 4% polyacrylamide gel made with 1× TB buffer (tris borate buffer) containing 100 mM KCl and a 10 11M *E. coli* acrydite-modified probe P1 having the sequence 5'-/Acryd/-ACT GAC TGG TTT TAA TAG CGA A-3' as an immobilized affinity agent. The melting temperature of probe P1 for the target sequence is 67.4° C. as estimated by commercial software. The running buffer was 1× TB buffer with 100 mM KCl.

The sample was 200 fmol of *E. coli* marker having the sequence 5'-TTT TTT TTT TTT TTT TTT TTT TTT TTT TTT TTT TTT TTT CCT TCG CTA TTA AAA CCA GTC AGT TTT TTT TTT TTT TTT TTT TTT TTT TTT TTT TTT T-3' labeled with either Cy5 (red) or FAM (green) markers, plus approximately 5,000 copies of *E. coli* genomic DNA. The *E. coli* DNA was spiked into whole blood containing approximately 10 g of human genomic DNA, and was processed using a bead beating and magbead protocol. The sample was diluted into approximately 1.2 mL of 0.1× running buffer and loaded into the sample chamber. The voltages set forth in Table 4 were applied as follows:

TABLE 4

Injection, Focus, and Extraction Sequence

| Step | Name | Direction | Duration | T1 | T2 | V | Expected Current |
|---|---|---|---|---|---|---|---|
| 1 | Filter Injection | D to F | 20 C (Coulomb) | 48 | 48 | 100 | 9-13 mA |
| 2 | Swap buffer | — | — | — | — | — | — |
| 3 | Filter Injection | D to F | 20 C | 48 | 48 | 100 | 9-13 mA |
| 4 | Swap buffer | — | — | — | — | — | — |
| 5 | Filter Injection | D to F | 5 C | 48 | 48 | 100 | 9-13 mA |
| 6 | Hot pulse | D to F | 0.2 C | 75 | 75 | 100 | 15-20 mA |
| 7 | Filter Injection | D to F | 15 C | 46 | 46 | 100 | 9-13 mA |
| 8 | Swap buffer | — | — | — | — | — | — |
| 9 | Hot-cold injection | D to E | 5 C | 30 | 70 | 50 V | 1.5 mA |
| 10 | Slide cassette over | — | — | — | — | — | — |
| 11 | Wash/focus | A + B + C | 25 min, 2 + 2.75 + 2.75 s [applied voltages summarized in Table 5] | 51 | 51 | 500 V | 25-28 mA |

TABLE 4-continued

Injection, Focus, and Extraction Sequence

| Step | Name | Direction | Duration | T1 | T2 | V | Expected Current |
|---|---|---|---|---|---|---|---|
| 12 | Focus | A + B + C | 5 min of 2 + 2 + 2 s | 51 | 51 | 500 V | — |
| 13 | Focus | A + B + C | 5 min of 1 + 1 + 1 s | 51 | 51 | 500 V | — |
| 14 | Focus | A + B + C | 30 sec of 0.5 + 0.5 + 0.5 s | 51 | 51 | 500 V | — |
| 15 | Extract from well | — | — | — | — | — | — |

TABLE 5

Voltages applied in wash/focus step (step 11) of Table 4.

| Phase | Time (ms) | A | B | C | Peltier Temp. |
|---|---|---|---|---|---|
| 1 | 2000 | 0 V | 500 V | 500 V | 51° C. |
| 2 | 2750 | 500 V | 0 V | 500 V | 51° C. |
| 3 | 2750 | 500 V | 500 V | 0 V | 51° C. |

The voltage configurations summarized in Table 5 were applied for the equal time periods set forth in Table 4 in focus steps 12, 13 and 14 of Example 1.

Figures 15D, 15E, 15F:
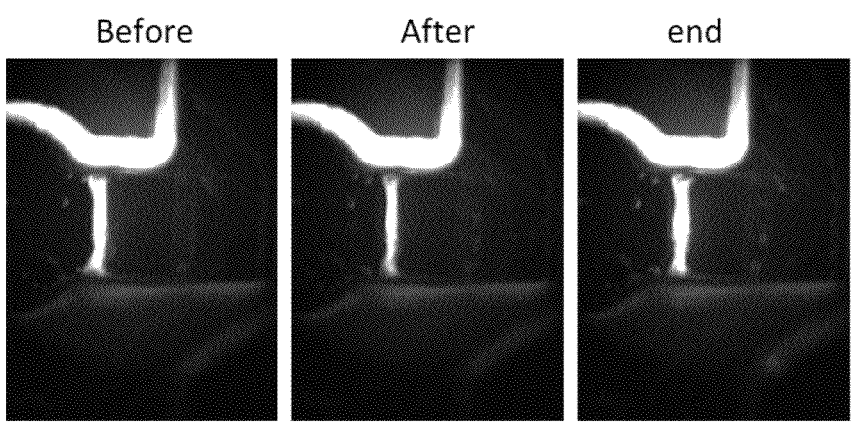
Figure 17A:
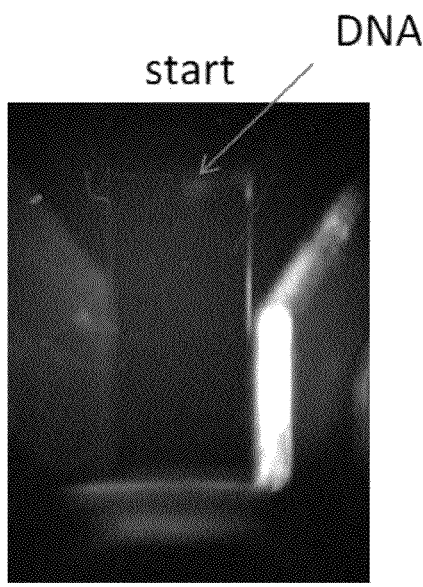
FIGS. 17A, 17B and 17C show the focusing of a DNA sample toward the central reservoir in the embodiment of FIGS. 15A-15F and 16A-16E.
Figure 17B:
Figure 17C:
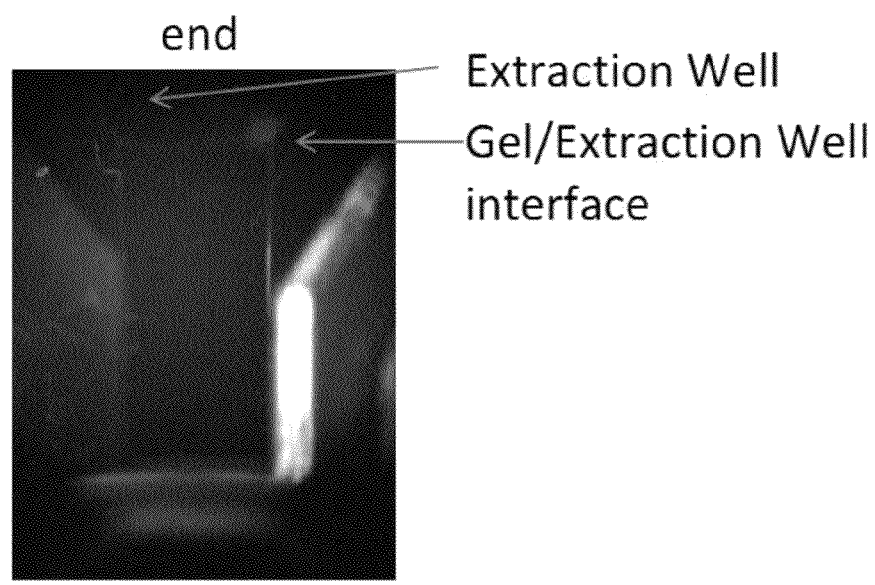

The results of filter injection and applied hot pulse (step 6) are shown in FIGS. 15B-15F. As shown in FIG. 17A and as summarized in Table 4, initially both the first and second Peltier elements 202, 204 are kept at 48° C. The sample is injected into the filter gel, and a voltage is applied from electrode D to electrode F. The *E. coli* marker binds to the *E. coli* probe in the filter gel, while the contaminant human genomic DNA passes through the filter gel and into the exhaust arm. The *E. coli* marker stacks at the leading edge of the filter gel (FIGS. 15B, 15C and 15D) (i.e. the edge of the filter gel adjacent the loading reservoir). At step 6, the temperature of both the first and second Peltier elements is increased to 75° C. This hot pulse is used to free up entangled background DNA and reduce background carry through when injecting into the separation arm (FIGS. 15E and 15F).

Figure 16A:
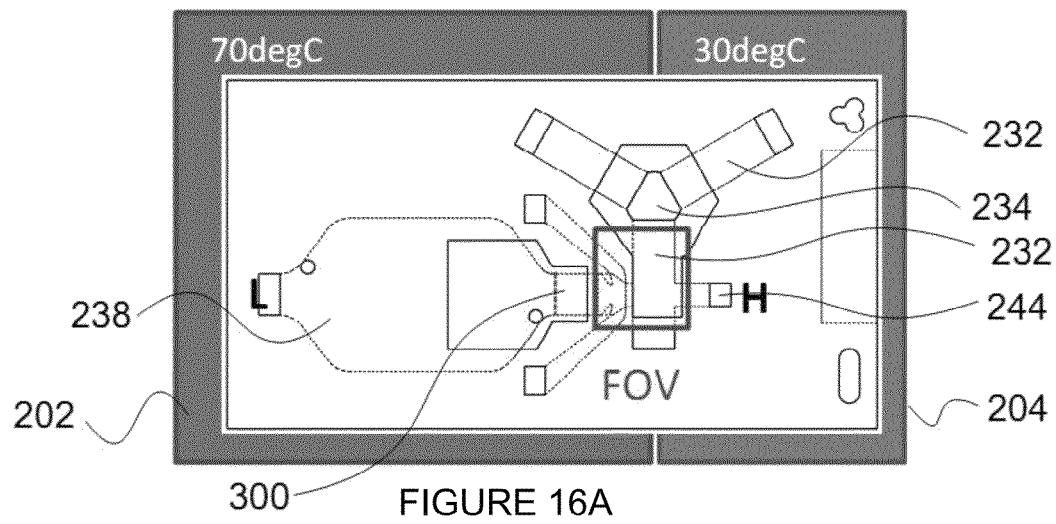
FIG. 16A shows the configuration of the embodiment of FIG. 15A and FIGS. 16B through 16E show the movement of DNA during the injection of a DNA sample from the filter gel into the separation arm in the embodiment of FIGS. 15A-15F.
Figures 16B, 16C:
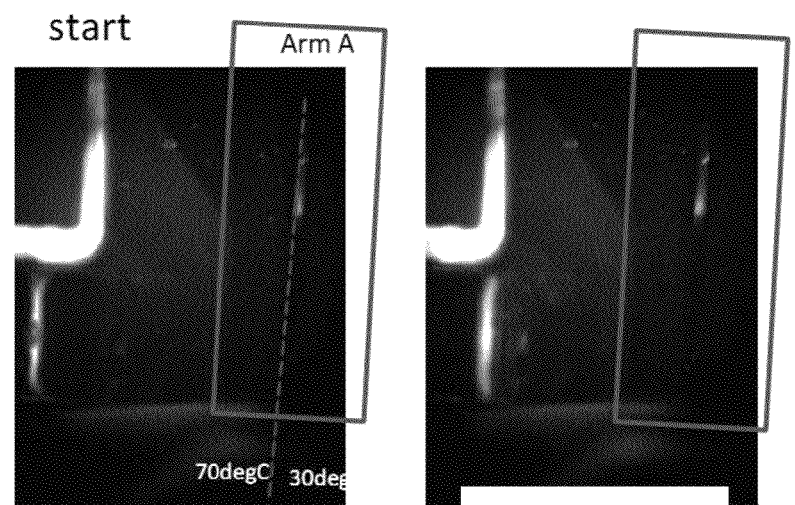
Figures 16D, 16E:
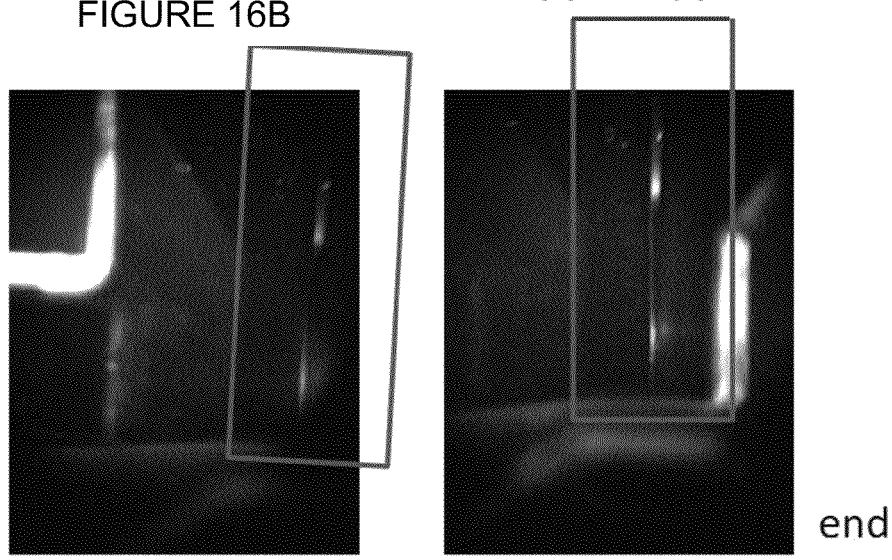

In step 9, hot-cold injection, the temperature of the first Peltier element 204 is decreased to 30° C. and the temperature of the second Peltier element 202 is increased to 70° C. (FIG. 16A). At 70° C., the probability that the *E. coli* marker will bind to the *E. coli* probe present in both the filter gel and the separation arm is low. The marker moves into the separation arm under the applied electric field. When the marker reaches the cold region of the separation arm adjacent the first Peltier element 204, the probability that the marker will bind to the probe present in the separation arm is high. The marker thus stacks in the separation arm (FIGS. 16B, 16C, 16D and 16E). In the illustrated embodiment, the first and second Peltier elements 202, 204 meet in approximately the middle of the width of the separation arm. The marker thus stacks at approximately the middle of the separation arm. Contaminating molecules that do not bind as well to the probe tend to wash through the filter gel and the separation medium.

Figures 19A, 19B, 19C:
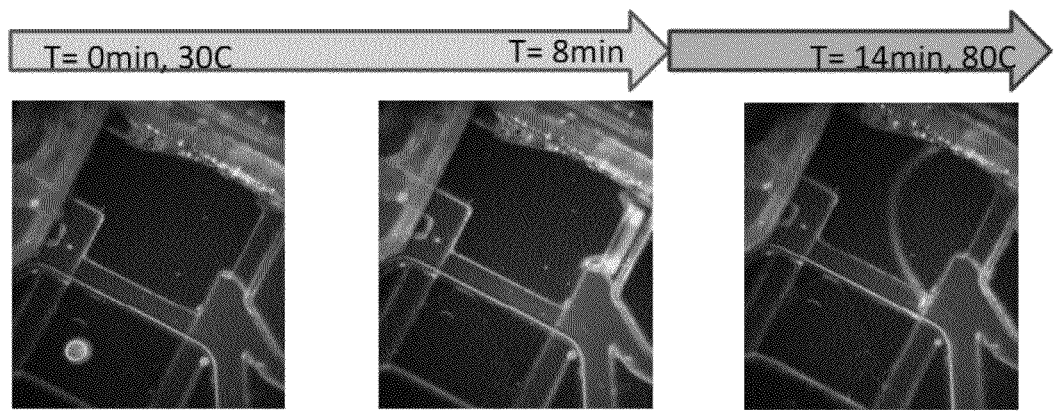
FIGS. 19A through 19F show the rejection of DNA molecules having a perfect match to an immobilized oligonucleotide probe from a sample of DNA molecules having a single base mismatch to the immobilized oligonucleotide probe.

The results of the application of the focusing fields of steps 12, 13 and 14 are shown in FIGS. 19A, 19B and 19C. The DNA is focused and collects at the separation arm-central reservoir interface.

Example 2

Separation of DNA Differing in Sequence at One Base

A KRAS mutant sequence flanked with T's to provide a 100 base oligonucleotide (5'-TTT TTT TTT TTT TTT TTT TTT TTT TTT TTT TTT TTT TTT GTT GGA GCT GTT GGC GTA GGC TTT TTT TTT TTT TTT TTT TTT TTT TTT TTT TTT TTT TTT T-3'), known to be a biomarker for pancreatic cancer, labeled with a green fluorescent marker, was separated from the background wildtype sequence (5'-TTT TTT TTT TTT TTT TTT TTT TTT TTT TTT TTT TTT TTT GTT GGA GCT GGT GGC GTA GGC TTT TTT TTT TTT TTT TTT TTT TTT TTT TTT TTT TTT TTT T-3'), labeled with a red fluorescent marker using a cassette having three separation arms, each with a separate electrode A, B and C. A cassette with three separation arms was used, and a 4% polyacrylamide gel in 1× TB buffer with 100 mM KCl was used as the separation medium. The separation medium contained a 17 nucleotide immobilized probe that was complementary in sequence to the KRAS mutant at a concentration of 100 nM (5'-GCC TAC GCC+A+A+C AGC TC-3', where + precedes locked nucleic acid bases). The running buffer was 1× TB buffer with 100 mM KCl. A single Peltier element was used to set the base temperature of the apparatus.

Figures 18A, 18B, 18C:
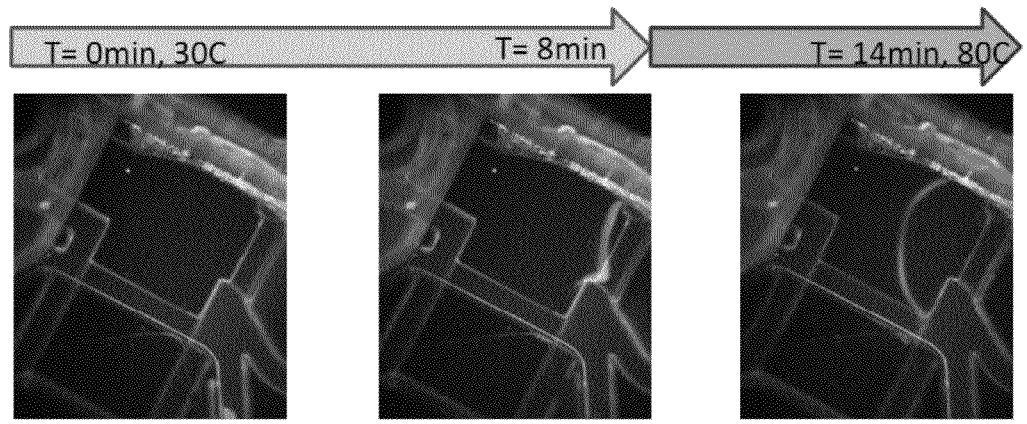
FIGS. 18A through 18F show the separation of DNA molecules having a KRAS mutant sequence from DNA molecules having the KRAS wild type sequence.

The sample was injected into the separation medium directly from buffer. Initially, the Peltier element was maintained at 30° C. during injection to provide a cold injection. The sample is initially visible as a red glow on the right hand side of the image (FIG. 18A). During cold injection, the sample stacks along the gel-buffer interface (red band visible on the right side of FIG. 18B). At 30° C., the probability that both the mutant and wild type target sequences will bind to the immobilized probe is high.

Next, the temperature of the Peltier element was increased to 80° C. (a hot injection step). At this temperature, the probability that both the mutant and wild type target sequences will bind to the immobilized probe is low. The hot injection allowed the stacked band to enter the separation arm of the cassette under the influence of an electric field established by loading electrodes (FIG. 18C).

Next, the temperature of the Peltier element was decreased to 65° C. and the voltages set forth in Table 6 were applied to electrodes at the distal end of each separation arm of the cassette (identified as A, B and C in Table 6) to separate 10 the mutant and wild type KRAS DNA molecules.

TABLE 6

Voltages applied to separate DNA molecules in Example 2.

| Phase | Time (ms) | A | B | C | Peltier Temp. |
|---|---|---|---|---|---|
| 1 | 1000 | 0 V | 475 V | 475 V | 65° C. |
| 2 | 1000 | 475 V | 0 V | 475 V | 65° C. |
| 3 | 1750 | 475 V | 475 V | 0 V | 65° C. |

Figures 18D, 18E, 18F:
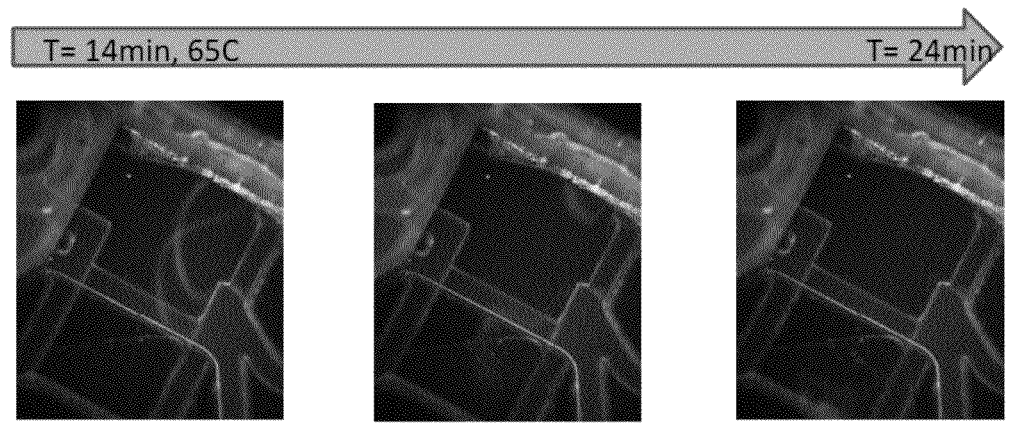

Application of the voltages set forth in Table 6 caused the mutant and wild type DNA molecules to separate. The DNA molecule with the mutant sequence moved toward the central reservoir (green band visible in FIGS. 18D and 18E, and the green band stacked at the separation medium-central reservoir interface in FIG. 18F). The DNA molecule with the wild type sequence was washed out of the separation arm in the opposite direction (red band visible in FIG. 18D and at the top right portion of FIG. 18E).

After the DNA molecule with the wild type sequence had been washed out of the separation medium, the wash field was removed from the electric field cycle—that is, phase 3 was reduced in time to 1000 ms (i.e. the time that each of the phases set forth in Table 6 was applied was adjusted to be 1000 ms). This allowed the DNA molecule with the KRAS mutant sequence to fully enter the central reservoir.

Example 3

Rejection of Perfect Match Sequence

The same DNA molecules and experimental apparatus as in Example 2 were used. However, the operating conditions were modified so that the DNA molecule having the KRAS mutant sequence complementary to the immobilized oligonucleotide probe was washed out of the separation arm, while the DNA molecule having the KRAS wild type sequence (which has a sequence complementary to the immobilized oligonucleotide probe except for one mismatch) was focused in the central reservoir. In this Example, the washing was conducted at a high temperature, where particles with both the mutant and wild type sequences move with approximately the same mobility and approaching the unbound mobility. The low electric field strength and low temperature were selected to be a temperature at which particles with both the mutant and wild type sequences move at a low mobility, which approaches the fully bound mobility. The high electric field strength and high temperature were selected to be a temperature at which there is a significant difference in the mobility of particles with the mutant and wild type sequences.

Again, the sample was initially held in the sample chamber in buffer (FIG. 19A). The Peltier element was maintained at 30° C. A voltage was applied across the loading electrodes, causing the sample to stack along the gel-buffer interface (FIG. 19B). At 30° C., the probability that either the mutant or wild type sequences will bind to the immobilized oligonucleotide probe is high. The temperature of the Peltier element was then increased to 80° C. in a hot injection step, causing both the mutant and wild type sequences to enter the separation medium (FIG. 19C). At 80° C., the probability that either the mutant or wild type sequences will bind to the immobilized oligonucleotide probe is low.

Figures 19D, 19E, 19F:
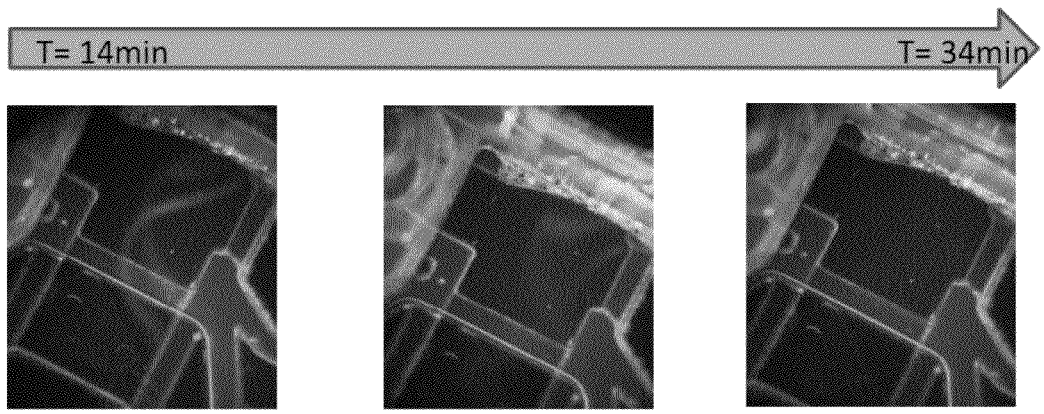

Next, the cassette was subjected to alternating focusing and washing conditions, as summarized in Table 7 and Table 8. The focusing conditions set forth in Table 7 were applied for one minute, and then the washing conditions set forth in Table 8 were applied for 25 seconds. This pattern was repeated. This resulted in the DNA molecules having the wild type KRAS sequence (which has a single base mismatch for the immobilized probe) moving toward the central reservoir (red band visible in FIGS. 19D and 19E), while the DNA molecules having the mutant KRAS sequence (which has a sequence that is the perfect complement of the immobilized probe) move distally out of the separation arm (green band visible in FIGS. 19D and 19E). By the time 34 minutes had elapsed, the red band had entered the extraction well (not visible in FIG. 19F) and the green band had washed off the distal edge of the gel.

TABLE 7

Focus block conditions for Example 3.

| Phase | Time (ms) | A (V) | B (V) | C (V) | Peltier Temp. |
|---|---|---|---|---|---|
| 1 | 1000 | 0 | 400 | 400 | 55° C. |
| 2 | 1000 | 400 | 0 V | 400 | 55° C. |
| 3 | 1000 | 400 | 400 | 0 V | 55° C. |

TABLE 8

Wash block conditions for Example 3.

| Phase | Time (ms) | A (V) | B (V) | C (V) | Peltier Temp. |
|---|---|---|---|---|---|
| 1 | 1000 | 150 | 0 | 0 | 70° C. |
| 2 | 300 | 0 | 0 | 0 | 70° C. |

Example 4

Separation of DNA Molecules by Size

A flared six channel gel boat with four tapered separation arms as illustrated in FIG. 6 was used to separate DNA fragments of different sizes. The separation medium was 1% SeaKem LE agarose in 0.05×TBE buffer, with a thickness of 5 mm. The running buffer was 0.05×TBE buffer. The sample was 200 ng of lambda HindIII ladder labeled with SYBR Green in water. A Peltier element was used to adjust the base temperature of the apparatus to 5° C. Due to Joule heating, the temperature within the separation medium is higher than the base temperature set by the Peltier element. The sample was injected into the separation arms via the central reservoir by applying an electric field of 350 V for 5 minutes and 20 seconds. Defocusing fields (i.e. an electric field configured so that the high electric field strength condition coincides with movement of the DNA in the distal direction, rather than in the direction towards the central reservoir) were applied to electrodes at the distal ends of the four separation arms (labeled as A, B, C and D in Table 10) at 38 V/cm for 202 minutes with a 320 millisecond period. Focusing fields were applied to the four separation arms at 75 V/cm with a 4 second period for 15 minutes plus 40 minutes.

TABLE 10

Defocusing conditions for Example 4.

| Phase | Time (ms) | A (V) | B (V) | C (V) | D (V) | Peltier Temp. (° C.) |
|---|---|---|---|---|---|---|
| 1 | 80 | 147 | 0 | 0 | 0 | 5 |
| 2 | 80 | 0 | 147 | 0 | 0 | 5 |
| 3 | 80 | 0 | 0 | 147 | 0 | 5 |
| 4 | 80 | 0 | 0 | 0 | 147 | 5 |

TABLE 11

Focusing conditions for Example 4.

| Phase | Time (ms) | A (V) | B (V) | C (V) | D (V) | Peltier Temp. (° C.) |
|---|---|---|---|---|---|---|
| 1 | 1000 | 0 | 291 | 291 | 291 | 5 |
| 2 | 1000 | 291 | 0 | 291 | 291 | 5 |

TABLE 11-continued

Focusing conditions for Example 4.

| Phase | Time (ms) | A (V) | B (V) | C (V) | D (V) | Peltier Temp. (° C.) |
|---|---|---|---|---|---|---|
| 3 | 1000 | 291 | 291 | 0 | 291 | 5 |
| 4 | 1000 | 291 | 291 | 291 | 0 | 5 |

Figure 20A:
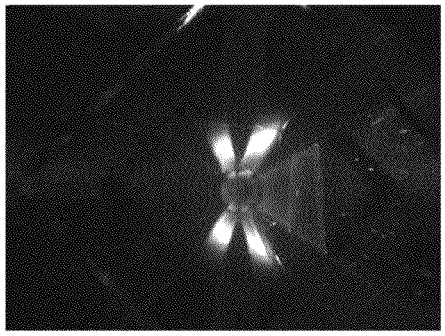
FIGS. 20A-20E show the results of the separation of DNA fragments using an embodiment of a separation apparatus having four tapered arms as illustrated in FIG. 6.
Figure 20B:
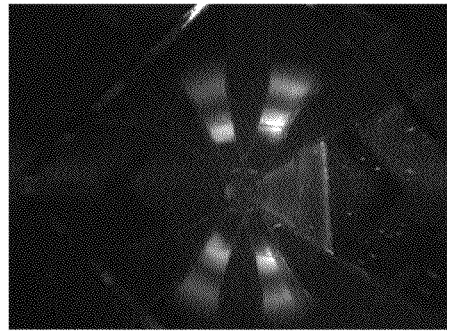
Figure 20C:
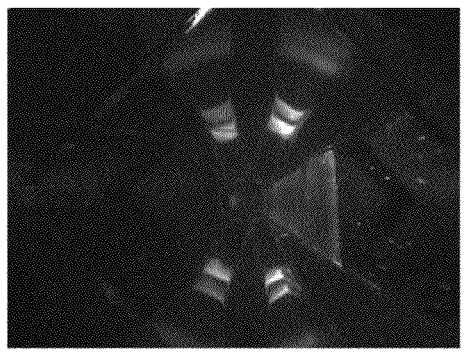
Figure 20D:
Figure 20E:
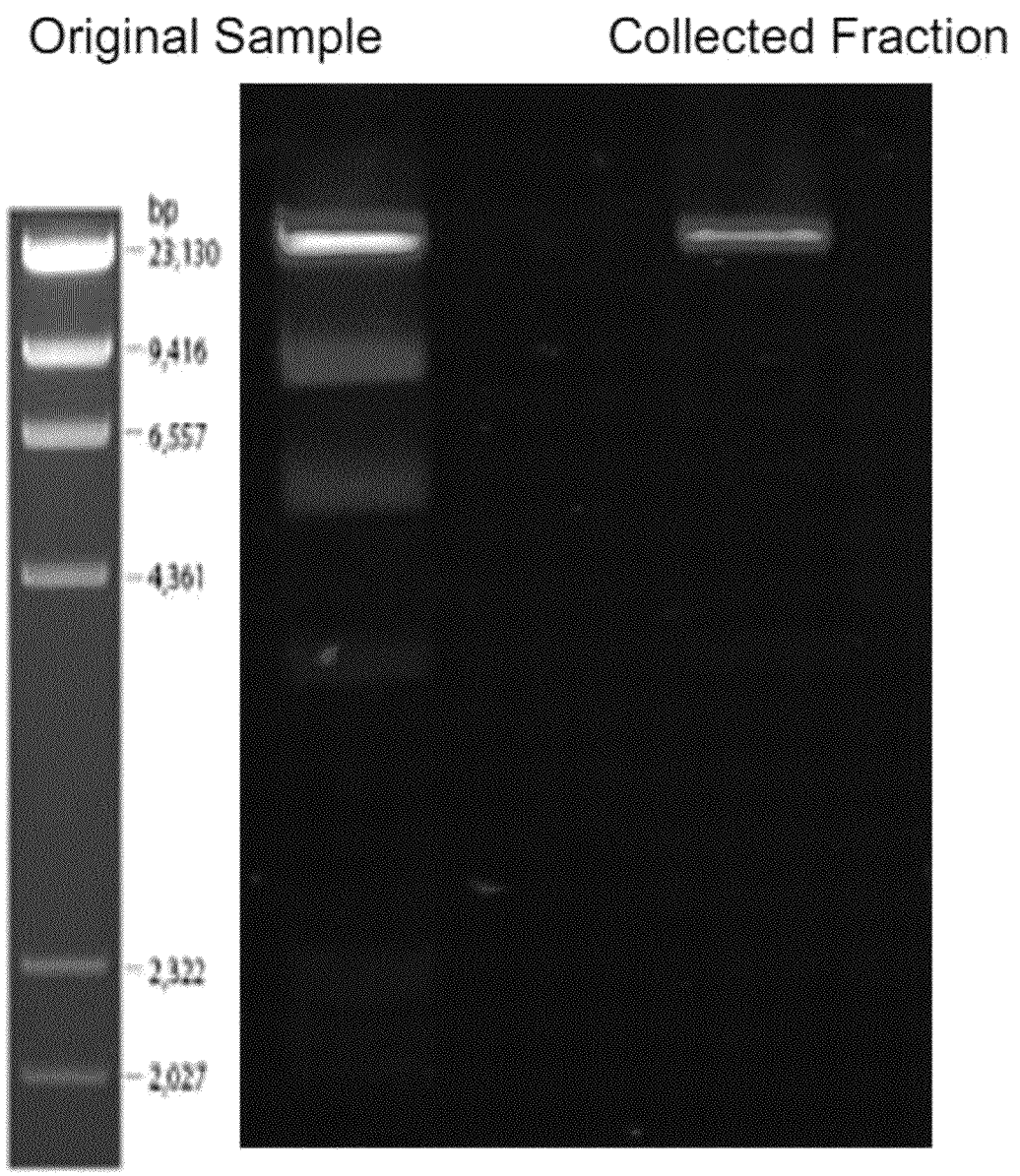

The results are shown in FIGS. 20A-20E. The labeled DNA is visible in each of the four separation arms after 5 minutes of injection (FIG. 20A). FIGS. 20B, 20C and 20D show the bands of DNA formed after 25, 90 and 150 minutes application of the defocusing fields, respectively. Eventually the large DNA reaches an equilibrium point and no longer experiences net motion under the application of the defocusing fields, while shorter DNA fragments migrate out of the distal ends of the separation arms. FIG. 20E shows a gel comparing 40 ng of the original sample (left panel) to the DNA sample collected after application of the focusing fields.

Example 5

Histone H2A as Affinity Agent

Experiments were carried out using the protein histone H2A as an affinity agent to focus 91 base pair (bp) double-stranded target DNA molecules. The DNA molecules used had the sequence 5'-TGT AAC TCG CCT TGA TCG TTG GGA ACC GGA GCT GAA TGA AGC CAT ACC AAA CGA CGA GCG TGA CAC CAC GAT GCC TGT AGC AAT GGC AAC AA-3' (derived from pUC19). Experiments using histone H1 as the affinity agent were also conducted, but were not successful in focussing DNA fragments. Without being bound by any particular theory, it is hypothesized that the binding interaction between the target DNA and histone H1 is too strong to allow focusing to occur under the application of the SCODA fields applied in this example.

Example 5.1

Temperature Studies

Temperature studies were conducted on gels cast in channel geometry SCODA cassettes. The gel thickness was 100 µm. A 5% polyacrylamide gel with a 37.5:1 croslinking ratio was used. A DC-field of 25 V/cm was applied to five separate gels at varying temperatures. The temperatures chosen for this preliminary study included 10° C., 25° C., 40° C., and 50° C. (FIGS. 21A-21D). All gels were run at the same protein and salt concentration of 5 µM and 0.2M NaCl, respectively. 20 ng of 91 bp DNA in 250 µl of 0.01×SFS buffer (1×SFS buffer is 1×TBE buffer (tris/borate/EDTA) with 0.2 M NaCl) was loaded in the sample chamber of the cassettes.

Figure 21A:
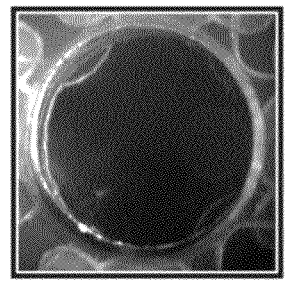
FIGS. 21A-D show injection of 91 base pair double stranded DNA into a gel incorporating histone H2A as an affinity agent at varying temperatures with an applied DC-field of 25 V/cm.
Figure 21A:
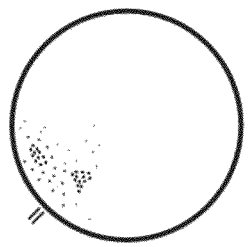
Figure 21B:
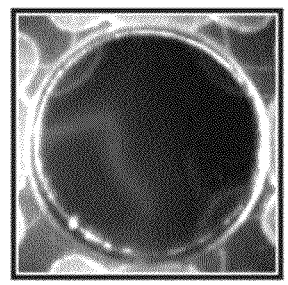
Figure 21B:
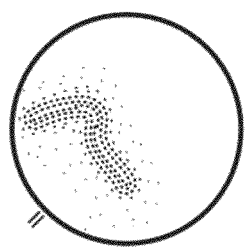
Figure 21C:
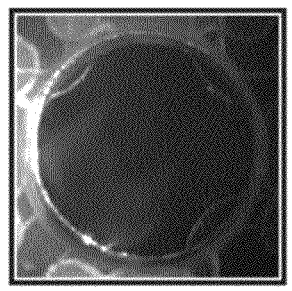
Figure 21C:
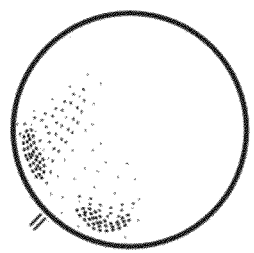

At 10° C., the sample did not stack and was bound to gel in the form of a smear and experienced minimal movement after 40 minutes (FIG. 21A, results shown schematically in FIG. 21Ai). Repeating the experiment at 25° C. resulted in DNA stacking and forming a tight band that moved uniformly through gel (FIG. 21B, results shown schematically in FIG. 21Bi). The DNA injected to a central point on the cassette within 60 minutes. This temperature was chosen as the injection temperature for further experiments.

Higher temperatures were then investigated to determine the conditions under which the protein was completely unbound from the DNA. At 40° C. (FIG. 21C, results shown schematically in FIG. 21Ci), the DNA did not stack and dispersed throughout the gel. The majority of the sample experienced very slow movement, indicating stronger binding than at 25° C. One possibility is that because 40° C. is close to the core human body temperature of 37.5° C., histone H2A may be more effectively binding the DNA at the higher temperature. This would cause less movement over an allotted period of time.

Figure 21D:
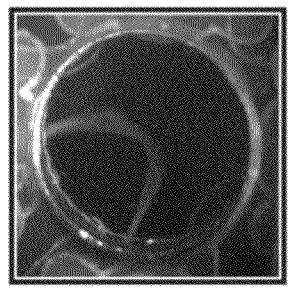
Figure 21D:
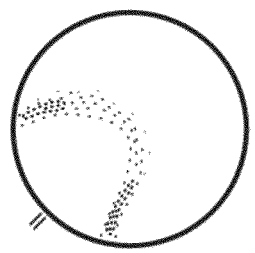

Upon raising the temperature further to 50° C., the DNA moved relatively freely through the gel (FIG. 21D, results shown schematically in FIG. 21Di). This temperature was selected as the focusing temperature for further experiments.

Example 5.2

Figure 22A:
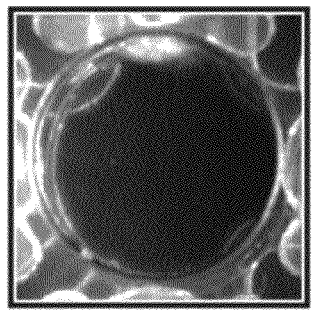
FIGS. 22A-22C show injection of a 91 base pair double stranded DNA into a gel incorporating histone H2A as an affinity agent at varying salt concentrations with an applied DC-field of 25 V/cm.
Figure 22A:
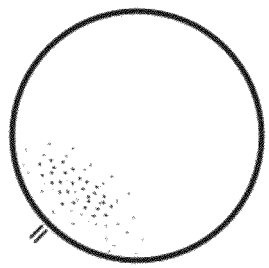
Figure 22B:
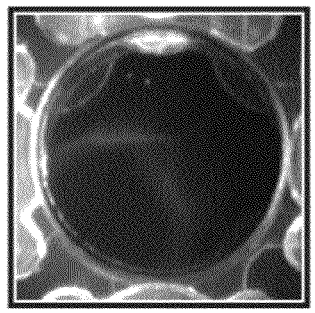
Figure 22B:
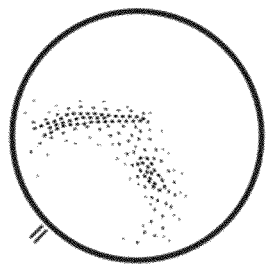
Figure 22C:
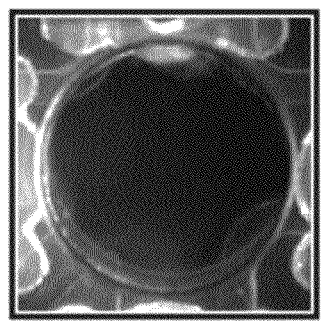
Figure 22C:
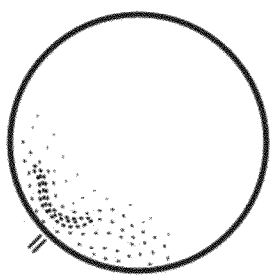

Effect of Sodium Chloride (NaCl) Concentration 0.2M NaCl was selected as the starting salt concentration. The sample proteins were supplied in 0.2M NaCl, so this condition was tested. To ensure the system was operating at the appropriate salt concentration, 0M NaCl and 0.3M NaCl were tested (FIGS. 22A and 22C), as well as 0.2M NaCl (FIG. 22B). All experiments were run at 25° C. with an applied DC field of 25 V/cm. At 0M NaCl, the DNA is completely bound to H2A (FIG. 22A, results shown schematically in FIG. 22Ai). This result was expected since it has previously been shown that increasing NaCl concentration results in a lower binding of H2A to DNA. However, at 0.3M NaCl, there was also less movement of DNA (FIG. 22C, results shown schematically in FIG. 22Ci). This seems contrary to expectation. At higher salt concentrations, there is the possibility of forming depletion regions in the gel. This happens when there is a net flux of positive ions in one direction and a net flux of negative ions in the opposite direction, creating an area with an absence of charged species. This would disrupt the system. 0.2M NaCl was selected for performance of further experiments given that good injection of the DNA was achieved under these conditions (FIG. 22B, results shown schematically in FIG. 22Bi).

Example 5.3

Focusing through Application of SCODA Fields

Figure 23A:
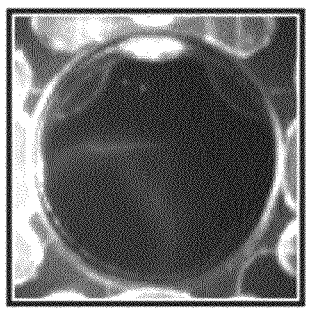
FIGS. 23A to 23D show results from an embodiment using histone H2A as an affinity agent, versus a control sample with no affinity agent.
Figure 23A:
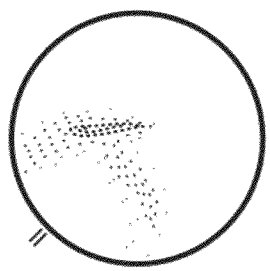
Figure 23B:
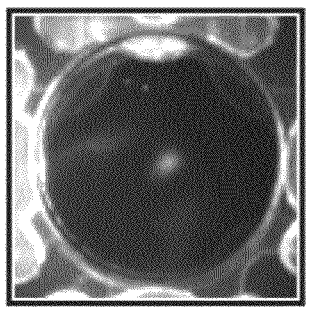
Figure 23B:
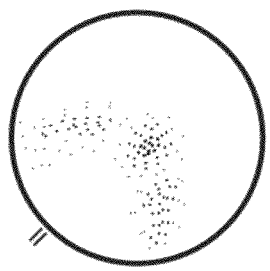

The conditions selected above were used for the performance of SCODA phoresis in the presence of a SCODA field (i.e. a time-varying driving field and a time-varying mobility altering field). The sample was injected at 25° C. for 60 minutes, until the DNA band was near the center of the gel (FIG. 23A, shown schematically in FIG. 23Ai). Alternating electric fields of 40 V/cm at a base temperature of 50° C. were then applied for 200 minutes in a rotating pattern around four electrodes. It is estimated that the maximum temperature of the gel caused by Joule heating under these conditions would be just below boiling temperature, e.g. about 95° C. After 200 minutes, a concentrated focus spot was obtained (FIG. 23B, results shown schematically in FIG. 23Bi), although there was still some DNA present in the gel that did not respond to the focusing fields.

Figure 23C:
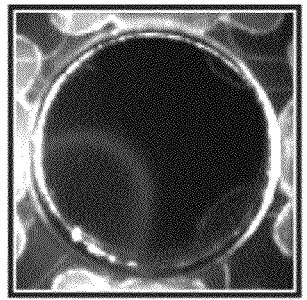
Figure 23C:
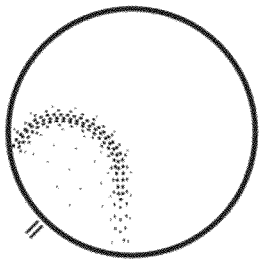
Figure 23D:
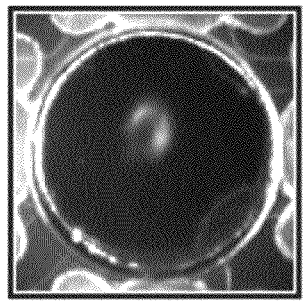
Figure 23D:
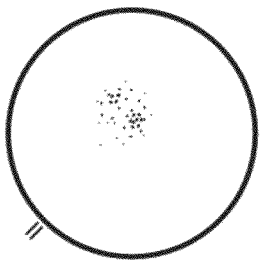

A control was also run under the same conditions without H2A in the gel. The injection occurred within 10 minutes at 25 V/cm (FIG. 23C, results shown schematically in FIG. 23Ci), which is 6 times faster than with the protein in the gel. In addition, the radius of the focus spot was significantly larger (FIG. 23D, results shown schematically in FIG. 23Di).

Example 5.4

Control Studies

Example 5.4.1

Lysozyme

Figure 24A:
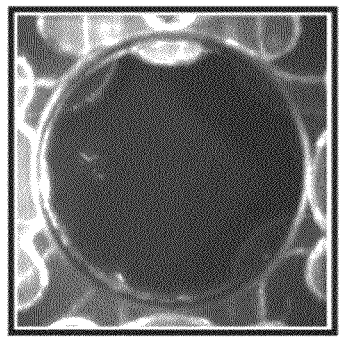
FIGS. 24A and 24B show a control experiment including lysozyme as a control protein that does not interact with 91 base pair double stranded DNA in the gel.
Figure 24A:
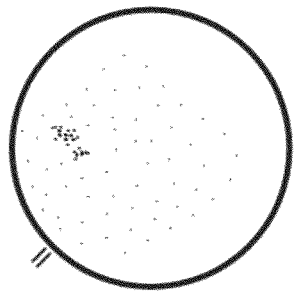
Figure 24B:
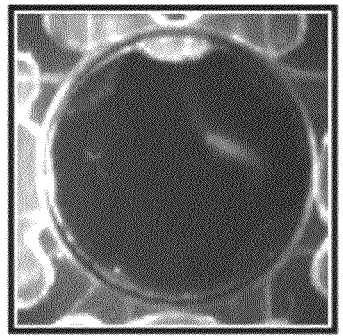
Figure 24B:
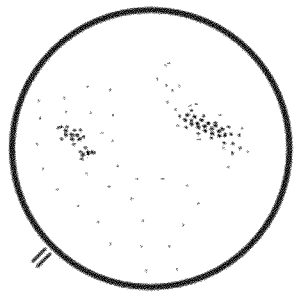

To ensure the histone H2A protein was actually interacting with the DNA and not simply creating a steric barrier for the sample, the inventors incorporated lysozyme into a gel and performed SCODA focusing. Lysozyme has a molecular weight of 14 KDa, similar to that of H2A. The inventors injected and focused the same 91 bp DNA fragment under the same conditions as described above. After injecting for 10 minutes at 25 V/cm, the sample was evenly dispersed throughout the entire gel (FIG. 24A, shown schematically in FIG. 24Ai). This result indicates that the DNA is not blocked by the size of the protein and the slower injection of DNA in the H2A gel is due to a histone-DNA interaction. Furthermore, after focusing, the DNA did not concentrate at the center of the gel which included lysozyme (FIG. 24B, results shown schematically in FIG. 24Bi).

Example 5.4.2

Testing of Contaminants (Humic Acids)

Figure 25A:
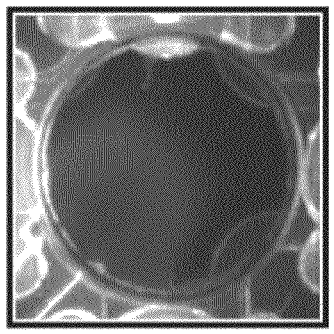
FIGS. 25A and 25B show results of injection of 2 µg of humic acids, an exemplary contaminant, into a gel containing H2A.
Figure 25A:
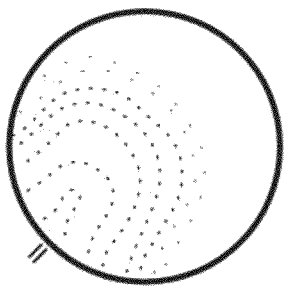
Figure 25B:
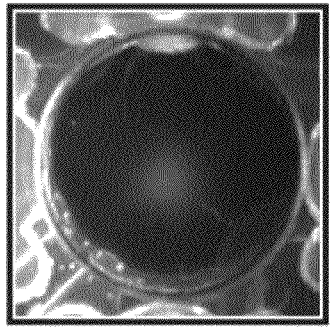
Figure 25B:
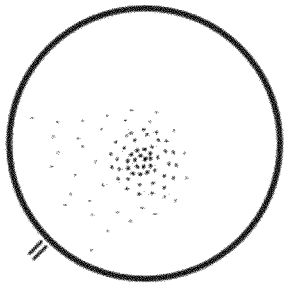

2 g of humic acids (an exemplary contaminant) were injected instead of DNA. After applying a DC-field of 25 V/cm, the humic acid sample injected in only 7 minutes (FIG. 25A, shown schematically in FIG. 25Ai). This was followed by applying 40 V/cm alternating fields for 200 minutes (FIG. 25B, results shown schematically in FIG. 25Bi).

Under the same conditions as the experiment with a sample of 91 bp DNA, the humic acids do not focus to the same extent.

Aspects of the exemplary embodiments and examples described above may be combined in various combinations and subcombinations to yield further embodiments of the invention. To the extent that aspects of the exemplary embodiments and examples described above are not mutually exclusive, it is intended that all such combinations and subcombinations are within the scope of the present invention. Accordingly, one skilled in the art will recognize that embodiments of the present invention have a number of aspects, including:

The invention claimed is:

1. An apparatus for separating particles comprising:
at least three electrodes circumferentially surrounding a central reservoir, with a separation medium between at least one electrode and the central reservoir, wherein the separation medium comprises an affinity agent that has a binding affinity for a target particle.

2. An apparatus for separating particles comprising:
at least three electrodes circumferentially surrounding a central reservoir, with a separation medium between at least one electrode and the central reservoir;
an arm between each of the at least three electrodes and the central reservoir, at least one of the arms comprising the separation medium, wherein the arm comprising the separation medium comprises a loading reservoir adjacent the separation medium, wherein the loading reservoir extends perpendicularly relative to the length of the separation arm; and
a loading buffer chamber adjacent the separation medium and opposite the loading reservoir.

3. The apparatus of claim 2, comprising a first loading electrode in the loading reservoir and a second loading electrode in the loading buffer chamber.

4. A method for separating target and background particles comprising:
providing a central reservoir and n separation arms containing a separation medium extending outwardly from the reservoir;
loading a sample on at least one of the separation arms;
applying an electric field that is low in n−1 of the separation arms and high in one of the separation arms; and
varying the configuration of the applied electric field a plurality of times so that on average the electric field is high in each one of the n separation arms 1/n of the time and low in each one of the n separation arms (n−1)/n of the time, wherein n is at least 3.

5. The method of claim 4, further comprising maintaining a base temperature of the separation medium at a predetermined level.

6. The method of claim 5, wherein the base temperature is maintained in the range of 45.degree. C. to 65.degree. C.

7. The method of claim 4, comprising allowing Joule heating to increase the temperature in one of the separation arms while the electric field strength in that separation arm is high.

8. The method of claim 4, further comprising applying a washing field to the medium.

9. The method of claim 8, wherein applying the washing field comprises holding the electric field in one configuration for an additional washing time.

10. The method of claim 8, wherein applying the washing field comprises applying an electric field that is high in the wash arm and low in the other n−1 of the separation arms for a washing time.

11. The method of claim 4, wherein the target and background particles comprise target and background oligonucleotides.

12. The method of claim 11, further comprising:
providing an immobilized oligonucleotide probe having a sequence complementary to the target oligonucleotide but with at least one mismatch for the background oligonucleotide in the separation medium, thereby providing an affinity matrix;
selecting a temperature at which the mobility of the background oligonucleotide through the affinity matrix is significantly greater than the mobility of the target oligonucleotide through the affinity matrix as a low temperature;
selecting a temperature at which the mobility of both the background oligonucleotide and the target oligonucleotide through the affinity matrix is approximately equal and approaches the unbound mobility as a high temperature; and
regulating the temperature of the separation medium in each one of the separation arms so that the separation medium is at approximately the low temperature during the time that the electric field strength in each one of the separation arms is low, and so that the separation medium is at approximately the high temperature during the time that the electric field strength in each one of the separation arms is high.

13. The method of claim 12, wherein the target oligonucleotide has a point mutation from a wild type oligonucleotide and the background oligonucleotide is the wild type oligonucleotide.

14. The method of claim 12, wherein regulating comprises allowing Joule heating to increase the temperature in one of the separation arms.

15. The method of claim 11, further comprising:
providing an immobilized oligonucleotide probe having a sequence complementary to the target oligonucleotide in the separation medium, thereby providing an affinity matrix;
selecting a temperature at which the mobility of a differently-methylated target oligonucleotide through the affinity matrix is significantly different from the mobility of the target oligonucleotide through the affinity matrix as a low temperature;
selecting a temperature at which the mobility of both the differently-methylated target oligonucleotide and the target oligonucleotide through the affinity matrix is approximately equal and approaches the unbound mobility as a high temperature; and
regulating the temperature of the separation medium in each one of the separation arms so that the separation medium is at approximately the low temperature during the time that the electric field strength in each one of the separation arms is low, and so that the separation medium is at approximately the high temperature during the time that the electric field strength in each one of the separation arms is high.

16. The method of claim 15, wherein regulating comprises allowing Joule heating to increase the temperature in one of the separation arms.

\* \* \* \* \*